US009163219B2

(12) United States Patent
Curtiss, III et al.

(10) Patent No.: US 9,163,219 B2

(45) Date of Patent: Oct. 20, 2015

(54) SINGLE EXPRESSION VECTOR FOR GENERATION OF A VIRUS WITH A SEGMENTED GENOME

(75) Inventors: Roy Curtiss, III, Tempe, AZ (US); Xiangmin Zhang, Tempe, AZ (US)

(73) Assignee: Arizona Board of Regents on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 12/759,842

(22) Filed: Apr. 14, 2010

(65) Prior Publication Data

US 2010/0285592 A1 Nov. 11, 2010

Related U.S. Application Data

(60) Provisional application No. 61/168,996, filed on Apr. 14, 2009.

(51) Int. Cl.

| | |
|---|---|
| ***C12N 15/63*** | (2006.01) |
| ***C12N 1/21*** | (2006.01) |
| ***C12N 7/00*** | (2006.01) |
| ***C07K 14/005*** | (2006.01) |
| ***C12N 15/85*** | (2006.01) |

(52) U.S. Cl.

CPC ................ *C12N 7/00* (2013.01); *C07K 14/005* (2013.01); *C12N 15/85* (2013.01); *C12N 2760/16051* (2013.01); *C12N 2760/16122* (2013.01); *C12N 2760/16151* (2013.01); *C12N 2800/103* (2013.01); *C12N 2830/36* (2013.01); *C12N 2840/20* (2013.01)

(58) Field of Classification Search

None

See application file for complete search history.

(56) References Cited

U.S. PATENT DOCUMENTS

| | | | |
|---|---|---|---|
| 4,190,495 | A | 2/1980 | Curtiss, III |
| 4,888,170 | A | 12/1989 | Curtiss, III |
| 4,968,619 | A | 11/1990 | Curtiss, III |
| 5,210,035 | A | 5/1993 | Stocker |
| 5,294,441 | A | 3/1994 | Curtiss, III |
| 5,387,744 | A | 2/1995 | Curtiss |
| 5,389,368 | A | 2/1995 | Curtiss, III |
| 5,424,065 | A | 6/1995 | Curtiss, III |
| 5,468,485 | A | 11/1995 | Curtiss, III |
| 5,536,658 | A | 7/1996 | Shotts, Jr. et al. |
| 5,654,184 | A | 8/1997 | Curtiss, III |
| 5,656,488 | A | 8/1997 | Curtiss, III |
| 5,672,345 | A | 9/1997 | Curtiss, III |
| 5,679,880 | A | 10/1997 | Curtiss, III |
| 5,686,079 | A | 11/1997 | Curtiss, III |
| 5,817,317 | A | 10/1998 | Titball |
| 5,827,705 | A | 10/1998 | Dean |
| 5,840,483 | A | 11/1998 | Curtiss, III |
| 5,855,879 | A | 1/1999 | Curtiss, III |
| 5,855,880 | A | 1/1999 | Curtiss, III |
| 5,961,983 | A | 10/1999 | Brey et al. |
| 6,024,961 | A | 2/2000 | Curtiss, III |
| 6,180,614 | B1 | 1/2001 | Davis |
| 6,248,329 | B1 | 6/2001 | Chandrashekar et al. |
| 6,350,454 | B1 | 2/2002 | Thune |
| 6,383,496 | B1 | 5/2002 | Curtiss, III |
| 6,399,074 | B1 | 6/2002 | Roland |
| 6,403,094 | B1 | 6/2002 | Titball |
| 6,610,529 | B1 | 8/2003 | Curtiss, III |
| 6,780,405 | B1 | 8/2004 | Curtiss, III |
| 6,872,547 | B1 | 3/2005 | Curtiss, III |
| 6,969,513 | B2 | 11/2005 | Galen |
| 7,083,794 | B2 | 8/2006 | Curtiss, III |
| 7,195,757 | B2 | 3/2007 | Curtiss, III |
| 7,205,125 | B2 | 4/2007 | Castillo |
| 7,341,860 | B2 | 3/2008 | Curtiss, III |
| 7,871,604 | B1 | 1/2011 | Curtiss, III |
| 7,968,101 | B2 * | 6/2011 | Kawaoka et al. .......... 424/206.1 |
| 8,133,493 | B2 | 3/2012 | Curtiss, III |
| 8,445,254 | B2 | 5/2013 | Curtiss, III et al. |
| 8,465,755 | B2 | 6/2013 | Curtiss, III et al. |
| 2003/0031683 | A1 | 2/2003 | Curtiss, III |
| 2003/0175772 | A1 | 9/2003 | Wang |
| 2004/0077556 | A1 | 4/2004 | Chinery |
| 2004/0101531 | A1 | 5/2004 | Curtiss, III |
| 2004/0120962 | A1 | 6/2004 | Curtiss, III |

(Continued)

FOREIGN PATENT DOCUMENTS

| | | | |
|---|---|---|---|
| EP | 0315682 | B1 | 12/1993 |
| EP | 0381706 | B1 | 4/1995 |

(Continued)

OTHER PUBLICATIONS

Nieto et al (Journal of General Virology, 1994. vol. 75, pp. 29-36, abstract).*

Dean (Experimental Cell Research, 1997. vol. 230, pp. 293-302).*

Kotton et al., Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of arac autoregulation and the domains of two overlapping promoters, PC and PBAD, in the L-arabinose regulatory region of *Escherichia coli*. Proc. Natl. Acad. Sci. U S A, 1981, pp. 752-756, vol. 78.

Li et al., A sopB Deletion Mutation Enhances the Immunogenicity and Protective Efficacy of a Heterologous Antigen Delivered by Live Attenuated *Salmonella* enterica Vaccines. Infection and Immunity, 2008, pp. 5238-5246, vol. 76, No. 11.

(Continued)

*Primary Examiner* — Celine Qian

(74) *Attorney, Agent, or Firm* — Rebecca C. Riley-Vargas; Polsinelli PC

(57) ABSTRACT

The present invention encompasses an expression vector that is capable of generating a virus from a segmented genome. In particular, a single expression vector may be utilized to produce influenza virus in cultured cells. The expression vector can be delivered in a purified DNA form or by a suitably designed bacterial carrier to cells in culture or to animals. This invention increases the virus generation efficiency, which benefits vaccine development. The bacterial carrier harboring such a plasmid encoding an attenuated virus may be used as a vaccine against corresponding viral disease.

3 Claims, 16 Drawing Sheets

(11 of 16 Drawing Sheet(s) Filed in Color)

(56) References Cited

U.S. PATENT DOCUMENTS

2004/0137003 A1 7/2004 Curtiss, III
2004/0203039 A1 10/2004 Hensel
2005/0036987 A1 2/2005 Pawelek
2005/0106175 A1 5/2005 Montanes
2005/0106176 A1 5/2005 Curtiss, III
2005/0118193 A1 6/2005 Andino-Pavlovsky et al.
2006/0140975 A1 6/2006 Curtiss, III
2006/0171917 A1 8/2006 Campbell
2006/0206961 A1 9/2006 Cirpus
2006/0233829 A1 10/2006 Curtiss, II
2006/0234346 A1 10/2006 Retallack
2006/0275255 A1 12/2006 Gudkov
2007/0025981 A1 2/2007 Szalay
2008/0096809 A1 4/2008 Shai
2008/0248066 A1 10/2008 Dubensky, Jr.
2009/0175829 A1 7/2009 Forbes
2010/0124558 A1 5/2010 Curtiss, III
2010/0154293 A1 6/2010 Hom et al.
2010/0255022 A1 10/2010 Prescott et al.
2010/0285592 A1 11/2010 Curtiss, III
2010/0317084 A1 12/2010 Curtiss, II
2011/0033501 A1 2/2011 Curtiss, III et al.
2011/0256181 A1 10/2011 Curtiss, III
2011/0287052 A1 11/2011 Curtiss, III et al.
2012/0087946 A1 4/2012 Curtiss, III
2013/0004537 A1 1/2013 Curtiss, III et al.
2013/0171190 A1 7/2013 Curtiss, III et al.

FOREIGN PATENT DOCUMENTS

EP 0465560 B1 6/1996
EP 0500699 B1 6/1998
EP 0558631 B1 3/1999
EP 0433372 B1 6/2002
EP 1030690 B1 7/2002
EP 0556333 B1 3/2003
EP 1326960 B1 12/2004
EP 0832255 B1 12/2005
EP 1537214 B1 3/2006
EP 1292687 B1 8/2006
WO 88/09669 A1 12/1988
WO 89/03427 A1 4/1989
WO 90/02484 A1 3/1990
WO 90/11687 A1 10/1990
WO 90/11688 A1 10/1990
WO 90/12086 A1 10/1990
WO 91/06317 A1 5/1991
WO 92/08486 A1 5/1992
WO 92/09684 A1 6/1992
WO 93/04202 A1 3/1993
WO 94/24291 A2 10/1994
WO 94/24291 A3 12/1994
WO 96/40947 A1 12/1996
WO 99/25387 A1 5/1999
WO 01/83785 A2 11/2001
WO 02/30457 A2 4/2002
WO 01/83785 A3 6/2002
WO 02/059292 A2 8/2002
WO 03/079792 A1 10/2002
WO 02/030457 A3 1/2003
WO 02/030457 A3 7/2003
WO 02/059292 A3 7/2003
WO 03/096812 A1 11/2003
WO 2004/020643 A2 3/2004
WO 2004/020643 A3 4/2004
WO 2005/001069 A1 1/2005
WO 2008/141226 A2 11/2008
WO 2009/025888 A2 2/2009
WO 2009/046449 A1 4/2009
WO 2009/046451 A1 4/2009
WO 2010/045620 A1 4/2010
WO 2010/078584 A1 8/2010
WO 2010/135563 A1 11/2010
WO 2011/091291 A1 7/2011
WO 2011/150421 A2 12/2011
WO 2012087483 A1 6/2012

OTHER PUBLICATIONS

Lee et al., Trigger factor retards protein export in *Escherichia coli*. J Biol Chem, 2002, pp. 43527-43535, vol. 277.

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+ T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol., 2005, pp. 13811-13816, vol. 79.

Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.

McClelland et al., Complete genome sequence of *Salmonella enterica* serovar Typhimurium LT2. Nature, 2001, pp. 852-856, vol. 413, No. 6858.

McDaniel et al., Monoclonal antibodies against protease sensitive pneumococcal antigens can protect mice from fatal infection with *Streptococcus pneumoniae*. J. Exp. Med., 1984, pp. 368-97, vol. 160.

McDaniel et al., Use of insertional inactivation to facilitate studies of biological properties of pneumococcal surface protein A (PspA). J. Exp. Med., 1987, pp. 381-394, vol. 165.

Mesika et al., A regulated, NF κb-assisted import of plasmid DNA into mammalian cell nuclei. Mol. Ther., 2001, pp. 653-657, vol. 3.

Miller et al., A novel suicide vector and its use in construction of insertion mutations: osmoregulation of outer membrane proteins and virulence determinants in *Vibrio cholerae* requires toxR. J Bacteriol, 1988, pp. 2575-2583, vol. 170.

Miller et al., Bacteriophage T4 genome. Microbiol Mol Biol Rev, 2003, pp. 86-156, vol. 67, No. 1.

Molinari et al., The annual impact of seasonal influenza in the US: measuring disease burden and costs. Vaccine, 2007, pp. 5086-50896, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expressed in attenuated *Salmonella* typhimurium elicit mucosal and systemic neutralizing antibodies in mice. Infect Immun, 1997, pp. 3328-3336, vol. 65.

Nayak et al., A live recombinant avirulent oral *Salmonella* vaccine expressing pneumococcal surface protein A induces protective responses against *Streptococcus pneumoniae*. Infect Immun., 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs. Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Nickerson et al., Role of sigma factor RpoS in initial stages of *Salmonella* typhimurium infection. Infect Immun, 1997, pp. 1814-1823, vol. 65.

(56) References Cited

OTHER PUBLICATIONS

Noda et al., Architecture of ribonucleoprotein complexes in influenza A virus particles. Nature, 2006, pp. 490-492, vol. 439.
Oehler et al., The three operators of the lac operon cooperate in repression. EMBO J, 1990, pp. 973-979, vol. 9, No. 4.
Ogunniyi et al., Contributions of Pneumolysin, Pneumococcal Surface Protein a (PspA), and PspC to Pathogenicity of *Streptococcus pneumoniae* D39 in a Mouse Model. Infect. Immun., 2007, pp. 1843-1851, vol. 75.
Osterholm, Preparing for the next pandemic. N. Engl. J. Med., 2005, pp. 1839-1842, vol. 352.
Ozaki et al., Generation of high-yielding influenza A viruses in African green monkey kidney (Vero) cells by reverse genetics. J. Virol., 2004, pp. 1851-1857, vol. 78.
Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic *Escherichia coli* Colonization Factor Antigen I by *Salmonella* Typhimurium Elicits a Biphasic T Helper Cell Response. Infec. Immun., 1999, pp. 6249-6256, vol. 67.
Pashine et al., Th1 dominance in the immune response to live *Salmonella* Typhimurium requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates *Salmonella* virulence nucleic acid sequence expression. Mol Microbiol, 2004, pp. 1827-1844, vol. 52, No. 6.
Prouty et al., *Salmonella enterica* serovar Typhimurium invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of *Salmonella* strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.
Schodel et al., Hybrid hepatitis B virus core-pre-S proteins synthesized in avirulent *Salmonella* typhimurium and *Salmonella* typhi for oral vaccination. Infect Immun, 1994, pp. 1669-1676, vol. 62, No. 5.
Schodel, Recombinant avirulent Salmonellae as oral vaccine carriers. Infection, 1992, pp. 1-8, vol. 20.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Siegele et al., Gene Expression from plasmids containing the araBAD promoter at subsaturating inducer concentrations represents mixed populations. Proc Natl Acad Sci U S A, 1997, pp. 8168-8172, vol. 94, No. 15.
Simonsen et al., The impact of influenza epidemics on hospitalizations. J. Infect. Dis., 2000, pp. 831-837, vol. 181.
PCT/US2008/063303 (WO 2008/141226)—International Search Report and Written Opinion of the International Searching Authority, Nov. 26, 2008.
PCT/US2008/063293 (WO 2009/025888)—International Search Report and Written Opinion of the International Searching Authority, Feb. 12, 2009.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.
PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.
PCT/US2011/038588 (WO 2011/150421)—International Search Report and Written Opinion of the International Searching Authority, Nov. 22, 2011.
PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995 by A. Ormerod.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.

(56) References Cited

OTHER PUBLICATIONS

European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
CDC, Update: influenza activity—United States, Sep. 30, 2007-Apr. 5, 2008, and composition of the Sep. 2008 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
Collins et al., Mutations at rfc or pmi attenuate *Salmonella* Typhimurium virulence for mice. Infect. Immun., 1991, pp. 1079-1085, vol. 59.
Curtiss et al., Avirulent *Salmonella* typhimurium delta cya delta crp oral vaccine strains expressing a streptococcal colonization and virulence antigen. Vaccine, 1988, pp. 155-160, vol. 6.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella* typhimurium deletion mutants lacking adenylate cyclase and cyclic AMP receptor protein are avirulent and immunogenic. Infect Immun, 1987, pp. 3035-3043, vol. 55.
Curtiss et al., Stabilization of recombinant avirulent vaccine strains in vivo. Res Microbiol, 1990, pp. 797-805, vol. 141.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella* typhi genes expressed within macrophages by selective capture of transcribed sequences (SCOTS). Mol Microbiol, 2001, pp. 1211-1222, vol. 41.
Darzins. Nucleotide-sequence analysis of the phosphomannose isomerase gene (PMI) of *Pseudomonas aeruginosa* and comparison with the corresponding *Escherichia-coli* gene mana. Gene, 1986, pp. 293-302, vol. 42, No. 3.
Dean, 1997. Import of plasmid DNA into the nucleus is sequence specific. Exp. Cell Res., 1997, pp. 293-302, vol. 230.
Doggett et al., Immune responses to *Streptococcus sobrinus* surface protein antigen A expressed by recombinant *Salmonella* typhimurium. Infect Immun, 1993, pp. 1859-1866, vol. 61.
Dunstan et al., Comparison of the Abilities of Different Attenuated *Salmonella* Typhimurium Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella* typhimurium expressing a cloned *Porphyromonas gingivalis* hemagglutinin. Infect Immun, 1994, pp. 1652-1657, vol. 62, No. 5.
Egan et al., A regulatory cascade in the induction of rhaBAD. J Mol Biol, 1993, pp. 97-98, vol. 234.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of *Shigella sonnei* form I antigen genes into the galE *Salmonella* typhi Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.
Galan et al., Cloning and molecular characterization of genes whose products allow *Salmonella* typhimurium to penetrate tissue culture cells. Proc Natl Acad Sci U S A, 1989, pp. 6383-6387, vol. 86.
Galen et al., Optimization of Plasmid Maintenance in the Attenuated Live Vector Vaccine Strain *Salmonella* typhi CVD 908-htrA. Infect. Immun., 1999, pp. 6424-6433, vol. 67.
Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.
Gay et al., Positive selection procedure for entrapment of insertion sequence elements in gram-negative bacteria. J Bacteriol, 1985, pp. 918-921, vol. 164, No. 2.
Gentschev et al., Delivery of the p67 sporozoite antigen of *Theileria parva* by using recombinant *Salmonella* dublin: secretion of the product enhances specific antibody responses in cattle. Infect. Immun., 1998, pp. 2060-2064, vol. 66.
Gerdil, The annual production cycle for influenza vaccine. Vaccine, 2003, pp. 1776-1779, vol. 21.
Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.
Greenwood, The epidemiology of pneumococcal infection in children in the developing world. Philos. Trans. R. Soc. Lond. B. Biol. Sci., 1999, pp. 777-785, vol. 354.
Gulig et al., Plasmid-associated virulence of *Salmonella* typhimurium. Infect Immun, 1987, pp. 2891-2901, vol. 55.
Guzman et al., Tight regulation, modulation, and high-level expression by vectors containing the arabinose PBAD promoter. J Bacteriol, 1995, pp. 4121-4130, vol. 177.
Hall et al., The role of fur in the acid tolerance response of *Salmonella* typhimurium is physiologically and genetically separable from its role in iron acquisition. J Bacteriol, 1996, pp. 5683-5691, vol. 178.
Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.
Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.
Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.
Hoffmann et al., "Ambisense" approach for the generation of influenza A virus: vRNA and mRNA synthesis from one template. Virology, 2000, pp. 310-317, vol. 267.

(56) References Cited

OTHER PUBLICATIONS

Hohmann et al., Macrophage-inducible expression of a model antigen in *Salmonella* typhimurium enhances immunogenicity. Proc Natl Acad Sci U S A, 1995, pp. 2904-2908, vol. 92, No. 7.
Hollingshead et al., Diversity of PspA: mosaic genes and evidence for past recombination in *Streptococcus pneumoniae*. Infect Immun., 2000, pp. 5889-5900, vol. 68.
Hopkins et al., A recombinant *Salmonella* typhimurium vaccine induces local immunity by four different routes of immunization. Infect Immun, 1995, pp. 3279-3286, vol. 63.
Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.
Kang et al., Immune responses dependent on antigen location in recombinant attenuated *Salmonella* typhimurium vaccines following oral immunization. FEMS Immunol. Med. Microbiol. Lett., 2003, pp. 99-104, vol. 37.
Kang et al., Immune responses to recombinant pneumococcal PspA antigen delivered by live attenuated *Salmonella enterica* serovar typhimurium vaccine. Infect. Immun., 2002, pp. 1739-1749, vol. 70.
Kang et al., Transduction-mediated transfer of unmarked deletion and point mutations through use of counterselectable suicide vectors. J Bacteriol, 2002, pp. 307-312, vol. 184.
Katzman et al., Invertebrate connective tissue. Isolation of D-arabinose from sponge acidic polysaccharide. Biochem J, 1970, pp. 17-19, vol. 119, No. 1.
Kennedy et al., Attenuation and immunogenicity of Delta cya Delta crp derivatives of *Salmonella choleraesuis*in pigs. Infection and Immunity, 1999, pp. 4628-4636, vol. 67, No. 9.
Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.
Klumpp et al., Roles of the influenza virus polymerase and nucleoprotein in forming a functional RNP structure. EMBO J., 1997, pp. 1248-1257, vol. 16.
Kong et al, Regulated programmed lysis of recombinant *Salmonella* in host tissues to release protective antigens and confer biological containment. PNAS, 2008, pp. 9361-9366, vol. 105, No. 27.
Konjufca et al., A Recombinant Attenuated *Salmonella enterica* Serovar Typhimurium Vaccine Encoding *Eimeria acervulina* Antigen Offers Protection against *E. acervulina* Challenge. Infect. Immun., 2006, pp. 6785-6796, vol. 74.
Song et al., Organization and regulation of the D-xylose operons in *Escherichia coli* K-12: XyIR acts as a transcriptional activator. J Bacteriol, 1997, pp. 7025-7032, vol. 179.
Spellberg et al., Type 1/type 2 immunity in infectious diseases. Clin. Infect. Dis., 2001, pp. 76-102, vol. 32.
Schnaitman et al., Genetics of Lipopolysaccharide Biosynthesis in Enteric Bacteria. Microbiological Reviews, 1993, pp. 655-682, vol. 57, No. 3.
Srinivasan et al., Oral immunization with attenuated *Salmonella* expressing human sperm antigen induces antibodies in serum and the reproductive tract. Biol Reprod, 1995, pp. 462-471, vol. 53.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella* typhi vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella* typhimurium. InfectImmun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella* typhimurium SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.
PCT/US2011/061896—International Search Report and Written Opinion of the International Searching Authority, Apr. 5, 2012.
Byl et al, Sequence of the Genomore of *Salmonella* Bacteriophage P22. Journal of Bacteriology, 2000, pp. 6472-6484, vol. 182, 22.
Houng et al., Expression of Vi antigen in *Escherichia coli* K-12: characterization of ViaB from *Citrobacter freundii* and identity of ViaA with RcsB. J.Bacterio, 1992, pp. 5910-5915, vol. 174, No. 18.
Hori et al, Constructionof selt-disruptive *Bacillus megaterium* in response to substrate exhaustion for polyhydroxybutryrate production. Appl Microbiol Biotechnol, 2002, pp. 211-216, vol. 59.
Hurme et al, A Proteinaceous Gene Regulator Thermameter in *Salmonella*. Cell, 1997, pp. 55-64, vol. 90.
Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.
Pickard et al., Characterization of defined ompR mutants of *Salmonella* typhi: ompR is involved in the regulation of VI polysaccharide expression. Infect Immun, 1994, pp. 3984-3893, vol. 62, No. 9.
Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Takaya et al., The ATP-Dependent Lon Protease of *Salmonella enterica* Serovar Typhimurium Regulates Invasion and Expression of Genes Carried on *Salmonella* Pathogenicity Island 1. Journal of Bacteriology, 2002, pp. 224-232, vol. 184, No. 1.
Waltman et al., Biochemical Characteristics of *Edwardsiella ictaluri*. Applied and Enviornmental Microbiology, 1986, pp. 101-104, vol. 51, No. 1.
Sun et al. Highly efficient method for introducing successive multiple scarless gene deletions and markerless gene insertions into the *Yersinia pestis* chromosome. Appl Environ Microbiol, 2008, pp. 4241-4245, vol. 74.
U.S. Appl. No. 13/006,072, Office Action dated Apr. 19, 2012.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.

(56) References Cited

OTHER PUBLICATIONS

U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
U.S. Appl. No. 12/615,872, Office Action dated Mar. 14, 2012.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica* serovar Typhimurium. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella* typhimurium against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehydel Biol. Chem., 1955, pp. 39-50, vol. 213.
Briles et al., Immunization of humans with recombinant pneumococcal surface protein a (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.
Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for *Salmonella* virulence in mice. J. Clin. Invest., 1995, pp. 1047-1053, vol. 95.
Bumann, Regulated antigen expression in live recombinant *Salmonella enterica* serovar Typhimurium strongly affects colonization capabilities and specific CD4(+)-T-cell responses. Infect Immun, 2001. pp. 7493-7500, vol. 69, No. 12.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of *Bordetella pertussis* using an attenuated *Salmonella* typhimurium vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella* typhi differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from *Yersinia pestis* Kim delivered by live attenuated *Salmonella*typhimurium elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, the Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The Act domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.

(56) References Cited

OTHER PUBLICATIONS

Coombes et al., SseL Is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia*, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.
Curtiss et al., Recombinant *Salmonella vectors* in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella* typhimurium. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* Kim. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murl gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella* typhimurium are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the *Yersinia pestis* Yfu ABC inorganic iron transport system. Infect Immun, 2001, pp. 2829-2837, vol. 69.
Gor et al., TH1-TH2: a Procrustean paradigm. Nat Immunol, 2003, p. 503-505, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
Hess et al., Secretion of different listeriolysin cognates by recombinant attenuated *Salmonella* typhimurium: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella* typhi vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in Xenopus oocytes. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella* typhimurium. Molecular Microbiology, 1995, pp. 155-167, vol. 17.
Isoda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of *Yersinia pestis* by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., *Salmonella*-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella* typhimurium LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.
Marshall et al., Use of the stationary phase inducible promoters, spy and dps, to drive heterologous antigen expression in *Salmonella* vaccine strains. Vaccine, 2000, pp. 1298-1306, vol. 18, No. 14.

(56) References Cited

OTHER PUBLICATIONS

Medina et al., Use of live bacterial vaccine vectors for antigen delivery: potential and limitations. Vaccine, 2001, pp. 1573-1580, vol. 19.
Mehigh et al., Expression of the low calcium response in *Yersinia pestis*. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the *Yersinia pestis* V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella* typhimurium and *Salmonella* typhi by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of *Yersinia pestis* is posttranscriptional. J Bacteriol, 2004, pp. 1638-1647, vol. 186.
Petersen et al., Essential role for cyclic AMP and its receptor protein in *Yersinia enterocolitica* virulence. Infect Immun, 2004, pp. 3665-3672, vol. 70.
Ramarathinam et al., *Salmonella* Typhimurium induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp *Salmonella* typhimurium strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of *Yersinia pestis* is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella* typhimurium. Methods Enzymol, 1991, pp. 18-43, vol. 204.
Straley et al., Virulence genes regulated at the transcriptional level by Ca2+ in *Yersinia pestis* include structural genes for outer membrane proteins. Infect Immun, 1986, pp. 445-454, vol. 51.
Sun et al., The role of relA and spoT in *Yersinia pestis* KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.
Une et al., In vivo comparison of avirulent Vwa- and Pgm- or Pstr phenotypes of Yersiniae. Infect Immun, 1984, pp. 895-900, vol. 43.
Uzzau et al., Epitope tagging of chromosomal genes in *Salmonella*. Proc Natl Acad Sci U S A, 2001, pp. 15264-15269, vol. 98.
Viboud et al., *Yersinia* outer proteins: role in modulation of host cell signaling responses and pathogenesis. Annu Rev Microbiol, 2005, pp. 69-89, vol. 59.
Wasserman et al., Two alanine racemase genes in *Salmonella* typhimurium that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in *Yersinia pestis*. Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in *Rhodococcus opacus* PD630 and *Mycobacterium smegmatis* mc2155, and provides an anchor to target other proteins.

(56) References Cited

OTHER PUBLICATIONS

Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.

Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.

Morita et al., Antibacterial Activity of *Bacillus amyloliquefaciencs* Phage Endolysin without Holin Conjugation. Journal of Biosciences and Bioengineering, 2001, pp. 469-473, vol. 91, No. 5.

Navasa et al, Temperature has reciprocal effects on colanic acid and polysialic acid biosynthesis in *E. coli* K92. Appl Microbiol Biotechnol, 2009, pp. 721-729, vol. 82.

Stevens, Immunization with the C-Domain of alpha-Toxin Prevents Lethal Infection, Localizes Tissue Injury, and Promotes Host Responses to Challenge with *Clostridium perfringens*. JID, 2004, pp. 767-773, vol. 190.

Verjan et al, Genetic Loci of Major Antigenic Protein Genes of *Edwardsiella tarda*. Applied and Environmental Microbiology, 2005, pp. 5654-5658, vol. 71, No. 9.

U.S. Appl. No. 12/599,655, Office Action dated Jul. 2, 2012.

U.S. Appl. No. 12/681,721, Office Action dated May 24, 2012.

Ellis, R, New Technologies for Making Vaccines. Vaccines, 1988, pp. 568-574, W.B. Saunders Company, Philadelphia.

Greenspan et al, Defining epitopes: It's not as easy as it seems. Nature Biotechnology, 1999, pp. 936-937, vol. 17.

Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25, Cold Spring Harbor Laboratory, USA.

U.S. Appl. No. 12/599,655, Office Action dated Mar. 12, 2013.

U.S. Appl. No. 12/681,711, Office Action dated Nov. 28, 2012.

U.S. Appl. No. 12/789,869, Office Action dated Jun. 3, 2014.

U.S. Appl. No. 13/088,141, Office Action dated Apr. 24, 2014.

U.S. Appl. No. 13/574,718, Office Action dated Sep. 6, 2013.

U.S. Appl. No. 13/574,718, Office Action dated Apr. 28, 2014.

U.S. Appl. No. 13/700,591, Office Action dated Apr. 2, 2014.

U.S. Appl. No. 13/898,241, Office Action dated Apr. 17, 2014.

Bittner et al., RpoS and RpoN are involved in the growth-dependent regulation of rfaH transcription and O antigen expression in *Salmonella enterica* serovar Typhi, Microbial Pathogenisis. vol. 36, 2004 (p. 19).

Liu et al., Nickel-inducible lysis system in *Synechocystis* sp. PCC 6803. PNAS, vol. 106, 2009, pp. 21550-21554.

Liu et al., CO2—limitation-inducible Green Recovery of fatty acids from cyanobacterial biomass. PNAS, vol. 108, 2011 pp. 6905-6908.

Moreno et al., *Salmonella* as Live Trojan Horse for Vaccine Development and Cancer Gene Therapy. Current Gene Therapy, 2010, 10, pp. 56-76.

U.S. Appl. No. 13/302,575, Office Action dated Jun. 18, 2013.

Folkesson et al., Components of the peptidoglycan-recycling pathway modulate invasion and intracellular survival of *Salmonella enterica* serovar Typhimurium. Cellular Microbiology, 2005, vol. 7(1) pp. 147-155.

Whitworth et al., Expression of the *Rickettsia prowazekii* pld or tlyC Gene in *Salmonella enterica* Serovar Typhimurium Mediates Phagosomal Escape, Infection and Immunity, 2005, vol. 73(10), pp. 6668-6673.

Quenee, Lauriane E., et al., *Yersinia pestis* caf1 Variants and the Limits of Plague Vaccine Protection, Infection and Immunity, May 2008, vol. 76, No. 5, pp. 2025-2036.

U.S. Appl. No. 13/088,141, Office Action dated Dec. 6, 2012 (Ginny Portner).

U.S. Appl. No. 13/006,072, Office Action dated Dec. 11, 2012 (Ja'Na Hines).

Kong, W., T-10-, Improving DNA Vaccine Vector for Efficient Vaccine Delivery Using Live Attenuated Bacterial Carrier, The Society, vol. 2008, No. 108, pp. 668.

Mesika, Adi, et al., A Regulated, NF kB-Assisted Import of Plasmid DNA into Mammalian Cell Nuclei, Molecular Therapy, vol. 3, No. 5, May 2001, pp. 653-657.

Ribeiro, Sofia C., et al., The Role of Polyadenylation Signal Secondary Structures on the Resistance of Plasmid Vectors to Nucleases, The Journal of Gene Medicine, vol. 6, 2004, pp. 565-573.

Rytkonen, Anne, et al.,. SseL, a *Salmonella* Deubiquitinase Required for Macrophage Killing and Virulence, PNAS, vol. 104, No. 9, Feb. 27, 2007, pp. 3502-3507.

Wang, Shixia, et al., Hemagglutinin (HA) Proteins from H1 and H3 Serotypes of Influenza a Viruses Require Different Antigen Designs for the Induction of Optimal Protective Antibody Responses as Studied by Codon-Optimized HA DNA Vaccines, Journal of Virology, vol. 80, No. 23, Dec. 2006, pp. 11628-11637.

U.S. Appl. No. 13/302,575, Office Action dated Sep. 25, 2012 (Oluwatosin Ogunbiyi).

U.S. Appl. No. 12/615,872, Office Action dated Oct. 23, 2012 (Jennifer Graser).

American Society of Microbiology, vol. 108; 2008: (p. 668).

* cited by examiner

SEQUENCE LISTING

<160> NUMBER OF SEQ ID NOS: 61

<210> SEQ ID NO 1
<211> LENGTH: 25
<212> TYPE: DNA
<213> ORGANISM: Artificial Sequence
<220> FEATURE:
<223> OTHER INFORMATION: GALLUS GALLUS

<400> SEQUENCE: 1
tcggtcgctt cgcggaggtg gctgg 25

<210> SEQ ID NO 2
<211> LENGTH: 25
<212> TYPE: DNA
<213> ORGANISM: Artificial Sequence
<220> FEATURE:
<223> OTHER INFORMATION: GALLUS GALLUS

<400> SEQUENCE: 2
gtgatcgcct tctccggctt ttttt 25

<210> SEQ ID NO 3
<211> LENGTH: 27
<212> TYPE: DNA
<213> ORGANISM: Artificial Sequence
<220> FEATURE:
<223> OTHER INFORMATION: GALLUS GALLUS

<400> SEQUENCE: 3
taaaagcttt ctgcagaatt cgcccctt 27

<210> SEQ ID NO 4
<211> LENGTH: 29
<212> TYPE: DNA
<213> ORGANISM: Artificial Sequence
<220> FEATURE:
<223> OTHER INFORMATION: GALLUS GALLUS

<400> SEQUENCE: 4
ttaggtacca cctgctccta cagacgaac 29

<210> SEQ ID NO 5
<211> LENGTH: 32
<212> TYPE: DNA
<213> ORGANISM: Artificial Sequence
<220> FEATURE:
<223> OTHER INFORMATION: MUS MUSCULUS

<400> SEQUENCE: 5
taaggtacca cctgctgctc ccccccaact tc 32

<210> SEQ ID NO 6
<211> LENGTH: 24
<212> TYPE: DNA
<213> ORGANISM: Artificial Sequence
<220> FEATURE:
<223> OTHER INFORMATION: MUS MUSCULUS

<400> SEQUENCE: 6
ttagctagcg tgtcgcccgg agta 24

<210> SEQ ID NO 7
<211> LENGTH: 50
<212> TYPE: DNA
<213> ORGANISM: Artificial Sequence
<220> FEATURE:
<223> OTHER INFORMATION: COMPLETELY ARTIFICIAL

<400> SEQUENCE: 7
taacgtctct ctgtagtaga aacaaggtag ttttttactt gtacagctcg 50

<210> SEQ ID NO 8
<211> LENGTH: 55
<212> TYPE: DNA
<213> ORGANISM: Artificial Sequence
<220> FEATURE:
<223> OTHER INFORMATION: COMPLETELY ARTIFICIAL

<400> SEQUENCE: 8
ttacgtctct ggggagcaaa agcaggtaga tattgaaaga tggtgagcaa gggcg 55

<210> SEQ ID NO 9
<211> LENGTH: 27
<212> TYPE: DNA
<213> ORGANISM: Artificial Sequence
<220> FEATURE:
<223> OTHER INFORMATION: COMPLETELY ARTIFICIAL

<400> SEQUENCE: 9
acctctagaa tggtgagcaa gggcgag 27

<210> SEQ ID NO 10
<211> LENGTH: 27
<212> TYPE: DNA
<213> ORGANISM: Artificial Sequence
<220> FEATURE:
<223> OTHER INFORMATION: COMPLETELY ARTIFICIAL

<400> SEQUENCE: 10
taagaattct tacttgtaca gctcgtc 27

<210> SEQ ID NO 11
<211> LENGTH: 25
<212> TYPE: DNA
<213> ORGANISM: Artificial Sequence
<220> FEATURE:
<223> OTHER INFORMATION: COMPLETELY ARTIFICIAL

<400> SEQUENCE: 11
taactcgaga tggaaagaat aaaag 25

<210> SEQ ID NO 12
<211> LENGTH: 25
<212> TYPE: DNA
<213> ORGANISM: Artificial Sequence
<220> FEATURE:
<223> OTHER INFORMATION: COMPLETELY ARTIFICIAL

<400> SEQUENCE: 12
ttaggtaccc taattgatgg ccatc 25

<210> SEQ ID NO 13
<211> LENGTH: 25
<212> TYPE: DNA
<213> ORGANISM: Artificial Sequence
<220> FEATURE:
<223> OTHER INFORMATION: COMPLETELY ARTIFICIAL

<400> SEQUENCE: 13
taactcgaga tggatgtcaa tccga 25

<210> SEQ ID NO 14
<211> LENGTH: 25
<212> TYPE: DNA
<213> ORGANISM: Artificial Sequence
<220> FEATURE:
<223> OTHER INFORMATION: COMPLETELY ARTIFICIAL

<400> SEQUENCE: 14
ttaggtaccc tatttttgcc gtctg 25

<210> SEQ ID NO 15
<211> LENGTH: 25
<212> TYPE: DNA
<213> ORGANISM: Artificial Sequence
<220> FEATURE:
<223> OTHER INFORMATION: COMPLETELY ARTIFICIAL

<400> SEQUENCE: 15
taactcgaga tggaagattt tgtgc 25

<210> SEQ ID NO 16
<211> LENGTH: 25
<212> TYPE: DNA
<213> ORGANISM: Artificial Sequence
<220> FEATURE:
<223> OTHER INFORMATION: COMPLETELY ARTIFICIAL

<400> SEQUENCE: 16
ttaggtaccc tatctcaatg catgt 25

<210> SEQ ID NO 17
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 17
taacacctgc agtcctgtag tagaaacaag gtcgt 35

<210> SEQ ID NO 18
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 18
ttacacctgc gactggggag cgaaagcagg tcaat 35

<210> SEQ ID NO 19

-continued

<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 19
taacacctgc agtcctgtag tagaaacaag gcatt 35

<210> SEQ ID NO 20
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 20
ttacacctgc gactggggag cgaaagcagg caaac 35

<210> SEQ ID NO 21
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 21
taacgtctct ctgtagtaga aacaaggtac t 31

<210> SEQ ID NO 22
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 22
ttacgtctct ggggagcgaa agcaggtact g 31

<210> SEQ ID NO 23
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 23
taacgtctct ctgtagtaga aacaagggta t 31

<210> SEQ ID NO 24
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 24
ttacgtctct ggggagcaaa agcagggtag a 31

<210> SEQ ID NO 25
<211> LENGTH: 30
<212> TYPE: DNA
<213> ORGANISM: Artificial Sequence
<220> FEATURE:
<223> OTHER INFORMATION: COMPLETELY ARTIFICIAL

<400> SEQUENCE: 25
taacgtctct ctgtagtaga aacaagggtg 30

<210> SEQ ID NO 26
<211> LENGTH: 30
<212> TYPE: DNA
<213> ORGANISM: Artificial Sequence
<220> FEATURE:
<223> OTHER INFORMATION: COMPLETELY ARTIFICIAL

<400> SEQUENCE: 26
ttacgtctct ggggagcaaa agcaggggaa 30

<210> SEQ ID NO 27
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 27
taacacctgc agtcctgtag tagaaacaag gagtt 35

<210> SEQ ID NO 28
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 28
ttacacctgc gactggggag cgaaagcagg agttt 35

<210> SEQ ID NO 29
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 29
taacgtctct ctgtagtaga aacaaggtag t 31

<210> SEQ ID NO 30
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 30
ttacgtctct ggggagcaaa agcaggtaga t 31

<210> SEQ ID NO 31
<211> LENGTH: 31
<212> TYPE: DNA
<213> ORGANISM: Artificial Sequence
<220> FEATURE:
<223> OTHER INFORMATION: COMPLETELY ARTIFICIAL

<400> SEQUENCE: 31
taacgtctct ctgtagtaga aacaagggtg t 31

<210> SEQ ID NO 32
<211> LENGTH: 31
<212> TYPE: DNA

-continued

<213> ORGANISM: Artificial Sequence
<220> FEATURE:
<223> OTHER INFORMATION: COMPLETELY ARTIFICIAL

<400> SEQUENCE: 32
ttacgtctct ggggagcaaa agcagggtga c 31

<210> SEQ ID NO 33
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 33
taagcccggg cgttgacatt gattattg 28

<210> SEQ ID NO 34
<211> LENGTH: 37
<212> TYPE: DNA
<213> ORGANISM: Artificial Sequence
<220> FEATURE:
<223> OTHER INFORMATION: COMPLETELY ARTIFICIAL

<400> SEQUENCE: 34
ttagccggct tagcggccgc catagagccc accgcat 37

<210> SEQ ID NO 35
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 35
taagcgcgcg ttgacattga ttattgac 28

<210> SEQ ID NO 36
<211> LENGTH: 37
<212> TYPE: DNA
<213> ORGANISM: Artificial Sequence
<220> FEATURE:
<223> OTHER INFORMATION: COMPLETELY ARTIFICIAL

<400> SEQUENCE: 36
ttagccggct tacctgcagg ccatagagcc caccgca 37

<210> SEQ ID NO 37
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 37
taaggtaccg ttgacattga ttattgac 28

<210> SEQ ID NO 38
<211> LENGTH: 37
<212> TYPE: DNA
<213> ORGANISM: Artificial Sequence
<220> FEATURE:
<223> OTHER INFORMATION: COMPLETELY ARTIFICIAL

<400> SEQUENCE: 38
ttagccggct tattaattaa ccatagagcc caccgca 37

<210> SEQ ID NO 39
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 39
taagggcccg ttgacattga ttattgac 28

<210> SEQ ID NO 40
<211> LENGTH: 37
<212> TYPE: DNA
<213> ORGANISM: Artificial Sequence
<220> FEATURE:
<223> OTHER INFORMATION: COMPLETELY ARTIFICIAL

<400> SEQUENCE: 40
ttagccggct tacacgtgcc atagagccca ccgcatc 37

<210> SEQ ID NO 41
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 41
taacacgtgg tgtcgcccgg agtactgg 28

<210> SEQ ID NO 42
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 42
ttagccggct cggtcgcttc gcggaggt 28

<210> SEQ ID NO 43
<211> LENGTH: 28
<212> TYPE: DNA
<213> ORGANISM: Artificial Sequence
<220> FEATURE:
<223> OTHER INFORMATION: COMPLETELY ARTIFICIAL

<400> SEQUENCE: 43
taattaatta agtgtcgccc ggagtact 28

<210> SEQ ID NO 44
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 44
ttagccggct tagggccctc ggtcgcttcg cggag 35

<210> SEQ ID NO 45
<211> LENGTH: 28
<212> TYPE: DNA
<213> ORGANISM: Artificial Sequence
<220> FEATURE:

<223> OTHER INFORMATION: COMPLETELY ARTIFICIAL

<400> SEQUENCE: 45
taacctgcag ggtgtcgccc ggagtact 28

<210> SEQ ID NO 46
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 46
ttagccggct taggtacctc ggtcgcttcg cggag 35

<210> SEQ ID NO 47
<211> LENGTH: 28
<212> TYPE: DNA
<213> ORGANISM: Artificial Sequence
<220> FEATURE:
<223> OTHER INFORMATION: COMLETELY ARTIFICIAL

<400> SEQUENCE: 47
taagcggccg cgtgtcgccc ggagtact 28

<210> SEQ ID NO 48
<211> LENGTH: 35
<212> TYPE: DNA
<213> ORGANISM: Artificial Sequence
<220> FEATURE:
<223> OTHER INFORMATION: COMPLETELY ARTIFICIAL

<400> SEQUENCE: 48
ttagccggct tagcgcgctc ggtcgcttcg cggag 35

<210> SEQ ID NO 49
<211> LENGTH: 2341
<212> TYPE: DNA
<213> ORGANISM: Influenza A virus

<400> SEQUENCE: 49
agcgaaagca ggtcaattat attcaatatg gaaagaataa aagaactaag gaatctaatg 60
tcgcagtctc gcactcgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcagggac aaactttatg gagtaaaatg aatgacgccg gatcagaccg agtgatggta 300
tcacctctgg ctgtgacatg gtggaatagg aatggaccag tgacaagtac agttcattat 360
ccaaaaatct acaaaactta ttttgaaaaa gtcgaaaggt taaaacatgg aacctttggc 420
cctgtccatt ttagaaacca agtcaaaata cgtcgaagag ttgacataaa tcctggtcat 480
gcagatctca gtgccaaaga ggcacaggat gtaatcatgg aagttgtttt ccctaacgaa 540
gtgggagcca ggatactaac atcggaatcg caactaacga caaccaaaga gaagaaagaa 600
gaactccagg gttgcaaaat ttctcctctg atggtggcat acatgttgga gagagaactg 660
gtccgcaaaa cgagattcct cccagtggct ggtggaacaa gcagtgtgta cattgaagtg 720
ttgcatttga cccaaggaac atgctgggaa cagatgtaca ctccaggagg ggaggcgagg 780
aatgatgatg ttgatcaaag cttaattatt gctgctagaa acatagtaag aagagccaca 840
gtatcagcag atccactagc atctttattg gagatgtgcc acagcacgca gattggtgga 900
ataaggatgg taaacatcct taggcagaac ccaacagaag agcaagccgt ggatatttgc 960
aaggctgcaa tgggactgag aattagctca tccttcagtt ttggtggatt cacatttaag 1020
agaacaagcg gatcatcagt caagagagag gaagaggtgc ttacgggcaa tcttcagaca 1080
ttgaagataa gagtacatga gggatatgaa gagttcacaa tggttgggag aagagcaaca 1140
gctatactca gaaaagcaac caggagattg attcagctga tagtgagtgg gagagacgaa 1200
cagtcgattg ccgaagcaat aattgtggcc atggtatttt cacaagagga ttgtatgata 1260
aaagcagtta gaggtgacct gaatttcgtc aatagggcga atcagcgatt gaatcccatg 1320
caccaacttt tgagacattt tcagaaggat gcaaaggtgc tctttcaaaa ttggggaatt 1380
gaatccatcg acaatgtgat gggaatgatc gggatattgc ccgacatgac tccaagcacc 1440
gagatgtcaa tgagaggagt gagaatcagc aaaatggggg tagatgagta ttccagcgcg 1500
gagaagatag tggtgagcat tgaccgtttt ttgagagtta gggaccaacg tgggaatgta 1560
ctactgtctc ccgaggagat cagtgaaaca cagggaacag agaaactgac aataacttac 1620
tcatcgtcaa tgatgtggga gattaatggt cctgaatcag tgttggtcaa tacctatcag 1680
tggatcatca gaaactggga aactgttaaa attcagtggt cccagaatcc tacaatgctg 1740
tacaataaaa tggaatttga gccatttcag tctttagttc caaaggccgt tagaggccaa 1800
tacagtgggt ttgtgagaac tctgttccaa caaatgaggg atgtgcttgg gacatttgat 1860
accgctcaga taataaaact tcttcccttc gcagccgctc caccaaagca aagtagaacg 1920
cagttctcct cattgactat aaatgtgagg ggatcaggaa tgagaatact tgtaaggggc 1980
aattctccag tattcaacta caacaagacc actaaaagac tcacagttct cggaaaggat 2040
gctggccctt taactgaaga cccagatgaa ggcacagctg gagttgagtc cgcagttctg 2100
agaggattcc tcattctggg caaagaagac aggagatatg gaccagcatt aagcataaat 2160
gaactgagca accttgcgaa aggagagaag gctaatgtgc taattgggca aggagacgtg 2220
gtgttggtaa tgaaacggaa acggaactct agcatactta ctgacagcca gacagcgacc 2280
aaaagaattc ggatggccat caattagtgt cgaatagttt aaaaacgacc ttgtttctac 2340
t 2341

<210> SEQ ID NO 50
<211> LENGTH: 2341
<212> TYPE: DNA
<213> ORGANISM: Influenza A virus

<400> SEQUENCE: 50
agcgaaagca ggcaaaccat ttgaatggat gtcaatccga ctttactttt cttaaaagtg 60
ccagcacaaa atgctataag cacaactttc ccttatactg gagaccctcc ttacagccat 120
gggacaggaa caggatacac catggatact gtcaacagga cacatcagta ctcagaaagg 180
ggaagatgga caacaaacac cgaaactgga gcaccgcaac tcaacccgat tgatgggcca 240
ctgccagaag acaatgaacc aagtggttat gcccaaacag attgtgtatt ggaagcaatg 300
gccttccttg aggaatccca tcctggtatc tttgagacct cgtgtcttga aacgatggag 360
gttgttcagc aaacacgagt ggacaagctg acacaaggcc gacagaccta tgactggact 420
ctaaatagga accagcctgc tgcaacagca ttggccaaca caatagaagt gttcagatca 480
aatggcctca cggccaatga atctggaagg ctcatagact tccttaagga tgtaatggag 540
tcaatgaaca aagaagaaat ggagatcaca actcattttc agagaaagag acgagtgaga 600

-continued

```
gacaatatga ctaagaaaat ggtgacacag agaacaatag gtaaaaggaa gcagagattg    660
aacaaaagga gttatctaat tagggcatta accctgaaca caatgaccaa agatgctgag    720
agagggaagc taaaacggag agcaattgca accccaggga tgcaaataag gggtttgta    780
tactttgttg agacactagc aaggagtata tgtgagaaac ttgaacaatc aggattgcca    840
gttggaggca atgagaagaa agcaaagttg gcaaatgttg taaggaagat gatgaccaat    900
tctcaggaca ctgaaatttc tttcaccatc actggagata acaccaaatg gaacgaaaat    960
cagaaccctc ggatgttttt ggccatgatc acatatataa ccagaaatca gcccgaatgg   1020
ttcagaaatg ttctaagtat tgctccaata atgttctcaa acaaaatggc gagactggga   1080
aaggggtaca tgtttgagag caagagtatg aaaattagaa ctcaaatacc tgcagaaatg   1140
ctagcaagca tcgatttgaa atacttcaat gattcaacta gaaagaagat tgaaaaaatc   1200
cggccgctct taatagatgg gactgcatca ttgagccctg gaatgatgat gggcatgttc   1260
aatatgttaa gtactgtatt aggcgtctcc atcctgaatc ttggacaaaa gagacacacc   1320
aagactactt actggtggga tggtcttcaa tcttctgatg attttgctct gattgtgaat   1380
gcacccaatc atgaagggat tcaagccgga gtcaacaggt tttatcgaac ctgtaagcta   1440
cttggaatta atatgagcaa gaaaaagtct tacataaaca gaacaggtac atttgaattc   1500
acaagttttt tctatcgtta tgggtttgtt gccaatttca gcatggagct tcccagcttt   1560
ggggtgtctg ggatcaacga gtctgcggac atgagtattg gagttactgt catcaaaaac   1620
aatatgataa acaatgatct tggtccagca accgctcaaa tggcccttca gctgttcatc   1680
aaagattaca ggtacacgta ccggtgccat agaggtgaca cacaaataca aacccgaaga   1740
tcatttgaaa taaagaaact gtgggagcaa acccattcca aagctggact gctggtctcc   1800
gacggaggcc caaatttata caacattaga aatctccaca ttcctgaagt ctgcttgaaa   1860
tgggaattaa tggatgagga ttaccagggg cgtttatgca acccactgaa cccatttgtc   1920
aaccataaag acattgaatc agtgaacaat gcagtgataa tgccagcaca tggtccagcc   1980
aaaaacatgg agtatgatgc tgttgcaaca acacactcct ggatccccaa aagaaatcga   2040
tccatcttga atacaagcca aagaggaata cttgaagatg aacaaatgta ccaaaagtgc   2100
tgcaacttat ttgaaaaatt cttccccagc agttcataca gaagaccagt cgggatatcc   2160
agtatggtgg aggctatggt ttccagagcc cgaattgatg cacgaattga tttcgaatct   2220
ggaaggataa agaaagagga gttcactgag atcatgaaga tctgttccac cattgaagag   2280
ctcagacggc aaaaatagtg aatttagctt gtccttcatg aaaaaatgcc ttgtttctac   2340
t                                                                   2341
```

<210> SEQ ID NO 51
<211> LENGTH: 2233
<212> TYPE: DNA
<213> ORGANISM: Influenza A virus

<400> SEQUENCE: 51

```
agcgaaagca ggtactgatt caaaatggaa gattttgtgc gacaatgctt caatccgatg     60
attgtcgagc ttgcggaaaa ggcaatgaaa gagtatggag aggacctgaa aatcgaaaca    120
aacaaatttg cagcaatatg cactcacttg gaagtgtgct tcatgtattc agattttcac    180
ttcatcgatg agcaaggcga gtcaatagtc gtagaacttg gcgatccaaa tgcacttttg    240
aagcacagat ttgaaataat cgagggaaga gatcgcacaa tagcctggac agtaataaac    300
agtatttgca acactacagg ggctgagaaa ccaaagtttc taccagattt gtatgattac    360
```

```
aagaagaata gattcatcga aattggagta acaaggagag aagttcacat atactatctg    420
gaaaaggcca ataaaattaa atctgagaag acacacatcc acattttctc attcactggg    480
gaggaaatgg ccacaaaggc cgactacact ctcgatgaag aaagcagggc taggatcaaa    540
accaggctat tcaccataag acaagaaatg gctagcagag gcctctggga ttcctttcgt    600
cagtccgaga gaggcgaaga gacaattgaa gaaagatttg aaatcacagg aacaatgcgc    660
aagcttgccg accaaagtct cccgccaaac ttctccagcc ttgaaaaatt tagagcctat    720
gtggatggat tcgaaccgaa cggctacatt gagggcaagc tttctcaaat gtccaaagaa    780
gtaaatgcta gaattgaacc tttttgaaa tcaacaccac gaccacttag acttccggat     840
gggcctccct gttctcagcg gtccaaattc ctgctgatgg atgccttaaa attaagcatt    900
gaggacccaa gtcatgaggg agaggggata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa ggactaaaaa tatgaagaaa acgagtcagt taaagtgggc acttggtgag   1140
aacatggcac cagaaaaggt agactttgac gattgtaaag atgtaggcga tttgaagcaa   1200
tatgatagtg atgaaccaga attgaggtcg cttgcaagtt ggattcagaa tgagttcaac   1260
aaggcatgtg aactgaccga ttcaagctgg atagagctcg atgagattgg agaagatgcg   1320
gctccaattg aacacattgc aagcatgaga aggaattatt tcacagcaga ggtgtctcat   1380
tgcagagcca cagaatacat aatgaagggg gtgtacatca atactgcctt gcttaatgca   1440
tcctgtgcag caatggatga tttccaatta attccaatga taagcaagtg tagaactaag   1500
gagggaaggc gaaagaccaa tttgtacggt ttcatcataa aaggaagatc ccacttaagg   1560
aatgacaccg atgtggtaaa ctttgtgagc atggagtttt ccctcactga cccaagactt   1620
gaaccacaca aatgggagaa gtactgtgtt cttgaggtag gagatatgct tctaagaagt   1680
gccataggcc atgtgtcaag gcctatgttc ttgtatgtga ggacaaatgg aacctcaaaa   1740
attaaaatga aatgggggat ggaaatgagg cgttgcctcc ttcagtcact tcaacaaatc   1800
gagagtatga ttgaagctga gtcctctgtc aaggagaaag acatgaccaa agagttcttt   1860
gaaaacaaat cagaaacatg gcccgttgga gagtccccca aaggagtgga ggaaggttcc   1920
attgggaagg tctgcagaac tttattggca aagtcggtat tcaacagctt gtatgcatct   1980
ccacaactag aaggattttc agctgaatca agaaaactgc ttcttatcgt tcaggctctt   2040
agggacaacc tggaacctgg gacctttgat cttgggggc tatatgaagc aattgaggag    2100
tgcctgatta atgatccctg ggttttgctt aatgcttctt ggttcaactc cttcctcaca   2160
catgcattga gatagttgtg gcaatgctac tatttgctat ccatactgtc caaaaaagta   2220
ccttgtttct act                                                      2233
```

<210> SEQ ID NO 52
<211> LENGTH: 1565
<212> TYPE: DNA
<213> ORGANISM: Influenza A virus

<400> SEQUENCE: 52

```
agcaaaagca gggtagataa tcactcacag agtgacatcg aaatcatggc gaccaaaggc     60
accaaacgat cttacgaaca gatggagact gatggagaac gccagaatgc cactgaaatc    120
agagcatctg tcggaaaaat gattgatgga attggacgat tctacatcca aatgtgcacc    180
```

-continued gaacttaaac tcagtgatta tgagggacgg ctgattcaga acagcttaac aatagagaga 240
atggtgctct ctgcttttga cgagaggagg aataaatatc tagaagaaca tcccagtgcg 300
gggaaagatc ctaagaaaac tggaggacct atatacagga gagtagatgg aaagtggagg 360
agagaactca tcctttatga caaagaagaa ataagacgaa tctggcgcca agctaataat 420
ggtgacgatg caacggctgg tctgactcac atgatgatct ggcactccaa tttgaatgat 480
gcaacttacc agaggacaag agctcttgtt cgcacaggaa tggatcccag gatgtgctca 540
ctgatgcagg gttcaaccct ccctaggagg tctggggccg caggtgctgc agtcaaagga 600
gttggaacaa tggtgatgga attgatcaga atgatcaaac gtgggatcaa tgatcggaac 660
ttctggaggg gtgagaatgg acggagaaca aggattgctt atgaaagaat gtgcaacatt 720
ctcaaaggga aatttcaaac agctgcacaa agaacaatgg tggatcaagt gagagagagc 780
cggaatccag gaaatgctga gttcgaagat ctcatctttt tagcacggtc tgcactcata 840
ttgagagggt cagttgctca caagtcctgc ctgcctgcct gtgtgtatgg atctgccgta 900
gccagtggat acgactttga aagagaggga tactctctag tcggaataga ccctttcaga 960
ctgcttcaaa acagccaagt atacagccta atcagaccaa atgagaatcc agcacacaag 1020
agtcaactgg tgtggatggc atgccattct gctgcatttg aagatctaag agtatcaagc 1080
ttcatcagag ggacgaaagt ggtcccaaga gggaagcttt ccactagagg agttcaaatt 1140
gcttccaatg aaaacatgga gactatggaa tcaagtaccc ttgaactgag aagcagatac 1200
tgggccataa ggaccagaag tggagggaac accaatcaac agagggcttc ctcgggccaa 1260
atcagcatac aacctacgtt ctcagtacag agaaatctcc cttttgacag accaaccatt 1320
atggcagcat tcactgggaa tacagagggg agaacatctg acatgagaac cgaaatcata 1380
aggctgatgg aaagtgcaag accagaagat gtgtctttcc aggggcgggg agtcttcgag 1440
ctctcggacg aaaaggcaac gagcccgatc gtgccctcct ttgacatgag taatgaagga 1500
tcttatttct tcggagacaa tgcagaggag tacgacaatt aaagaaaaat acccttgttt 1560
ctact 1565

<210> SEQ ID NO 53
<211> LENGTH: 1775
<212> TYPE: DNA
<213> ORGANISM: Influenza A virus

<400> SEQUENCE: 53
agcaaaagca ggggaaaata aaaacaacca aaatgaaggc aaaactactg gtcctgttat 60
atgcatttgt agctacagat gcagacacaa tatgtatagg ctaccatgcg aacaactcaa 120
ccgacactgt tgacacaata ctcgagaaga atgtggcagt gacacattct gttaacctgc 180
tcgaagacag ccacaacggg aaactatgta aattaaaagg aatagcccca ctacaattgg 240
ggaaatgtaa catcaccgga tggctcttgg gaaatccaga atgcgactca ctgcttccag 300
cgagatcatg gtcctacatt gtagaaacac caaactctga gaatggagca tgttatccag 360
gagatctcat cgactatgag gaactgaggg agcaattgag ctcagtatca tcattagaaa 420
gattcgaaat atttcccaag gaaagttcat ggcccaacca cacattcaac ggagtaacag 480
tatcatgctc ccatagggga aaaagcagtt tttacagaaa tttgctatgg ctgacgaaga 540
agggggattc atacccaaag ctgaccaatt cctatgtgaa caataaaggg aaagaagtcc 600
ttgtactatg gggtgttcat cacccgtcta gcagtgatga gcaacagagt ctctatagta 660
atggaaatgc ttatgtctct gtagcgtctt caaattataa caggagattc accccggaaa 720
tagctgcaag gcccaaagta agagatcaac atgggaggat gaactattac tggaccttgc 780
tagaacccgg agacacaata atatttgagg caactggtaa tctaatagca ccatggtatg 840
ctttcgcact gagtagaggg tttgagtccg gcatcatcac ctcaaacgcg tcaatgcatg 900
agtgtaacac gaagtgtcaa acaccccagg gagctataaa cagcaatctc cctttccaga 960
atatacaccc agtcacaata ggagagtgcc caaaatatgt caggagtacc aaattgagga 1020
tggttacagg actaagaaac atcccatcca ttcaatacag aggtctattt ggagccattg 1080
ctggttttat tgaggggga tggactggaa tgatagatgg atggtatggt tatcatcatc 1140
agaatgaaca gggatcaggc tatgcagcgg atcaaaaaag cacacaaaat gccattaacg 1200
ggattacaaa caaggtgaac tctgttatcg agaaaatgaa cactcaattc acagctgtgg 1260
gtaaagaatt caacaactta gaaaaaagga tggaaaattt aaataaaaaa gttgatgatg 1320
ggtttctgga catttggaca tataatgcag aattgttagt tctactggaa aatgaaagga 1380
ctttggattt ccatgactta aatgtgaaga atctgtacga gaaagtaaaa agccaattaa 1440
agaataatgc caaagaaatc ggaaatgggt gttttgagtt ctaccacaag tgtgacaatg 1500
aatgcatgga aagtgtaaga aatgggactt atgattatcc aaaatattca gaagaatcaa 1560
agttgaacag ggaaaagata gatggagtga aattggaatc aatgggggtg tatcagattc 1620
tggcgatcta ctcaactgtc gccagttcac tggtgctttt ggtctccctg ggggcaatca 1680
gtttctggat gtgttctaat gggtctttgc agtgcagaat atgcatctga gattaggatt 1740
tcagaaatat aaggaaaaac acccttgttt ctact 1775

<210> SEQ ID NO 54
<211> LENGTH: 1409
<212> TYPE: DNA
<213> ORGANISM: Influenza A virus

<400> SEQUENCE: 54
agcgaaagca ggagtttaaa tgaatccaaa ccagaaaata ataaccattg ggtcaatctg 60
tatggtagtc ggaataatta gcctaatatt gcaaatagga aatataatct caatatggat 120
tagccattca attcaaaccg gaaatcaaaa ccatactgga atatgcaacc aaggcagcat 180
tacctataaa gttgttgctg ggcaggactc aacttcagtg atattaaccg gcaattcatc 240
tctttgtccc atccgtgggt gggctataca cagcaaagac aatggcataa gaattggttc 300
caaaggagac gtttttgtca taagagagcc ttttatttca tgttctcact tggaatgcag 360
gacctttttt ctgactcaag gcgccttact gaatgacaag cattcaaggg ggacctttaa 420
ggacagaagc ccttataggg ccttaatgag ctgccctgtc ggtgaagctc cgtccccgta 480
caattcaagg tttgaatcgg ttgcttggtc agcaagtgca tgtcatgatg gaatgggctg 540
gctaacaatc ggaatttctg gtccagatga tggagcagtg gctgtattaa aatacaaccg 600
cataataact gaaaccataa aaagttggag gaagaatata ttgagaacac aagagtctga 660
atgtacctgt gtaaatggtt catgttttac cataatgacc gatggcccaa gtgatgggct 720
ggcctcgtac aaaattttca agatcgagaa ggggaaggtt actaaatcga tagagttgaa 780
tgcacctaat tctcactacg aggaatgttc ctgttaccct gataccggca aagtgatgtg 840
tgtgtgcaga gacaattggc acggttcgaa ccgaccatgg gtgtccttcg accaaaacct 900
agattataaa ataggataca tctgcagtgg ggttttcggt gacaacccgc gtcccaaaga 960
tggaacaggc agctgtggcc cagtgtctgc tgatggagca aacggagtaa agggatttc 1020

-continued atataagtat ggcaatggtg tttggatagg aaggactaaa agtgacagtt ccagacatgg 1080
gtttgagatg atttgggatc ctaatggatg gacagagact gatagtaggt tctctatgag 1140
acaagatgtt gtggcaataa ctaatcggtc agggtacagc ggaagtttcg ttcaacatcc 1200
tgagctaaca gggctagact gtatgaggcc ttgcttctgg gttgaattaa tcagggggct 1260
acctgaggag gacgcaatct ggactagtgg gagcatcatt tctttttgtg gtgtgaatag 1320
tgatactgta gattggtctt ggccagacgg tgctgagttg ccgttcacca ttgacaagta 1380
gtttgttcaa aaaactcctt gtttctact 1409

<210> SEQ ID NO 55
<211> LENGTH: 1027
<212> TYPE: DNA
<213> ORGANISM: Influenza A virus

<400> SEQUENCE: 55
agcaaaagca ggtagatatt gaaagatgag tcttctaacc gaggtcgaaa cgtacgttct 60
ctctatcgtc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
gggactgcag cgtagacgct ttgtccaaaa tgctcttaat gggaacggag atccaaataa 300
catggacaaa gcagttaaac tgtataggaa gcttaagagg gagataacat tccatggggc 360
caaagaaata gcactcagtt attctgctgg tgcacttgcc agttgtatgg gcctcatata 420
caacaggatg gggggctgtga ccactgaagt ggcatttggc ctggtatgcg caacctgtga 480
acagattgct gactcccagc atcggtctca taggcaaatg gtgacaacaa ccaatccact 540
aatcagacat gagaacagaa tggttctagc cagcactaca gctaaggcta tggagcaaat 600
ggctggatcg agtgagcaag cagcagaggc catggatatt gctagtcagg ccaggcaaat 660
ggtgcaggcg atgagaaccg ttgggactca tcctagctcc agtgctggtc taaaagatga 720
tcttcttgaa aatttgcagg cctatcagaa acgaatgggg gtgcagatgc aacgattcaa 780
gtgatcctct cgtcattgca gcaaatatca ttggaatctt gcacttgata ttgtggattc 840
ttgatcgtct ttttttcaaa tgcatttatc gtcgctttaa atacggtttg aaaagagggc 900
cttctacgga aggagtgcca gagtctatga gggaagaata tcgaaaggaa cagcagaatg 960
ctgtggatgt tgacgatggt cattttgtca acatagagct ggagtaaaaa actaccttgt 1020
ttctact 1027

<210> SEQ ID NO 56
<211> LENGTH: 890
<212> TYPE: DNA
<213> ORGANISM: Influenza A virus

<400> SEQUENCE: 56
agcaaaagca gggtgacaaa gacataatgg atccaaacac tgtgtcaagc tttcaggtag 60
attgctttct ttggcatgtc cgcaaaagag ttgcagacca agaactaggt gatgccccat 120
tccttgatcg gcttcgccga gatcagaagt ccctaagagg aagaggcagc actcttggtc 180
tggacatcga aacagccacc cgtgctggaa agcaaatagt ggagcggatt ctgaaggaag 240
aatctgatga ggcactcaaa atgaccatgg cctctgtacc tgcatcgcgc tacctaactg 300
acatgactct tgaggaaatg tcaaggcact ggttcatgct catgcccaag cagaaagtgg 360
caggccctct ttgtatcaga atggaccagg cgatcatgga taagaacatc atactgaaag 420

```
cgaacttcag tgtgattttt gaccggctgg agactctaat attactaagg gccttcaccg    480

aagaggggac aattgttggc gaaatttcac cactgccctc tcttccagga catactgatg    540

aggatgtcaa aaatgcagtt ggggtcctca tcggaggact tgaatggaat aataacacag    600

ttcgagtctc tgaaactcta cagagattcg cttggagaag cagtaatgag aatgggagac    660

ctccactcac tccaaaacag aaacggaaaa tggcgggaac aattaggtca gaagtttgaa    720

gaaataagat ggttgattga agaagtgaga cacagactga agataacaga gaatagtttt    780

gagcaaataa catttatgca agccttacaa ctattgcttg aagtggagca agagataaga    840

actttctcgt ttcagcttat ttaataataa aaaacaccct tgtttctact              890
```

```
<210> SEQ ID NO 57
<211> LENGTH: 5833
<212> TYPE: DNA
<213> ORGANISM: Artificial Sequence
<220> FEATURE:
<223> OTHER INFORMATION: COMPLETELY ARTIFICIAL

<400> SEQUENCE: 57
```

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtgtcgcccg gagtactggt cgacctccga agttgggggg gagcagcagg tggtaccacc    960

tgctcctaca gacgaacata taaggcatcc gaaaaaaacg ttctagtccc ataggcgccg   1020

actaccggca gcggctccga cggcagccga ggtttacctc gacgtaactg gaggtacaaa   1080

attacagcga cgcctctggc agctccggag ctgtagcgcc cccccccaca gccagagcgg   1140

ccaagacaat ccgaaacggg gtagacctgg acgcggatcg caagccgccc cggcagcgac   1200

ctctagccgc cgccgcggag agcgcgagac ggtagcaccc gggtagaccg ttccgccgtt   1260

tccgagacgc cccggcagcg acccctagcc gccgccgccg cggagagacc gagccggacg   1320

gtgcccgccg ggaccaggta gaccgttccg ccgtgcccca gccacctccg cgaagcgacc   1380

gaaagggcga attctgcaga aagcttaagt ttaaaccgct gatcagcctc gactgtgcct   1440

tctagttgcc agccatctgt tgtttgcccc tcccccgtgc cttccttgac cctggaaggt   1500

gccactccca ctgtcctttc ctaataaaat gaggaaattg catcgcattg tctgagtagg   1560
```

-continued

```
tgtcattcta ttctgggggg tggggtgggg caggacagca agggggagga ttgggaagac   1620
aatagcaggc atgctgggga tgcggtgggc tctatggctt ctgaggcgga aagaaccagc   1680
tggggctcta gggggtatcc ccacgcgccc tgtagcggcg cattaagcgc ggcgggtgtg   1740
gtggttacgc gcagcgtgac cgctacactt gccagcgccc tagcgcccgc tcctttcgct   1800
ttcttccctt cctttctcgc cacgttcgcc ggctttcccc gtcaagctct aaatcggggg   1860
ctccctttag ggttccgatt tagtgcttta cggcacctcg accccaaaaa acttgattag   1920
ggtgatggtt cacgtagtgg gccatcgccc tgatagacgg tttttcgccc tttgacgttg   1980
gagtccacgt tctttaatag tggactcttg ttccaaactg gaacaacact caaccctatc   2040
tcggtctatt cttttgattt ataagggatt ttgccgattt cggcctattg gttaaaaaat   2100
gagctgattt aacaaaaatt taacgcgaat taattctgtg gaatgtgtgt cagttagggt   2160
gtggaaagtc cccaggctcc ccagcaggca gaagtatgca aagcatgcat ctcaattagt   2220
cagcaaccag gtgtggaaag tccccaggct ccccagcagg cagaagtatg caaagcatgc   2280
atctcaatta gtcagcaacc atagtcccgc ccctaactcc gcccatcccg cccctaactc   2340
cgcccagttc cgcccattct ccgccccatg gctgactaat tttttttatt tatgcagagg   2400
ccgaggccgc ctctgcctct gagctattcc agaagtagtg aggaggcttt tttggaggcc   2460
taggcttttg caaaaagctc ccgggagctt gtatatccat tttcggatct gatcaagaga   2520
caggatgagg atcgtttcgc atgattgaac aagatggatt gcacgcaggt tctccggccg   2580
cttgggtgga gaggctattc ggctatgact gggcacaaca gacaatcggc tgctctgatg   2640
ccgccgtgtt ccggctgtca gcgcaggggc gcccggttct ttttgtcaag accgacctgt   2700
ccggtgccct gaatgaactg caggacgagg cagcgcggct atcgtggctg gccacgacgg   2760
gcgttccttg cgcagctgtg ctcgacgttg tcactgaagc gggaagggac tggctgctat   2820
tgggcgaagt gccggggcag gatctcctgt catctcacct tgctcctgcc gagaaagtat   2880
ccatcatggc tgatgcaatg cggcggctgc atacgcttga tccggctacc tgcccattcg   2940
accaccaagc gaaacatcgc atcgagcgag cacgtactcg gatggaagcc ggtcttgtcg   3000
atcaggatga tctggacgaa gagcatcagg ggctcgcgcc agccgaactg ttcgccaggc   3060
tcaaggcgcg catgcccgac ggcgaggatc tcgtcgtgac ccatggcgat gcctgcttgc   3120
cgaatatcat ggtggaaaat ggccgctttt ctggattcat cgactgtggc cggctgggtg   3180
tggcggaccg ctatcaggac atagcgttgg ctacccgtga tattgctgaa gagcttggcg   3240
gcgaatgggc tgaccgcttc ctcgtgcttt acggtatcgc cgctcccgat tcgcagcgca   3300
tcgccttcta tcgccttctt gacgagttct tctgagcggg actctggggt tcgaaatgac   3360
cgaccaagcg acgcccaacc tgccatcacg agatttcgat tccaccgccg ccttctatga   3420
aaggttgggc ttcggaatcg ttttccggga cgccggctgg atgatcctcc agcgcgggga   3480
tctcatgctg gagttcttcg cccaccccaa cttgtttatt gcagcttata atggttacaa   3540
ataaagcaat agcatcacaa atttcacaaa taaagcattt ttttcactgc attctagttg   3600
tggtttgtcc aaactcatca atgtatctta tcatgtctgt ataccgtcga cctctagcta   3660
gagcttggcg taatcatggt catagctgtt tcctgtgtga aattgttatc cgctcacaat   3720
tccacacaac atacgagccg gaagcataaa gtgtaaagcc tggggtgcct aatgagtgag   3780
ctaactcaca ttaattgcgt tgcgctcact gcccgctttc cagtcgggaa acctgtcgtg   3840
ccagctgcat taatgaatcg gccaacgcgc ggggagaggc ggtttgcgta ttgggcgctc   3900
ttccgcttcc tcgctcactg actcgctgcg ctcggtcgtt cggctgcggc gagcggtatc   3960
```

agctcactca aaggcggtaa tacggttatc cacagaatca ggggataacg caggaaagaa 4020
catgtgagca aaaggccagc aaaaggccag gaaccgtaaa aaggccgcgt tgctggcgtt 4080
tttccatagg ctccgccccc ctgacgagca tcacaaaaat cgacgctcaa gtcagaggtg 4140
gcgaaacccg acaggactat aaagatacca ggcgtttccc cctggaagct ccctcgtgcg 4200
ctctcctgtt ccgaccctgc cgcttaccgg atacctgtcc gcctttctcc cttcgggaag 4260
cgtggcgctt tctcatagct cacgctgtag gtatctcagt tcggtgtagg tcgttcgctc 4320
caagctgggc tgtgtgcacg aaccccccgt tcagcccgac cgctgcgcct tatccggtaa 4380
ctatcgtctt gagtccaacc cggtaagaca cgacttatcg ccactggcag cagccactgg 4440
taacaggatt agcagagcga ggtatgtagg cggtgctaca gagttcttga agtggtggcc 4500
taactacggc tacactagaa gaacagtatt tggtatctgc gctctgctga agccagttac 4560
cttcggaaaa agagttggta gctcttgatc cggcaaacaa accaccgctg gtagcggttt 4620
ttttgtttgc aagcagcaga ttacgcgcag aaaaaaagga tctcaagaag atcctttgat 4680
cttttctacg gggtctgacg ctcagtggaa cgaaaactca cgttaaggga ttttggtcat 4740
gagattatca aaaaggatct tcacctagat ccttttaaat taaaaatgaa gttttaaatc 4800
aatctaaagt atatatgagt aaacttggtc tgacagttac caatgcttaa tcagtgaggc 4860
acctatctca gcgatctgtc tatttcgttc atccatagtt gcctgactcc ccgtcgtgta 4920
gataactacg atacgggagg gcttaccatc tggccccagt gctgcaatga taccgcgaga 4980
cccacgctca ccggctccag atttatcagc aataaaccag ccagccggaa gggccgagcg 5040
cagaagtggt cctgcaactt tatccgcctc catccagtct attaattgtt gccgggaagc 5100
tagagtaagt agttcgccag ttaatagttt gcgcaacgtt gttgccattg ctacaggcat 5160
cgtggtgtca cgctcgtcgt ttggtatggc ttcattcagc tccggttccc aacgatcaag 5220
gcgagttaca tgatccccca tgttgtgcaa aaaagcggtt agctccttcg gtcctccgat 5280
cgttgtcaga agtaagttgg ccgcagtgtt atcactcatg gttatggcag cactgcataa 5340
ttctcttact gtcatgccat ccgtaagatg cttttctgtg actggtgagt actcaaccaa 5400
gtcattctga gaatagtgta tgcggcgacc gagttgctct tgcccggcgt caatacggga 5460
taataccgcg ccacatagca gaactttaaa agtgctcatc attggaaaac gttcttcggg 5520
gcgaaaactc tcaaggatct taccgctgtt gagatccagt tcgatgtaac ccactcgtgc 5580
acccaactga tcttcagcat cttttacttt caccagcgtt tctgggtgag caaaaacagg 5640
aaggcaaaat gccgcaaaaa agggaataag ggcgacacgg aaatgttgaa tactcatact 5700
cttccttttt caatattatt gaagcattta tcagggttat tgtctcatga gcggatacat 5760
atttgaatgt atttagaaaa ataaacaaat aggggttccg cgcacatttc cccgaaaagt 5820
gccacctgac gtc 5833

<210> SEQ ID NO 58
<211> LENGTH: 5187
<212> TYPE: DNA
<213> ORGANISM: Artificial Sequence
<220> FEATURE:
<223> OTHER INFORMATION: COMPLETELY ARTIFICIAL

<400> SEQUENCE: 58
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120

-continued

```
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagcgtgtcg cccggagtac tggtcgacct ccgaagttgg gggggagcag    300
caggtggtac cacctgctcc tacagacgaa catataaggc atccgaaaaa aacgttctag    360
tcccataggc gccgactacc ggcagcggct ccgacggcag ccgaggttta cctcgacgta    420
actggaggta caaaattaca gcgacgcctc tggcagctcc ggagctgtag cgcccccccc    480
cacagccaga gcggccaaga caatccgaaa cggggtagac ctggacgcgg atcgcaagcc    540
gccccggcag cgacctctag ccgccgccgc ggagagcgcg agacggtagc acccgggtag    600
accgttccgc cgtttccgag acgccccggc agcgacccct agccgccgcc gccgcggaga    660
gaccgagccg gacggtgccc gccgggacca ggtagaccgt tccgccgtgc cccagccacc    720
tccgcgaagc gaccgaaagg gcgaattctg cagaaagctt aagtttaaac cgctgatcag    780
cctcgactgt gccttctagt tgccagccat ctgttgtttg cccctccccc gtgccttcct    840
tgaccctgga aggtgccact cccactgtcc tttcctaata aaatgaggaa attgcatcgc    900
attgtctgag taggtgtcat tctattctgg ggggtggggt ggggcaggac agcaaggggg    960
aggattggga agacaatagc aggcatgctg gggatgcggt gggctctatg gcttctgagg   1020
cggaaagaac cagctggggc tctagggggt atccccacgc gccctgtagc ggcgcattaa   1080
gcgcggcggg tgtggtggtt acgcgcagcg tgaccgctac acttgccagc gccctagcgc   1140
ccgctccttt cgctttcttc ccttcctttc tcgccacgtt cgccggcttt ccccgtcaag   1200
ctctaaatcg ggggctccct ttagggttcc gatttagtgc tttacggcac ctcgacccca   1260
aaaaacttga ttagggtgat ggttcacgta gtgggccatc gccctgatag acggtttttc   1320
gccctttgac gttggagtcc acgttcttta atagtggact cttgttccaa actggaacaa   1380
cactcaaccc tatctcggtc tattcttttg atttataagg gattttgccg atttcggcct   1440
attggttaaa aaatgagctg atttaacaaa aatttaacgc gaattaattc tgtggaatgt   1500
gtgtcagtta gggtgtggaa agtccccagg ctccccagca ggcagaagta tgcaaagcat   1560
gcatctcaat tagtcagcaa ccaggtgtgg aaagtcccca ggctccccag caggcagaag   1620
tatgcaaagc atgcatctca attagtcagc aaccatagtc ccgcccctaa ctccgcccat   1680
cccgccccta actccgccca gttccgccca ttctccgccc catggctgac taattttttt   1740
tatttatgca gaggccgagg ccgcctctgc ctctgagcta ttccagaagt agtgaggagg   1800
ctttttttgga ggcctaggct tttgcaaaaa gctcccggga gcttgtatat ccattttcgg   1860
atctgatcaa gagacaggat gaggatcgtt tcgcatgatt gaacaagatg gattgcacgc   1920
aggttctccg gccgcttggg tggagaggct attcggctat gactgggcac aacagacaat   1980
cggctgctct gatgccgccg tgttccggct gtcagcgcag gggcgcccgg ttctttttgt   2040
caagaccgac ctgtccggtg ccctgaatga actgcaggac gaggcagcgc ggctatcgtg   2100
gctggccacg acgggcgttc cttgcgcagc tgtgctcgac gttgtcactg aagcgggaag   2160
ggactggctg ctattgggcg aagtgccggg gcaggatctc ctgtcatctc accttgctcc   2220
tgccgagaaa gtatccatca tggctgatgc aatgcggcgg ctgcatacgc ttgatccggc   2280
tacctgccca ttcgaccacc aagcgaaaca tcgcatcgag cgagcacgta ctcggatgga   2340
agccggtctt gtcgatcagg atgatctgga cgaagagcat caggggctcg cgccagccga   2400
actgttcgcc aggctcaagg cgcgcatgcc cgacggcgag gatctcgtcg tgacccatgg   2460
cgatgcctgc ttgccgaata tcatggtgga aaatggccgc ttttctggat tcatcgactg   2520
```

```
tggccggctg ggtgtggcgg accgctatca ggacatagcg ttggctaccc gtgatattgc   2580
tgaagagctt ggcggcgaat gggctgaccg cttcctcgtg ctttacggta tcgccgctcc   2640
cgattcgcag cgcatcgcct tctatcgcct tcttgacgag ttcttctgag cgggactctg   2700
gggttcgaaa tgaccgacca agcgacgccc aacctgccat cacgagattt cgattccacc   2760
gccgccttct atgaaaggtt gggcttcgga atcgttttcc gggacgccgg ctggatgatc   2820
ctccagcgcg gggatctcat gctggagttc ttcgcccacc ccaacttgtt tattgcagct   2880
tataatggtt acaaataaag caatagcatc acaaatttca caaataaagc atttttttca   2940
ctgcattcta gttgtggttt gtccaaactc atcaatgtat cttatcatgt ctgtataccg   3000
tcgacctcta gctagagctt ggcgtaatca tggtcatagc tgtttcctgt gtgaaattgt   3060
tatccgctca caattccaca caacatacga gccggaagca taaagtgtaa agcctggggt   3120
gcctaatgag tgagctaact cacattaatt gcgttgcgct cactgcccgc tttccagtcg   3180
ggaaacctgt cgtgccagct gcattaatga atcggccaac gcgcggggag aggcggtttg   3240
cgtattgggc gctcttccgc ttcctcgctc actgactcgc tgcgctcggt cgttcggctg   3300
cggcgagcgg tatcagctca ctcaaaggcg gtaatacggt tatccacaga atcaggggat   3360
aacgcaggaa agaacatgtg agcaaaaggc cagcaaaagg ccaggaaccg taaaaaggcc   3420
gcgttgctgg cgtttttcca taggctccgc ccccctgacg agcatcacaa aaatcgacgc   3480
tcaagtcaga ggtggcgaaa cccgacagga ctataaagat accaggcgtt tccccctgga   3540
agctccctcg tgcgctctcc tgttccgacc ctgccgctta ccggatacct gtccgccttt   3600
ctcccttcgg gaagcgtggc gctttctcat agctcacgct gtaggtatct cagttcggtg   3660
taggtcgttc gctccaagct gggctgtgtg cacgaacccc ccgttcagcc cgaccgctgc   3720
gccttatccg gtaactatcg tcttgagtcc aacccggtaa gacacgactt atcgccactg   3780
gcagcagcca ctggtaacag gattagcaga gcgaggtatg taggcggtgc tacagagttc   3840
ttgaagtggt ggcctaacta cggctacact agaagaacag tatttggtat ctgcgctctg   3900
ctgaagccag ttaccttcgg aaaaagagtt ggtagctctt gatccggcaa acaaaccacc   3960
gctggtagcg gtttttttgt ttgcaagcag cagattacgc gcagaaaaaa aggatctcaa   4020
gaagatcctt tgatcttttc tacggggtct gacgctcagt ggaacgaaaa ctcacgttaa   4080
gggattttgg tcatgagatt atcaaaaagg atcttcacct agatcctttt aaattaaaaa   4140
tgaagtttta aatcaatcta aagtatatat gagtaaactt ggtctgacag ttaccaatgc   4200
ttaatcagtg aggcacctat ctcagcgatc tgtctatttc gttcatccat agttgcctga   4260
ctccccgtcg tgtagataac tacgatacgg gagggcttac catctggccc cagtgctgca   4320
atgataccgc gagacccacg ctcaccggct ccagatttat cagcaataaa ccagccagcc   4380
ggaagggccg agcgcagaag tggtcctgca actttatccg cctccatcca gtctattaat   4440
tgttgccggg aagctagagt aagtagttcg ccagttaata gtttgcgcaa cgttgttgcc   4500
attgctacag gcatcgtggt gtcacgctcg tcgtttggta tggcttcatt cagctccggt   4560
tcccaacgat caaggcgagt tacatgatcc cccatgttgt gcaaaaaagc ggttagctcc   4620
ttcggtcctc cgatcgttgt cagaagtaag ttggccgcag tgttatcact catggttatg   4680
gcagcactgc ataattctct tactgtcatg ccatccgtaa gatgcttttc tgtgactggt   4740
gagtactcaa ccaagtcatt ctgagaatag tgtatgcggc gaccgagttg ctcttgcccg   4800
gcgtcaatac gggataatac cgcgccacat agcagaactt taaaagtgct catcattgga   4860
```

aaacgttctt cggggcgaaa actctcaagg atcttaccgc tgttgagatc cagttcgatg 4920
taacccactc gtgcacccaa ctgatcttca gcatctttta ctttcaccag cgtttctggg 4980
tgagcaaaaa caggaaggca aaatgccgca aaaaagggaa taagggcgac acggaaatgt 5040
tgaatactca tactcttcct ttttcaatat tattgaagca tttatcaggg ttattgtctc 5100
atgagcggat acatatttga atgtatttag aaaaataaac aaataggggt tccgcgcaca 5160
tttccccgaa aagtgccacc tgacgtc 5187

<210> SEQ ID NO 59
<211> LENGTH: 3959
<212> TYPE: DNA
<213> ORGANISM: Artificial Sequence
<220> FEATURE:
<223> OTHER INFORMATION: COMPLETELY ARTIFICIAL

<400> SEQUENCE: 59
gaattccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540
acggggtggt gcgtaacggc aaaagcaccg ccggacatca gcgctagcgg agtgtatact 600
ggcttactat gttggcactg atgagggtgt cagtgaagtg cttcatgtgg caggagaaaa 660
aaggctgcac cggtgcgtca gcagaatatg tgatacagga tatattccgc ttcctcgctc 720
actgactcgc tacgctcggt cgttcgactg cggcgagcgg aaatggctta cgaacggggc 780
ggagatttcc tggaagatgc caggaagata cttaacaggg aagtgagagg gccgcggcaa 840
agccgttttt ccataggctc cgcccccctg acaagcatca cgaaatctga cgctcaaatc 900
agtggtggcg aaacccgaca ggactataaa gataccaggc gtttccccct ggcggctccc 960
tcgtgcgctc tcctgttcct gcctttcggt ttaccggtgt cattccgctg ttatggccgc 1020
gtttgtctca ttccacgcct gacactcagt tccgggtagg cagttcgctc caagctggac 1080
tgtatgcacg aaccccccgt tcagtccgac cgctgcgcct tatccggtaa ctatcgtctt 1140
gagtccaacc cggaaagaca tgcaaaagca ccactggcag cagccactgg taattgattt 1200
agaggagtta gtcttgaagt catgcgccgg ttaaggctaa actgaaagga caagttttgg 1260
tgactgcgct cctccaagcc agttacctcg gttcaaagag ttggtagctc agagaacctt 1320
cgaaaaaccg ccctgcaagg cggttttttc gttttcagag caagagatta cgcgcagacc 1380
aaaacgatct caagaagatc atcttattaa tcagataaaa tatttctaga tcgtccattc 1440
cgacagcatc gccagtcact atggcgtgct gctagcgcta tatgcgttga tgcaatttct 1500
atgcgcaccc gttctcggag cactgtccga ccgctttggc cgccgcccag tcctgctcgc 1560
ttcgctactt ggagccacta tcgactacgc gatcatggcg accacacccg tcctgtgtaa 1620
tacgtagaca ctgtgtctcc ggaagacctt ccattctgaa atgagctgtt gacaattaat 1680
catccggctc gtataatgtg tggaattgtg agcggataac aatttcacac aggaaacaga 1740

```
ccatgggaat tcgagctcgg tacccgggga tcctctagat ttaagaagga gatatacata   1800
tgagtaaagg agaagaactt ttcactggag ttgtcccaat tcttgttgaa ttagatggtg   1860
atgttaatgg gcacaaattt tctgtcagtg gagagggtga aggtgatgca acatacggaa   1920
aacttaccct taaatttatt tgcactactg gaaaactacc tgttccatgg ccaacacttg   1980
tcactacttt cgcgtatggt cttcaatgct ttgcgagata cccagatcat atgaaacagc   2040
atgacttttt caagagtgcc atgcccgaag gttatgtaca ggaaagaact atatttttca   2100
aagatgacgg gaactacaag acacgtgctg aagtcaagtt tgaaggtgat acccttgtta   2160
atagaatcga gttaaaaggt attgatttta aagaagatgg aaacattctt ggacacaaat   2220
tggaatacaa ctataactca cacaatgtat acatcatggc agacaaacaa aagaatggaa   2280
tcaaagttaa cttcaaaatt agacacaaca ttgaagatgg aagcgttcaa ctagcagacc   2340
attatcaaca aaatactcca attggcgatg gccctgtcct tttaccagac aaccattacc   2400
tgtccacaca atctgccctt tcgaaagatc ccaacgaaaa gagagaccac atggtccttc   2460
ttgagtttgt aacagctgct gggattacac atggcatgga tgaactatac aaataaatgt   2520
ccagacctgc agccaagctc ccaagcttgg ctgttttggc ggatgagaga agattttcag   2580
cctgatacag attaaatcag aacgcagaag cggtctgata aaacagaatt tgcctggcgg   2640
cagtagcgcg gtggtcccac ctgaccccat gccgaactca gaagtgaaac gccgtagcgc   2700
cgatggtagt gtggggtctc cccatgcgag agtagggaac tgccaggcat caaataaaac   2760
gaaaggctca gtcgaaagac tgggcctttc gttttatctg ttgtttgtcg gtgaacgctc   2820
tcctgagtag gacaaatccg ccgggagcgg atttgaacgt tgcgaagcaa cggcccggag   2880
ggtggcgggc aggacgcccg ccataaactg ccaggcatca aattaagcag aaggccatcc   2940
tgacggatgg cctttttgcg tttctacaaa ctcttttgtt tatttttcta aatacattca   3000
aatatgtatc cgctcatgag acaataaccc tgataaatgc ttcaataatg gagacacagt   3060
gtcagatctt aaccggcagc gcccaacagt cccccggcca cggggcctgc caccataccc   3120
acgccgaaac aagcgccctg caccattatg ttccggatct gcatcgcagg atgctgctgg   3180
ctaccctgtg gaacacctac atctgtatta acgaagcgct aaccgttttt atcaggctct   3240
gggaggcaga ataaatgatc atatcgtcaa ttattacctc cacggggaga gcctgagcaa   3300
actggcctca ggcatttgag aagcacacgg tcacactgct tccggtagtc aataaaccgg   3360
taaaccagca atagacataa gcggctattt aacgaccctg ccctgaaccg acgaccgggt   3420
cgaatttgct ttcgaatttc tgccattcat ccgcttatta tcacttattc aggcgtagca   3480
ccaggcgttt aagggcacca ataactgcct taaaaaaatt acgccccgcc ctgccactca   3540
tcgcagtact gttgtaattc attaagcatt ctgccgacat ggaagccatc acagacggca   3600
tgatgaacct gaatcgccag cggcatcagc accttgtcgc cttgcgtata atatttgccc   3660
atggtgaaaa cgggggcgaa gaagttgtcc atattggcca cgtttaaatc aaaactggtg   3720
aaactcaccc agggattggc tgagacgaaa aacatattct caataaaccc tttagggaaa   3780
taggccaggt tttcaccgta acacgccaca tcttgcgaat atatgtgtag aaactgccgg   3840
aaatcgtcgt ggtattcact ccagagcgat gaaaacgttt cagtttgctc atggaaaacg   3900
gtgtaacaag ggtgaacact atcccatatc accagctcac cgtctttcat tgccatacg    3959
```

<210> SEQ ID NO 60
<211> LENGTH: 23618
<212> TYPE: DNA

<213> ORGANISM: Artificial Sequence
<220> FEATURE:
<223> OTHER INFORMATION: COMPLETELY ARTIFICIAL

<400> SEQUENCE: 60

```
gccggctaaa gtgtctacgt attacacagg acgggtgtgg tcgccatgat cgcgtagtcg      60
atagtggctc caagtagcga agcgagcagg actgggcggc ggccaaagcg gtcggacagt     120
gctccgagaa cgggtgcgca tagaaattgc atcaacgcat atagcgctag cagcacgcca     180
tagtgactgg cgatgctgtc ggaatggacg atctagaaat attttatctg attaataaga     240
tgatcttctt gagatcgttt tggtctgcgc gtaatctctt gctctgaaaa cgaaaaaacc     300
gccttgcagg gcggtttttc gaaggttctc tgagctacca actctttgaa ccgaggtaac     360
tggcttggag gagcgcagtc accaaaactt gtcctttcag tttagcctta accggcgcat     420
gacttcaaga ctaactcctc taaatcaatt accagtggct gctgccagtg gtgcttttgc     480
atgtctttcc gggttggact caagacgata gttaccggat aaggcgcagc ggtcggactg     540
aacggggggt tcgtgcatac agtccagctt ggagcgaact gcctacccgg aactgagtgt     600
caggcgtgga atgagacaaa cgcggccata acagcggaat gacaccggta aaccgaaagg     660
caggaacagg agagcgcacg agggagccgc caggggggaaa cgcctggtat ctttatagtc    720
ctgtcgggtt tcgccaccac tgatttgagc gtcagatttc gtgatgcttg tcaggggggc     780
ggagcctatg gaaaaacggc tttgccgcgg ccctctcact tccctgttaa gtatcttcct     840
ggcatcttcc aggaaatctc cgccccgttc gtaagccatt tccgctcgcc gcagtcgaac     900
gaccgagcgt agcgagtcag tgagcgagga agcggaatat atcctgtatc acatattctg     960
ctgacgcacc ggtgcagcct tttttctcct gccacatgaa gcacttcact gacaccctca    1020
tcagtgccaa catagtaagc cagtatacac tccgctagcg ctgatgtccg gcggtgcttt    1080
tgccgttacg caccaccccg tcagtagctg aacaggaggg acagctgata gaaacagaag    1140
ccactggagc acctcaaaaa caccatcata cactaaatca gtaagttggc agcatcaccc    1200
gacgcacttt gcgccgaata aatacctgtg acggaagatc acttcgcaga ataaataaat    1260
cctggtgtcc ctgttgatac cgggaagccc tgggccaact tttggcgaaa atgagacgtt    1320
gatcggcacg taagaggttc caactttcac cataatgaaa taagatcact accgggcgta    1380
tttttgagt tatcgagatt ttcaggagct aaggaagcta aaatggagaa aaaaatcact     1440
ggatatacca ccgttgatat atcccaatgg catcgtaaag aacattttga ggcatttcag    1500
tcagttgctc aatgtaccta taaccagacc gttcagctgg atattacggc ctttttaaag    1560
accgtaaaga aaaataagca caagttttat ccggccttta ttcacattct tgcccgcctg    1620
atgaatgctc atccggaatt ccgtatggca atgaaagacg gtgagctggt gatatgggat    1680
agtgttcacc cttgttacac cgttttccat gagcaaactg aaacgttttc atcgctctgg    1740
agtgaatacc acgacgattt ccggcagttt ctacacatat attcgcaaga tgtggcgtgt    1800
tacggtgaaa acctggccta tttccctaaa gggtttattg agaatatgtt tttcgtctca    1860
gccaatccct gggtgagttt caccagtttt gatttaaacg tggccaatat ggacaacttc    1920
ttcgcccccg ttttcaccat gggcaaatat tatacgcaag gcgacaaggt gctgatgccg    1980
ctggcgattc aggttcatca tgccgtctgt gatggcttcc atgtcggcag aatgcttaat    2040
gaattacaac agtactgcga tgagtggcag ggcggggcgt aattttttta aggcagttat    2100
tggtgccctt aaacgcctgg tgctacgcct gaataagtga taataagcgg atgaatggca    2160
gaaattcgaa agcaaattcg acccggtcgt cggttcaggg cagggtcgtt aaatagccgc    2220
```

-continued

```
ttatgtctat tgctggttta ccggtttatt gactaccgga agcagtgtga ccgtgtgctt   2280

ctcaaatgcc tgaggccagt ttgctcaggc tctccccgtg gaggtaataa ttgacgatat   2340

gatcatttat tctgcctccc agagcctgat aaaaacggtt agcgcttcgt taatacagat   2400

gtaggtgttc cacagggtag ccagcagcat cctgcgatgc agatccggaa cataatggtg   2460

cagggcgctt gtttcggcgt gggtatggtg gcaggccccg tggccggggg actgttgggc   2520

gctgccggtt aagatctgac acttaagccc gggcgttgac attgattatt gactagttat   2580

taatagtaat caattacggg gtcattagtt catagcccat atatggagtt ccgcgttaca   2640

taacttacgg taaatggccc gcctggctga ccgcccaacg acccccgccc attgacgtca   2700

ataatgacgt atgttcccat agtaacgcca atagggactt tccattgacg tcaatgggtg   2760

gagtatttac ggtaaactgc ccacttggca gtacatcaag tgtatcatat gccaagtacg   2820

ccccctattg acgtcaatga cggtaaatgg cccgcctggc attatgccca gtacatgacc   2880

ttatgggact ttcctacttg gcagtacatc tacgtattag tcatcgctat taccatggtg   2940

atgcggtttt ggcagtacat caatgggcgt ggatagcggt ttgactcacg gggatttcca   3000

agtctccacc ccattgacgt caatgggagt ttgttttggc accaaaatca acgggacttt   3060

ccaaaatgtc gtaacaactc cgccccattg acgcaaatgg gcggtaggcg tgtacggtgg   3120

gaggtctata taagcagagc tctctggcta actagagaac ccactgctta ctggcttatc   3180

gaaattaata cgactcacta tagggagacc caagctggct agcgtgtcgc ccggagtact   3240

ggtcgacctc cgaagttggg ggggagcgaa agcaggtcaa ttatattcaa tatggaaaga   3300

ataaaagaac taaggaatct aatgtcgcag tctcgcactc gcgagatact cacaaaaacc   3360

accgtggacc atatggccat aatcaagaag tacacatcag gaagacagga gaagaaccca   3420

gcacttagga tgaaatggat gatggcaatg aaatatccaa ttacagcaga caagaggata   3480

acggaaatga ttcctgagag aaatgagcag ggacaaactt tatggagtaa aatgaatgac   3540

gccggatcag accgagtgat ggtatcacct ctggctgtga catggtggaa taggaatgga   3600

ccagtgacaa gtacagttca ttatccaaaa atctacaaaa cttattttga aaaagtcgaa   3660

aggttaaaac atggaacctt tggccctgtc cattttagaa accaagtcaa aatacgtcga   3720

agagttgaca taaatcctgg tcatgcagat ctcagtgcca aagaggcaca ggatgtaatc   3780

atggaagttg ttttccctaa cgaagtggga gccaggatac taacatcgga atcgcaacta   3840

acgacaacca aagagaagaa agaagaactc cagggttgca aaatttctcc tctgatggtg   3900

gcatacatgt tggagagaga actggtccgc aaaacgagat tcctcccagt ggctggtgga   3960

acaagcagtg tgtacattga agtgttgcat ttgacccaag gaacatgctg ggaacagatg   4020

tacactccag gaggggaggc gaggaatgat gatgttgatc aaagcttaat tattgctgct   4080

agaaacatag taagaagagc cacagtatca gcagatccac tagcatcttt attggagatg   4140

tgccacagca cgcagattgg tggaataagg atggtaaaca tccttaggca gaacccaaca   4200

gaagagcaag ccgtggatat ttgcaaggct gcaatgggac tgagaattag ctcatccttc   4260

agttttggtg gattcacatt taagagaaca agcggatcat cagtcaagag agaggaagag   4320

gtgcttacgg gcaatcttca gacattgaag ataagagtac atgagggata tgaagagttc   4380

acaatggttg ggagaagagc aacagctata ctcagaaaag caaccaggag attgattcag   4440

ctgatagtga gtgggagaga cgaacagtcg attgccgaag caataattgt ggccatggta   4500

ttttcacaag aggattgtat gataaaagca gttagaggtg acctgaattt cgtcaatagg   4560
```

-continued

```
gcgaatcagc gattgaatcc catgcaccaa cttttgagac attttcagaa ggatgcaaag   4620
gtgctctttc aaaattgggg aattgaatcc atcgacaatg tgatgggaat gatcgggata   4680
ttgcccgaca tgactccaag caccgagatg tcaatgagag gagtgagaat cagcaaaatg   4740
ggggtagatg agtattccag cgcggagaag atagtggtga gcattgaccg tttttttgaga  4800
gttagggacc aacgtgggaa tgtactactg tctcccgagg agatcagtga aacacaggga   4860
acagagaaac tgacaataac ttactcatcg tcaatgatgt gggagattaa tggtcctgaa   4920
tcagtgttgg tcaataccta tcagtggatc atcagaaact gggaaactgt taaaattcag   4980
tggtcccaga atcctacaat gctgtacaat aaaatggaat ttgagccatt tcagtcttta   5040
gttccaaagg ccgttagagg ccaatacagt gggtttgtga gaactctgtt ccaacaaatg   5100
agggatgtgc ttgggacatt tgataccgct cagataataa aacttcttcc cttcgcagcc   5160
gctccaccaa agcaaagtag aacgcagttc tcctcattga ctataaatgt gaggggatca   5220
ggaatgagaa tacttgtaag ggcaattctt ccagtattca actacaacaa gaccactaaa   5280
agactcacag ttctcggaaa ggatgctggc cctttaactg aagacccaga tgaaggcaca   5340
gctggagttg agtccgcagt tctgagagga ttcctcattc tgggcaaaga agacaggaga   5400
tatggaccag cattaagcat aaatgaactg agcaaccttg cgaaaggaga gaaggctaat   5460
gtgctaattg ggcaaggaga cgtggtgttg gtaatgaaac ggaaacggaa ctctagcata   5520
cttactgaca gccagacagc gaccaaaaga attcggatgg ccatcaatta gtgtcgaata   5580
gtttaaaaac gaccttgttt ctactacaga cgaacatata aggcatccga aaaaaacgtt   5640
ctagtcccat aggcgccgac taccggcagc ggctccgacg gcagccgagg tttacctcga   5700
cgtaactgga ggtacaaaat tacagcgacg cctctggcag ctccggagct gtagcgcccc   5760
cccccacagc cagagcggcc aagacaatcc gaaacggggt agacctggac gcggatcgca   5820
agccgccccg gcagcgacct ctagccgccg ccgcggagag cgcgagacgg tagcacccgg   5880
gtagaccgtt ccgccgtttc cgagacgccc cggcagcgac ccctagccgc cgccgccgcg   5940
gagagaccga gccggacggt gcccgccggg accaggtaga ccgttccgcc gtgccccagc   6000
cacctccgcg aagcgaccga aagggcgaat tctgcagaaa gcttaagttt aaaccgctga   6060
tcagcctcga ctgtgccttc tagttgccag ccatctgttg tttgcccctc ccccgtgcct   6120
tccttgaccc tggaaggtgc cactcccact gtcctttcct aataaaatga ggaaattgca   6180
tcgcattgtc tgagtaggtg tcattctatt ctggggggtg gggtggggca ggacagcaag   6240
ggggaggatt gggaagacaa tagcaggcat gctggggatg cggtgggctc tatggcggcc   6300
gcgtgtcgcc cggagtactg gtcgacctcc gaagttgggg gggagcaaaa gcagggtgac   6360
aaagacataa tggatccaaa cactgtgtca agctttcagg tagattgctt tctttggcat   6420
gtccgcaaaa gagttgcaga ccaagaacta ggtgatgccc cattccttga tcggcttcgc   6480
cgagatcaga agtccctaag aggaagaggc agcactcttg gtctggacat cgaaacagcc   6540
acccgtgctg gaaagcaaat agtggagcgg attctgaagg aagaatctga tgaggcactc   6600
aaaatgacca tggcctctgt acctgcatcg cgctacctaa ctgacatgac tcttgaggaa   6660
atgtcaaggc actggttcat gctcatgccc aagcagaaag tggcaggccc tctttgtatc   6720
agaatggacc aggcgatcat ggataagaac atcatactga aagcgaactt cagtgtgatt   6780
tttgaccggc tggagactct aatattacta agggccttca ccgaagaggg gacaattgtt   6840
ggcgaaattt caccactgcc ctctcttcca ggacatactg atgaggatgt caaaaatgca   6900
gttggggtcc tcatcggagg acttgaatgg aataataaca cagttcgagt ctctgaaact   6960
```

```
ctacagagat tcgcttggag aagcagtaat gagaatggga gacctccact cactccaaaa   7020
cagaaacgga aaatggcggg aacaattagg tcagaagttt gaagaaataa gatggttgat   7080
tgaagaagtg agacacagac tgaagataac agagaatagt tttgagcaaa taacatttat   7140
gcaagcctta caactattgc ttgaagtgga gcaagagata agaactttct cgtttcagct   7200
tatttaataa taaaaaacac ccttgtttct actacagacg aacatataag gcatccgaaa   7260
aaaacgttct agtcccatag gcgccgacta ccggcagcgg ctccgacggc agccgaggtt   7320
tacctcgacg taactggagg tacaaaatta cagcgacgcc tctggcagct ccggagctgt   7380
agcgcccccc cccacagcca gagcggccaa gacaatccga aacggggtag acctggacgc   7440
ggatcgcaag ccgccccggc agcgacctct agccgccgcc gcggagagcg cgagacggta   7500
gcacccgggt agaccgttcc gccgtttccg agacgccccg gcagcgaccc ctagccgccg   7560
ccgccgcgga gagaccgagc cggacggtgc ccgccgggac caggtagacc gttccgccgt   7620
gccccagcca cctccgcgaa gcgaccgagc gcgcgttgac attgattatt gactagttat   7680
taatagtaat caattacggg gtcattagtt catagcccat atatggagtt ccgcgttaca   7740
taacttacgg taaatggccc gcctggctga ccgcccaacg acccccgccc attgacgtca   7800
ataatgacgt atgttcccat agtaacgcca atagggactt tccattgacg tcaatgggtg   7860
gagtatttac ggtaaactgc ccacttggca gtacatcaag tgtatcatat gccaagtacg   7920
ccccctattg acgtcaatga cggtaaatgg cccgcctggc attatgccca gtacatgacc   7980
ttatgggact ttcctacttg gcagtacatc tacgtattag tcatcgctat taccatggtg   8040
atgcggtttt ggcagtacat caatgggcgt ggatagcggt ttgactcacg gggatttcca   8100
agtctccacc ccattgacgt caatgggagt ttgttttggc accaaaatca acgggacttt   8160
ccaaaatgtc gtaacaactc cgccccattg acgcaaatgg gcggtaggcg tgtacggtgg   8220
gaggtctata taagcagagc tctctggcta actagagaac ccactgctta ctggcttatc   8280
gaaattaata cgactcacta tagggagacc caagctggct agcgtgtcgc ccggagtact   8340
ggtcgacctc cgaagttggg ggggagcgaa agcaggcaaa ccatttgaat ggatgtcaat   8400
ccgactttac ttttcttaaa agtgccagca caaaatgcta taagcacaac tttcccttat   8460
actggagacc ctccttacag ccatgggaca ggaacaggat acaccatgga tactgtcaac   8520
aggacacatc agtactcaga aaggggaaga tggacaacaa acaccgaaac tggagcaccg   8580
caactcaacc cgattgatgg gccactgcca gaagacaatg aaccaagtgg ttatgcccaa   8640
acagattgtg tattggaagc aatggccttc cttgaggaat cccatcctgg tatctttgag   8700
acctcgtgtc ttgaaacgat ggaggttgtt cagcaaacac gagtggacaa gctgacacaa   8760
ggccgacaga cctatgactg gactctaaat aggaaccagc ctgctgcaac agcattggcc   8820
aacacaatag aagtgttcag atcaaatggc ctcacggcca atgaatctgg aaggctcata   8880
gacttcctta aggatgtaat ggagtcaatg aacaaagaag aaatggagat cacaactcat   8940
tttcagagaa agagacgagt gagagacaat atgactaaga aaatggtgac acagagaaca   9000
ataggtaaaa ggaagcagag attgaacaaa aggagttatc taattagggc attaaccctg   9060
aacacaatga ccaaagatgc tgagagaggg aagctaaaac ggagagcaat tgcaacccca   9120
gggatgcaaa taagggggtt tgtatacttt gttgagacac tagcaaggag tatatgtgag   9180
aaacttgaac aatcaggatt gccagttgga ggcaatgaga agaaagcaaa gttggcaaat   9240
gttgtaagga agatgatgac caattctcag gacactgaaa tttctttcac catcactgga   9300
```

-continued

```
gataacacca aatggaacga aaatcagaac cctcggatgt ttttggccat gatcacatat   9360
ataaccagaa atcagcccga atggttcaga aatgttctaa gtattgctcc aataatgttc   9420
tcaaacaaaa tggcgagact gggaaagggg tacatgtttg agagcaagag tatgaaaatt   9480
agaactcaaa tacctgcaga aatgctagca agcatcgatt tgaaatactt caatgattca   9540
actagaaaga agattgaaaa aatccggccg ctcttaatag atgggactgc atcattgagc   9600
cctggaatga tgatgggcat gttcaatatg ttaagtactg tattaggcgt ctccatcctg   9660
aatcttggac aaaagagaca caccaagact acttactggt gggatggtct tcaatcttct   9720
gatgattttg ctctgattgt gaatgcaccc aatcatgaag ggattcaagc cggagtcaac   9780
aggttttatc gaacctgtaa gctacttgga attaatatga gcaagaaaaa gtcttacata   9840
aacagaacag gtacatttga attcacaagt tttttctatc gttatgggtt tgttgccaat   9900
ttcagcatgg agcttcccag ctttggggtg tctgggatca acgagtctgc ggacatgagt   9960
attggagtta ctgtcatcaa aaacaatatg ataaacaatg atcttggtcc agcaaccgct  10020
caaatggccc ttcagctgtt catcaaagat tacaggtaca cgtaccggtg ccatagaggt  10080
gacacacaaa tacaaacccg aagatcattt gaaataaaga aactgtggga gcaaacccat  10140
tccaaagctg gactgctggt ctccgacgga ggcccaaatt tatacaacat tagaaatctc  10200
cacattcctg aagtctgctt gaaatgggaa ttaatggatg aggattacca ggggcgttta  10260
tgcaacccac tgaacccatt tgtcaaccat aaagacattg aatcagtgaa caatgcagtg  10320
ataatgccag cacatggtcc agccaaaaac atggagtatg atgctgttgc aacaacacac  10380
tcctggatcc ccaaaagaaa tcgatccatc ttgaatacaa gccaaagagg aatacttgaa  10440
gatgaacaaa tgtaccaaaa gtgctgcaac ttatttgaaa aattcttccc cagcagttca  10500
tacagaagac cagtcgggat atccagtatg gtggaggcta tggtttccag agcccgaatt  10560
gatgcacgaa ttgatttcga atctggaagg ataaagaaag aggagttcac tgagatcatg  10620
aagatctgtt ccaccattga agagctcaga cggcaaaaat agtgaattta gcttgtcctt  10680
catgaaaaaa tgccttgttt ctactacaga cgaacatata aggcatccga aaaaaacgtt  10740
ctagtcccat aggcgccgac taccggcagc ggctccgacg gcagccgagg tttacctcga  10800
cgtaactgga ggtacaaaat tacagcgacg cctctggcag ctccggagct gtagcgcccc  10860
cccccacagc cagagcggcc aagacaatcc gaaacggggt agacctggac gcggatcgca  10920
agccgccccg gcagcgacct ctagccgccg ccgcggagag cgcgagacgg tagcacccgg  10980
gtagaccgtt ccgccgtttc cgagacgccc cggcagcgac ccctagccgc cgccgccgcg  11040
gagagaccga gccggacggt gcccgccggg accaggtaga ccgttccgcc gtgccccagc  11100
cacctccgcg aagcgaccga aagggcgaat tctgcagaaa gcttaagttt aaaccgctga  11160
tcagcctcga ctgtgccttc tagttgccag ccatctgttg tttgcccctc ccccgtgcct  11220
tccttgaccc tggaaggtgc cactcccact gtcctttcct aataaaatga ggaaattgca  11280
tcgcattgtc tgagtaggtg tcattctatt ctggggggtg gggtggggca ggacagcaag  11340
ggggaggatt gggaagacaa tagcaggcat gctggggatg cggtgggctc tatggcctgc  11400
agggtgtcgc ccggagtact ggtcgacctc cgaagttggg ggggagcaaa agcaggtaga  11460
tattgaaaga tgagtcttct aaccgaggtc gaaacgtacg ttctctctat cgtcccgtca  11520
ggcccctca aagccgagat cgcacagaga cttgaagatg tctttgcagg gaagaacacc  11580
gatcttgagg ttctcatgga atggctaaag acaagaccaa tcctgtcacc tctgactaag  11640
gggattttag gatttgtgtt cacgctcacc gtgcccagtg agcggggact gcagcgtaga  11700
```

-continued

```
cgctttgtcc aaaatgctct taatgggaac ggagatccaa ataacatgga caaagcagtt  11760
aaactgtata ggaagcttaa gagggagata acattccatg gggccaaaga aatagcactc  11820
agttattctg ctggtgcact tgccagttgt atgggcctca tatacaacag gatgggggct  11880
gtgaccactg aagtggcatt tggcctggta tgcgcaacct gtgaacagat tgctgactcc  11940
cagcatcggt ctcataggca aatggtgaca acaaccaatc cactaatcag acatgagaac  12000
agaatggttc tagccagcac tacagctaag gctatggagc aaatggctgg atcgagtgag  12060
caagcagcag aggccatgga tattgctagt caggccaggc aaatggtgca ggcgatgaga  12120
accgttggga ctcatcctag ctccagtgct ggtctaaaag atgatcttct tgaaaatttg  12180
caggcctatc agaaacgaat gggggtgcag atgcaacgat tcaagtgatc ctctcgtcat  12240
tgcagcaaat atcattggaa tcttgcactt gatattgtgg attcttgatc gtcttttttt  12300
caaatgcatt tatcgtcgct ttaaatacgg tttgaaaaga gggccttcta cggaaggagt  12360
gccagagtct atgagggaag aatatcgaaa ggaacagcag aatgctgtgg atgttgacga  12420
tggtcatttt gtcaacatag agctggagta aaaaactacc ttgtttctac tacagacgaa  12480
catataaggc atccgaaaaa aacgttctag tcccataggc gccgactacc ggcagcggct  12540
ccgacggcag ccgaggttta cctcgacgta actggaggta caaaattaca gcgacgcctc  12600
tggcagctcc ggagctgtag cgcccccccc cacagccaga gcggccaaga caatccgaaa  12660
cggggtagac ctggacgcgg atcgcaagcc gccccggcag cgacctctag ccgccgccgc  12720
ggagagcgcg agacggtagc acccgggtag accgttccgc cgtttccgag acgccccggc  12780
agcgacccct agccgccgcc gccgcggaga gaccgagccg gacggtgccc gccgggacca  12840
ggtagaccgt tccgccgtgc cccagccacc tccgcgaagc gaccgaggta ccgttgacat  12900
tgattattga ctagttatta atagtaatca attacggggt cattagttca tagcccatat  12960
atggagttcc gcgttacata acttacggta aatggcccgc ctggctgacc gcccaacgac  13020
ccccgcccat tgacgtcaat aatgacgtat gttcccatag taacgccaat agggactttc  13080
cattgacgtc aatgggtgga gtatttacgg taaactgccc acttggcagt acatcaagtg  13140
tatcatatgc caagtacgcc ccctattgac gtcaatgacg gtaaatggcc cgcctggcat  13200
tatgcccagt acatgacctt atgggacttt cctacttggc agtacatcta cgtattagtc  13260
atcgctatta ccatggtgat gcggttttgg cagtacatca atgggcgtgg atagcggttt  13320
gactcacggg gatttccaag tctccacccc attgacgtca atgggagttt gttttggcac  13380
caaaatcaac gggactttcc aaaatgtcgt aacaactccg ccccattgac gcaaatgggc  13440
ggtaggcgtg tacggtggga ggtctatata agcagagctc tctggctaac tagagaaccc  13500
actgcttact ggcttatcga aattaatacg actcactata gggagaccca agctggctag  13560
cgtgtcgccc ggagtactgg tcgacctccg aagttggggg ggagcgaaag caggtactga  13620
ttcaaaatgg aagattttgt gcgacaatgc ttcaatccga tgattgtcga gcttgcggaa  13680
aaggcaatga aagagtatgg agaggacctg aaaatcgaaa caaacaaatt tgcagcaata  13740
tgcactcact tggaagtgtg cttcatgtat tcagattttc acttcatcga tgagcaaggc  13800
gagtcaatag tcgtagaact tggcgatcca aatgcacttt tgaagcacag atttgaaata  13860
atcgagggaa gagatcgcac aatagcctgg acagtaataa acagtatttg caacactaca  13920
ggggctgaga aaccaaagtt tctaccagat ttgtatgatt acaagaagaa tagattcatc  13980
gaaattggag taacaaggag agaagttcac atatactatc tggaaaaggc caataaaatt  14040
```

-continued

```
aaatctgaga agacacacat ccacattttc tcattcactg gggaggaaat ggccacaaag  14100
gccgactaca ctctcgatga agaaagcagg gctaggatca aaaccaggct attcaccata  14160
agacaagaaa tggctagcag aggcctctgg gattcctttc gtcagtccga gagaggcgaa  14220
gagacaattg aagaaagatt tgaaatcaca ggaacaatgc gcaagcttgc cgaccaaagt  14280
ctcccgccaa acttctccag ccttgaaaaa tttagagcct atgtggatgg attcgaaccg  14340
aacggctaca ttgagggcaa gctttctcaa atgtccaaag aagtaaatgc tagaattgaa  14400
ccttttttga aatcaacacc acgaccactt agacttccgg atgggcctcc ctgttctcag  14460
cggtccaaat tcctgctgat ggatgcctta aaattaagca ttgaggaccc aagtcatgag  14520
ggagagggga taccgctata tgatgcaatc aaatgcatga gaacattctt tggatggaag  14580
gaacccaatg ttgttaaacc acacgaaaag ggaataaatc caaattatct tctgtcatgg  14640
aagcaagtac tggcagaact gcaggacatt gagaatgagg agaaaattcc aaggactaaa  14700
aatatgaaga aaacgagtca gttaaagtgg gcacttggtg agaacatggc accagaaaag  14760
gtagactttg acgattgtaa agatgtaggc gatttgaagc aatatgatag tgatgaacca  14820
gaattgaggt cgcttgcaag ttggattcag aatgagttca acaaggcatg tgaactgacc  14880
gattcaagct ggatagagct cgatgagatt ggagaagatg cggctccaat tgaacacatt  14940
gcaagcatga gaaggaatta tttcacagca gaggtgtctc attgcagagc cacagaatac  15000
ataatgaagg gggtgtacat caatactgcc ttgcttaatg catcctgtgc agcaatggat  15060
gatttccaat taattccaat gataagcaag tgtagaacta aggagggaag gcgaaagacc  15120
aatttgtacg gtttcatcat aaaaggaaga tcccacttaa ggaatgacac cgatgtggta  15180
aactttgtga gcatggagtt ttccctcact gacccaagac ttgaaccaca caaatgggag  15240
aagtactgtg ttcttgaggt aggagatatg cttctaagaa gtgccatagg ccatgtgtca  15300
aggcctatgt tcttgtatgt gaggacaaat ggaacctcaa aaattaaaat gaaatggggg  15360
atggaaatga ggcgttgcct ccttcagtca cttcaacaaa tcgagagtat gattgaagct  15420
gagtcctctg tcaaggagaa agacatgacc aaagagttct ttgaaaacaa atcagaaaca  15480
tggcccgttg gagagtcccc caaaggagtg gaggaaggtt ccattgggaa ggtctgcaga  15540
actttattgg caaagtcggt attcaacagc ttgtatgcat ctccacaact agaaggattt  15600
tcagctgaat caagaaaact gcttcttatc gttcaggctc ttagggacaa cctggaacct  15660
gggacctttg atcttggggg gctatatgaa gcaattgagg agtgcctgat taatgatccc  15720
tgggttttgc ttaatgcttc ttggttcaac tccttcctca cacatgcatt gagatagttg  15780
tggcaatgct actatttgct atccatactg tccaaaaaag taccttgttt ctactacaga  15840
cgaacatata aggcatccga aaaaaacgtt ctagtcccat aggcgccgac taccggcagc  15900
ggctccgacg gcagccgagg tttacctcga cgtaactgga ggtacaaaat tacagcgacg  15960
cctctggcag ctccggagct gtagcgcccc cccccacagc cagagcggcc aagacaatcc  16020
gaaacggggt agacctggac gcggatcgca agccgccccg gcagcgacct ctagccgccg  16080
ccgcggagag cgcgagacgg tagcacccgg gtagaccgtt ccgccgtttc cgagacgccc  16140
cggcagcgac ccctagccgc cgccgccgcg gagagaccga gccggacggt gcccgccggg  16200
accaggtaga ccgttccgcc gtgccccagc cacctccgcg aagcgaccga aagggcgaat  16260
tctgcagaaa gcttaagttt aaaccgctga tcagcctcga ctgtgccttc tagttgccag  16320
ccatctgttg tttgcccctc ccccgtgcct tccttgaccc tggaaggtgc cactcccact  16380
gtcctttcct aataaaatga ggaaattgca tcgcattgtc tgagtaggtg tcattctatt  16440
```

```
ctggggggtg gggtggggca ggacagcaag ggggaggatt gggaagacaa tagcaggcat  16500
gctggggatg cggtgggctc tatggttaat taagtgtcgc ccggagtact ggtcgacctc  16560
cgaagttggg ggggagcgaa agcaggagtt taaatgaatc caaaccagaa aataataacc  16620
attgggtcaa tctgtatggt agtcggaata attagcctaa tattgcaaat aggaaatata  16680
atctcaatat ggattagcca ttcaattcaa accggaaatc aaaaccatac tggaatatgc  16740
aaccaaggca gcattaccta taaagttgtt gctgggcagg actcaacttc agtgatatta  16800
accggcaatt catctctttg tcccatccgt gggtgggcta tacacagcaa agacaatggc  16860
ataagaattg gttccaaagg agacgttttt gtcataagag agccttttat ttcatgttct  16920
cacttggaat gcaggacctt ttttctgact caaggcgcct tactgaatga caagcattca  16980
agggggacct ttaaggacag aagcccttat agggccttaa tgagctgccc tgtcggtgaa  17040
gctccgtccc cgtacaattc aaggtttgaa tcggttgctt ggtcagcaag tgcatgtcat  17100
gatggaatgg gctggctaac aatcggaatt tctggtccag atgatggagc agtggctgta  17160
ttaaaataca accgcataat aactgaaacc ataaaaagtt ggaggaagaa tatattgaga  17220
acacaagagt ctgaatgtac ctgtgtaaat ggttcatgtt ttaccataat gaccgatggc  17280
ccaagtgatg ggctggcctc gtacaaaatt ttcaagatcg agaaggggaa ggttactaaa  17340
tcgatagagt tgaatgcacc taattctcac tacgaggaat gttcctgtta ccctgatacc  17400
ggcaaagtga tgtgtgtgtg cagagacaat tggcacggtt cgaaccgacc atgggtgtcc  17460
ttcgaccaaa acctagatta taaaatagga tacatctgca gtggggtttt cggtgacaac  17520
ccgcgtccca aagatggaac aggcagctgt ggcccagtgt ctgctgatgg agcaaacgga  17580
gtaaagggat tttcatataa gtatggcaat ggtgtttgga taggaaggac taaaagtgac  17640
agttccagac atgggtttga gatgatttgg gatcctaatg gatggacaga gactgatagt  17700
aggttctcta tgagacaaga tgttgtggca ataactaatc ggtcagggta cagcggaagt  17760
ttcgttcaac atcctgagct aacagggcta gactgtatga ggccttgctt ctgggttgaa  17820
ttaatcaggg ggctacctga ggaggacgca atctggacta gtgggagcat catttctttt  17880
tgtggtgtga atagtgatac tgtagattgg tcttggccag acggtgctga gttgccgttc  17940
accattgaca agtagtttgt tcaaaaaact ccttgtttct actacagacg aacatataag  18000
gcatccgaaa aaaacgttct agtcccatag gcgccgacta ccggcagcgg ctccgacggc  18060
agccgaggtt tacctcgacg taactggagg tacaaaatta cagcgacgcc tctggcagct  18120
ccggagctgt agcgcccccc cccacagcca gagcggccaa gacaatccga aacggggtag  18180
acctggacgc ggatcgcaag ccgccccggc agcgacctct agccgccgcc gcggagagcg  18240
cgagacggta gcacccgggt agaccgttcc gccgtttccg agacgccccg gcagcgaccc  18300
ctagccgccg ccgccgcgga gagaccgagc cggacggtgc ccgccgggac caggtagacc  18360
gttccgccgt gccccagcca cctccgcgaa gcgaccgagg gcccgttgac attgattatt  18420
gactagttat taatagtaat caattacggg gtcattagtt catagcccat atatggagtt  18480
ccgcgttaca taacttacgg taaatggccc gcctggctga ccgcccaacg acccccgccc  18540
attgacgtca ataatgacgt atgttcccat agtaacgcca atagggactt tccattgacg  18600
tcaatgggtg gagtatttac ggtaaactgc ccacttggca gtacatcaag tgtatcatat  18660
gccaagtacg ccccctattg acgtcaatga cggtaaatgg cccgcctggc attatgccca  18720
gtacatgacc ttatgggact ttcctacttg gcagtacatc tacgtattag tcatcgctat  18780
```

taccatggtg atgcggtttt ggcagtacat caatgggcgt ggatagcggt ttgactcacg 18840
gggatttcca agtctccacc ccattgacgt caatgggagt ttgttttggc accaaaatca 18900
acgggacttt ccaaaatgtc gtaacaactc cgccccattg acgcaaatgg gcggtaggcg 18960
tgtacggtgg gaggtctata taagcagagc tctctggcta actagagaac ccactgctta 19020
ctggcttatc gaaattaata cgactcacta tagggagacc caagctggct agcgtgtcgc 19080
ccggagtact ggtcgacctc cgaagttggg ggggagcaaa agcagggtag ataatcactc 19140
acagagtgac atcgaaatca tggcgaccaa aggcaccaaa cgatcttacg aacagatgga 19200
gactgatgga gaacgccaga atgccactga aatcagagca tctgtcggaa aaatgattga 19260
tggaattgga cgattctaca tccaaatgtg caccgaactt aaactcagtg attatgaggg 19320
acggctgatt cagaacagct taacaataga gagaatggtg ctctctgctt ttgacgagag 19380
gaggaataaa tatctagaag aacatcccag tgcggggaaa gatcctaaga aaactggagg 19440
acctatatac aggagagtag atggaaagtg gaggagagaa ctcatccttt atgacaaaga 19500
agaaataaga cgaatctggc gccaagctaa taatggtgac gatgcaacgg ctggtctgac 19560
tcacatgatg atctggcact ccaatttgaa tgatgcaact taccagagga caagagctct 19620
tgttcgcaca ggaatggatc ccaggatgtg ctcactgatg cagggttcaa ccctccctag 19680
gaggtctggg gccgcaggtg ctgcagtcaa aggagttgga acaatggtga tggaattgat 19740
cagaatgatc aaacgtggga tcaatgatcg gaacttctgg aggggtgaga atggacggag 19800
aacaaggatt gcttatgaaa gaatgtgcaa cattctcaaa gggaaatttc aaacagctgc 19860
acaaagaaca atggtggatc aagtgagaga gagccggaat ccaggaaatg ctgagttcga 19920
agatctcatc tttttagcac ggtctgcact catattgaga gggtcagttg ctcacaagtc 19980
ctgcctgcct gcctgtgtgt atggatctgc cgtagccagt ggatacgact ttgaaagaga 20040
gggatactct ctagtcggaa tagacccttt cagactgctt caaaacagcc aagtatacag 20100
cctaatcaga ccaaatgaga atccagcaca caagagtcaa ctggtgtgga tggcatgcca 20160
ttctgctgca tttgaagatc taagagtatc aagcttcatc agagggacga aagtggtccc 20220
aagagggaag ctttccacta gaggagttca aattgcttcc aatgaaaaca tggagactat 20280
ggaatcaagt acccttgaac tgagaagcag atactgggcc ataaggacca gaagtggagg 20340
gaacaccaat caacagaggg cttcctcggg ccaaatcagc atacaaccta cgttctcagt 20400
acagagaaat ctcccttttg acagaccaac cattatggca gcattcactg ggaatacaga 20460
ggggagaaca tctgacatga gaaccgaaat cataaggctg atggaaagtg caagaccaga 20520
agatgtgtct ttccaggggc ggggagtctt cgagctctcg gacgaaaagg caacgagccc 20580
gatcgtgccc tcctttgaca tgagtaatga aggatcttat ttcttcggag acaatgcaga 20640
ggagtacgac aattaaagaa aaatacccct gtttctacta cagacgaaca tataaggcat 20700
ccgaaaaaaa cgttctagtc ccataggcgc cgactaccgg cagcggctcc gacggcagcc 20760
gaggtttacc tcgacgtaac tggaggtaca aaattacagc gacgcctctg gcagctccgg 20820
agctgtagcg cccccccccca cagccagagc ggccaagaca atccgaaacg gggtagacct 20880
ggacgcggat cgcaagccgc cccggcagcg acctctagcc gccgccgcgg agagcgcgag 20940
acggtagcac ccgggtagac cgttccgccg tttccgagac gccccggcag cgacccctag 21000
ccgccgccgc cgcggagaga ccgagccgga cggtgcccgc cgggaccagg tagaccgttc 21060
cgccgtgccc cagccacctc cgcgaagcga ccgaaagggc gaattctgca gaaagcttaa 21120
gtttaaaccg ctgatcagcc tcgactgtgc cttctagttg ccagccatct gttgtttgcc 21180

-continued

```
cctcccccgt gccttccttg accctggaag gtgccactcc cactgtcctt tcctaataaa  21240
atgaggaaat tgcatcgcat tgtctgagta ggtgtcattc tattctgggg ggtggggtgg  21300
ggcaggacag caagggggag gattgggaag acaatagcag gcatgctggg gatgcggtgg  21360
gctctatggc acttacacta acacgtggtg tcgcccggag tactggtcga cctccgaagt  21420
tggggggggag caaaagcagg ggaaaataaa aacaaccaaa atgaaggcaa aactactggt  21480
cctgttatat gcatttgtag ctacagatgc agacacaata tgtataggct accatgcgaa  21540
caactcaacc gacactgttg acacaatact cgagaagaat gtggcagtga cacattctgt  21600
taacctgctc gaagacagcc acaacgggaa actatgtaaa ttaaaaggaa tagccccact  21660
acaattgggg aaatgtaaca tcaccggatg gctcttggga aatccagaat gcgactcact  21720
gcttccagcg agatcatggt cctacattgt agaaacacca aactctgaga atggagcatg  21780
ttatccagga gatctcatcg actatgagga actgagggag caattgagct cagtatcatc  21840
attagaaaga ttcgaaatat ttcccaagga aagttcatgg cccaaccaca cattcaacgg  21900
agtaacagta tcatgctccc ataggggaaa aagcagtttt tacagaaatt tgctatggct  21960
gacgaagaag gggattcat acccaaagct gaccaattcc tatgtgaaca ataaagggaa  22020
agaagtcctt gtactatggg gtgttcatca cccgtctagc agtgatgagc aacagagtct  22080
ctatagtaat ggaaatgctt atgtctctgt agcgtcttca aattataaca ggagattcac  22140
cccggaaata gctgcaaggc ccaaagtaag agatcaacat gggaggatga actattactg  22200
gaccttgcta gaacccggag acacaataat atttgaggca actggtaatc taatagcacc  22260
atggtatgct ttcgcactga gtagagggtt tgagtccggc atcatcacct caaacgcgtc  22320
aatgcatgag tgtaacacga agtgtcaaac accccaggga gctataaaca gcaatctccc  22380
tttccagaat atacacccag tcacaatagg agagtgccca aaatatgtca ggagtaccaa  22440
attgaggatg gttacaggac taagaaacat cccatccatt caatacagag gtctatttgg  22500
agccattgct ggttttattg aggggggatg gactggaatg atagatggat ggtatggtta  22560
tcatcatcag aatgaacagg gatcaggcta tgcagcggat caaaaaagca cacaaaatgc  22620
cattaacggg attacaaaca aggtgaactc tgttatcgag aaaatgaaca ctcaattcac  22680
agctgtgggt aaagaattca acaacttaga aaaaaggatg gaaaatttaa ataaaaaagt  22740
tgatgatggg tttctggaca tttggacata taatgcagaa ttgttagttc tactggaaaa  22800
tgaaaggact ttggatttcc atgacttaaa tgtgaagaat ctgtacgaga aagtaaaaag  22860
ccaattaaag aataatgcca aagaaatcgg aaatgggtgt tttgagttct accacaagtg  22920
tgacaatgaa tgcatggaaa gtgtaagaaa tgggacttat gattatccaa aatattcaga  22980
agaatcaaag ttgaacaggg aaaagataga tggagtgaaa ttggaatcaa tgggggtgta  23040
tcagattctg gcgatctact caactgtcgc cagttcactg gtgcttttgg tctccctggg  23100
ggcaatcagt ttctggatgt gttctaatgg gtctttgcag tgcagaatat gcatctgaga  23160
ttaggatttc agaaatataa ggaaaaacac ccttgtttct actacagacg aacatataag  23220
gcatccgaaa aaaacgttct agtcccatag gcgccgacta ccggcagcgg ctccgacggc  23280
agccgaggtt tacctcgacg taactggagg tacaaaatta cagcgacgcc tctggcagct  23340
ccggagctgt agcgcccccc cccacagcca gagcggccaa gacaatccga aacggggtag  23400
acctggacgc ggatcgcaag ccgccccggc agcgacctct agccgccgcc gcggagagcg  23460
cgagacggta gcacccgggt agaccgttcc gccgtttccg agacgccccg gcagcgaccc  23520
```

-continued

```
ctagccgccg ccgccgcgga gagaccgagc cggacggtgc ccgccgggac caggtagacc  23580

gttccgccgt gccccagcca cctccgcgaa gcgaccga                          23618


<210> SEQ ID NO 61
<211> LENGTH: 482
<212> TYPE: DNA
<213> ORGANISM: Artificial Sequence
<220> FEATURE:
<223> OTHER INFORMATION: GALLUS GALLUS and MUS MUSCULUS

<400> SEQUENCE: 61

tcggtcgctt cgcggaggtg gctggggcac ggcggaacgg tctacctggt cccggcgggc     60

accgtccggc tcggtctctc cgcggcggcg gcggctaggg gtcgctgccg gggcgtctcg    120

gaaacggcgg aacggtctac ccgggtgcta ccgtctcgcg ctctccgcgg cggcggctag    180

aggtcgctgc cggggcggct tgcgatccgc gtccaggtct accccgtttc ggattgtctt    240

ggccgctctg gctgtggggg ggggcgctac agctccggag ctgccagagg cgtcgctgta    300

attttgtacc tccagttacg tcgaggtaaa cctcggctgc cgtcggagcc gctgccggta    360

gtcggcgcct atgggactag aacgtttttt tcggatgcct tatatgttcg tctgtaggag    420

caggtggtac cacctgctgc tcccccccaa cttcggaggt cgaccagtac tccgggcgac    480

ac                                                                   482
```

SINGLE EXPRESSION VECTOR FOR GENERATION OF A VIRUS WITH A SEGMENTED GENOME

GOVERNMENTAL RIGHTS

This invention was made with government support under R01 AI065779 awarded by the National Institutes of Health. The government has certain rights in the invention.

FIELD OF THE INVENTION

The invention encompasses an expression vector and a bacterial carrier. The expression vector is capable of generating a virus after being delivered into host cells. The bacterial carrier of the invention may be utilized to deliver the expression vector into host cells. The virus produced in the host cells from the expression vector may be either attenuated or not attenuated.

BACKGROUND OF THE INVENTION

Influenza virus has caused three recorded pandemics. The 1918 influenza pandemic, also known as Spanish influenza, caused at least 675,000 deaths in the U.S. alone and up to 50 million deaths worldwide (1, 34). The 1957 influenza pandemic caused at least 70,000 deaths in U.S. and 1-2 million deaths worldwide (2, WHO). The 1968 influenza pandemic caused about 34,000 deaths in U.S. and 700,000 deaths worldwide (2, WHO). Since 2003, there were 411 human cases and 256 deaths of avian influenza from 15 countries (WHO). The estimated mortality is more than 60%, making the highly pathogenic H5N1 avian influenza virus a potential candidate for the next influenza pandemic. The economic consequences of such a pandemic due to morbidity and health care delivery would be staggering.

The annual economic burden of influenza epidemics is also enormous. During a typical year in the United States, 30,000 to 50,000 persons die as a result of influenza virus infection, and the global death toll is about 20 to 30 times higher than the toll in this country (26). Based on the 2003 US population, annual influenza epidemics result in an average of 610,660 life-years lost, 3.1 million hospitalized days, and 31.4 million outpatient visits with the total direct medical costs averaging up to $10.4 billion annually. Projected lost earnings due to illness and loss of life amounted to $16.3 billion annually. The total economic burden of annual influenza epidemics using projected statistical life values amounted to $87.1 billion (20). The aforementioned socio-economic factors make influenza one of the critical infectious agents and hence a vaccine to prevent the resulting pandemics is highly warranted.

The three-recorded pandemics and most yearly global outbreaks of influenza are caused by influenza A virus (3, 13, 31, 32, 35). The virus belongs to the family Orthomyxoviridae, and contains a segmented negative-strand RNA genome. Influenza viral RNAs (vRNAs) associate with influenza RNA polymerase complex (PBI, PB2, PA), and nucleoprotein (NP) to make up a set of ribonucleoproteins (RNPs) (14, 21, 25). RNPs are both critical and essential constituents that mediate transcription or replication of vRNA. RNP can be reconstituted in vitro by incubating purified influenza polymerase and nucleoprotein with vRNA transcribed from template DNA (17). The reconstituted RNP has catalytic properties very similar to those of native viral RNP complexes. In the presence of influenza helper virus the recombinant RNP can be amplified and packaged into virus particles in a eukaryotic host cell, a process commonly known as RNP transfection (17) that also enables site-directed mutagenesis of any single component of the influenza virus genome (8). However, the need to select recombinant virus from the mixture of helper viruses and low viral yield demand more sophisticated approaches for the construction of recombinant influenza virus for the production of vaccines that need to be modified annually.

Effort to construct recombinant influenza virus using modern genetic tools for potential application in vaccines has escalated since the early 1990's. The primary objective is to generate influenza virus from plasmid constructs that can be transfected into a broad range of host cells to provide high viral yields with minimum selection from helper virus. In vivo synthesis of vRNA-like molecules was introduced by using RNA polymerase I (Pol I) dependent transcription of viral RNA (24, 37). In a typical plasmid construct, influenza cDNA is inserted precisely between the murine Pol I promoter and terminator sequences. Upon transfection, vRNA synthesized in the cells is bound by influenza polymerase and nucleoprotein that are provided by helper viruses. However, one major disadvantage in this technique is the cumbersome process of selecting recombinant influenza from the mixture containing the helper viruses. By combining intracellular synthesis of vRNAs and proteins, two reverse genetics systems free of helper virus were established by co-transfection of 12-17 plasmids (9, 23). Both systems utilize eight plasmids to encode vRNAs and four plasmids to encode three viral polymerase subunits and a nucleoprotein. The addition of plasmids expressing the remaining viral structural proteins led to a substantial increase in virus production. Thus, limiting the number of plasmid constructs to generate influenza virus still remained a challenge.

The "ambisense" approach that utilizes two promoters on a bidirectional transcription vector is the first major breakthrough to reduce the number of plasmids required for virus generation (11). In this approach, a Pol I promoter drives the synthesis of vRNA from a cDNA template, whereas, RNA polymerase II (Pol II) promoter drives the synthesis of mRNA from the same template in the opposite direction. A system with eight plasmids (i.e., an eight-plasmid system) was developed using the dual promoter technique, which successfully recovered influenza virus from Vero cells (11). A unidirectional Pol I-Pol II transcription system was also reported, however, it suffers from lower viral yield (11). A much-improved method is the generation of influenza virus using a three-plasmid based reverse genetics system (22). Here, one plasmid carries eight Pol I promoter-driven vRNA transcribing cassettes, another plasmid encodes the three viral polymerase subunits and the third plasmid encodes the nucleoprotein. This three-plasmid system, although arduous to construct, yields higher titers of influenza virus than any of the earlier approaches (22). Use of this technique to generate seed for influenza vaccine would thus require two plasmids individually providing HA and NA from epidemic virus, and three plasmid constructs together to provide the remaining components, making it a "2+3" approach.

Vaccines are necessary to prevent influenza outbreaks. To date, the inactivated and attenuated influenza vaccines commercially available for humans are administered either by injection or by nasal-spray. Influenza vaccine seeds are generated by DNA constructs based on reverse genetics system using the "2+6" strategy, where the HA and NA segments are taken from the circulating strain of influenza virus and the remaining 6 structural segments are taken from either the high productive strain PR8 (A/PR/8/34) or the cold-adapted strain (e.g. A/AA/6/60) (4, 10, 12). The current technology in making influenza vaccines relies on using embryonated eggs, which is time-consuming (takes up to four months), has low viral yield and is a cumbersome procedure.

Use of bacterial species to deliver plasmid DNA encoding viral components in the target host cell is an economical and less cumbersome approach to develop vaccines against influenza virus. However, the challenge would be to minimize the number of plasmid constructs so that it would be much easier to ensure the down stream processes involved in virus generation in a eukaryotic host cell.

The above-mentioned factors present a strong need for a single plasmid system for generating influenza virus to develop an inexpensive, ease of manufacture, quickly modifiable and needle-free influenza vaccine. The present invention addresses the design of a single expression vector for generation of virus, and a bacterial carrier based virus generation system, which could be used to develop vaccines against corresponding viral diseases.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
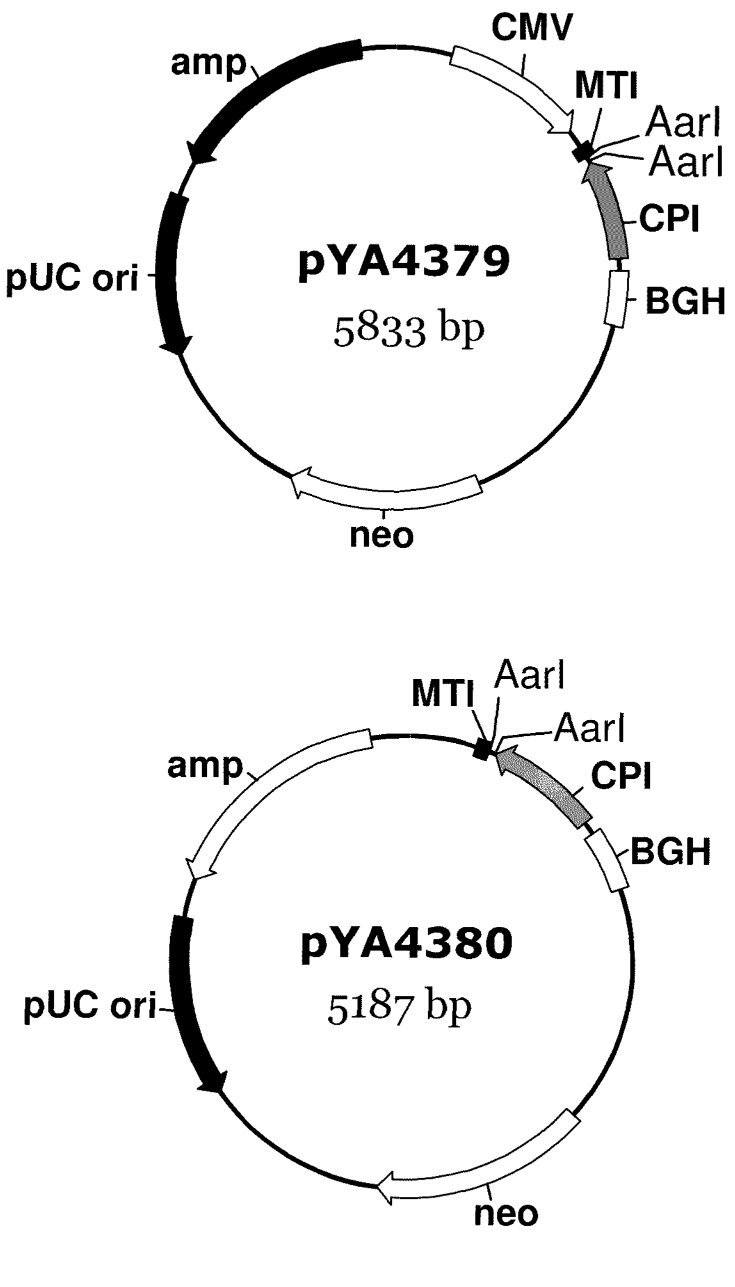
FIG. 1 depicts the construction of plasmids carrying either dual or mono-promoter elements and their derivatives. (A) Chicken Pol I promoter (CPI) and murine Pol I terminator (MTI) that together comprise the Pol I promoter-terminator system were cloned into the HindIII and NheI sites on the eukaryotic expression vector pcDNA3.1(−) that carries CMV promoter and BGH terminator sequences to construct a bi-directional dual promoter plasmid pYA4379 (SEQ ID NO:57) or its variant pYA4380 (SEQ ID NO:58) that lacks the CMV promoter. (B) A 720 bp long EGFP (enhanced green fluorescent protein) gene fragment flanked on the 5' and the 3' ends with non-translating sequences (NTS) from the M segment of WSN virus was cloned into the AarI sites in pYA4379 (SEQ ID NO:57) and the AarI sites in pYA4380 (SEQ ID NO:58) to construct reporter plasmids pYA4387 and pYA4392, respectively. Plasmid pYA4688 was constructed by replacing CPI with Human Pol I promoter (HPI) in pYA4392. Plasmids are not drawn to scale.

A single expression vector capable of generating an attenuated virus from a segmented genome has been developed. An auxotrophic bacterial carrier can carry and deliver this expression vector into in vitro cultured cells, resulting in the recovery of virus, either attenuated or non-attenuated. The invention greatly simplifies the process of producing viruses that have segmented genomes, which historically have required transfection of multiple expression vectors for vRNA expression, in addition to vectors for expressing mRNAs for translation to viral replication proteins. Advantageously, as illustrated in the examples, the expression vector is stable in bacteria at 37° C., and produces higher titers of virus than traditional multi-vector systems when transfected into eukaryotic cells. This invention also demonstrates that bacterial carrier mediated delivery of such an expression vector can lead to the generation of virus. Therefore, this invention provides a system for bacterial carrier based delivery of attenuated viral vaccines with advantages of low cost, ease of manufacture, flexibility in introducing desired alterations, and finally, needle-free administration.

I. Expression Vector

The expression vector generally comprises a plasmid having at least two types of transcription cassettes. One transcription cassette is designed for vRNA production. The other transcription cassette is designed for the production of both vRNAs, and mRNAs. As will be appreciated by a skilled artisan, the number of transcription cassettes, and their placement within the vector relative to each other, can and will vary depending on the segmented virus that is produced. Each of these components of the expression vector is described in more detail below.

The expression vector may be utilized to produce several different segmented and nonsegmented viruses. Viruses that may be produced from the expression vector include positive-sense RNA viruses, negative-sense RNA viruses and double-stranded RNA (ds-RNA) viruses.

In one embodiment, the virus may be a positive-sense RNA virus. Non-limiting examples of positive-sense RNA virus may include viruses of the family Arteriviridae, Caliciviridae, Coronaviridae, Flaviviridae, Picornaviridae, Roniviridae, and Togaviridae. Non-limiting examples of positive-sense RNA viruses may include SARS-coronavirus, Dengue fever virus, hepatitis A virus, hepatitis C virus, Norwalk virus, rubella virus, West Nile virus, Sindbis virus, Semliki forest virus and yellow fever virus.

In one embodiment, the virus may be a double-stranded RNA virus. Non-limiting examples of segmented double-stranded RNA viruses may include viruses of the family Reoviridae and may include aquareovirus, blue tongue virus, coltivirus, cypovirus, fijivirus, idnoreovirus, mycoreovirus, orbivirus, orthoreovirus, oryzavirus, phytoreovirus, rotavirus, infectious bursal disease virus and seadornavirus.

In yet another embodiment, the virus may be a negative-sense RNA virus. Negative-sense RNA viruses may be viruses belonging to the families Orthomyxoviridae, Bunyaviridae, and Arenaviridae with six-to-eight, three, or two negative-sense vRNA segments, respectively. Non-limiting examples of negative-sense RNA viruses may include thogotovirus, isavirus, bunyavirus, hantavirus, nairovirus, phlebovirus, tospovirus, tenuivirus, ophiovirus, arenavirus, deltavirus and influenza virus.

In another aspect, the invention provides an expression vector capable of generating influenza virus. There are three known genera of influenza virus: influenza A virus, influenza B virus and influenza C virus. Each of these types of influenza viruses may be produced utilizing the single expression vector of the invention.

In one exemplary embodiment, the expression vector is utilized to produce Influenza A virus. Influenza A viruses possess a genome of 8 vRNA segments, including PA, PB1, PB2, HA, NP, NA, M and NS, which encode a total of ten to eleven proteins. To initiate the replication cycle, vRNAs and viral replication proteins must form viral ribonucleoproteins (RNPs). The influenza RNPs consist of the negative-sense viral RNAs (vRNAs) encapsidated by the viral nucleoprotein, and the viral polymerase complex, which is formed by the PA, PB1 and PB2 proteins. The RNA polymerase complex catalyzes three different reactions: synthesis of an mRNA with a 5' cap and 3' polyA structure essential for translation by the host translation machinery; a full length complementary RNA (cRNA), and of genomic vRNAs using the cRNAs as a template. Newly synthesized vRNAs, NP and, PB1, PB2 and PA polymerase proteins are then assembled into new RNPs, for further replication or encapsidation and release of progeny virus particles. Therefore, to produce influenza virus using a reverse genetics system, all 8 vRNAs and mRNAs that express the viral proteins essential for replication (NP, PB1, PB1 and PA), must be synthesized. The expression vector of the invention may be utilized to produce all of these vRNAs and mRNAs.

The expression vector may also be utilized to produce any serotype of influenza A virus without departing from the scope of the invention. Influenza A viruses are classified into serotypes based upon the antibody response to the viral surface proteins hemagglutinin (HA or H) encoded by the HA vRNA segment, and neuraminidase (NA or N) encoded by the NA vRNA segment. At least sixteen H subtypes (or serotypes) and nine N subtypes of influenza A virus have been identified. New influenza viruses are constantly being produced by mutation or by reassortment of the 8 vRNA segments when more than one influenza virus infects a single host. By way of example, known influenza serotypes may include H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7 serotypes.

(a) Vector

The expression vector of the invention comprises a vector. As used herein, "vector" refers to an autonomously replicating nucleic acid unit. The present invention can be practiced with any known type of vector, including viral, cosmid, phasmid, and plasmid vectors. The most preferred type of vector is a plasmid vector. As is well known in the art, plasmids and other vectors may possess a wide array of promoters, multiple cloning sequences, and transcription terminators.

The vector may have a high copy number, an intermediate copy number, or a low copy number. The copy number may be utilized to control the expression level for the transcription cassettes, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori. In an alternative embodiment, a low copy number vector may be utilized. For example, a low copy number vector may have one or at least two, three, four, five, six, seven, eight, nine, or ten copies per bacterial cell. A non-limiting example of low copy number vector may be a vector comprising the pSC101 ori. In an exemplary embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

The vector may further comprise a selectable marker. Generally speaking, a selectable marker encodes a product that the host cell cannot make, such that the cell acquires resistance to a specific compound or is able to survive under specific conditions. For example, the marker may code for an antibiotic resistance factor. Suitable examples of antibiotic resistance markers include, but are not limited to, those coding for proteins that impart resistance to kanamycin, spectomycin, neomycin, gentamycin (G418), ampicillin, tetracycline, and chlorampenicol. However, use of selective markers for drug resistance is undesirable for live attenuated bacterial vaccines and delivery systems and is also undesirable for DNA vaccines. Thus in still other cases, the vector might preferably have selectable $Asd^+$, $MurA^+$, $AroA^+$, $DadB^+$, $Alr^+$, $AroC^+$, $AroD^+$, $IlvC^+$ and/or $IlvE^+$ when the expression vector is used in a balanced-lethal or balanced-attenuation vector-host system when present in and delivered by carrier bacteria.

In some embodiments, the vector may also comprise a transcription cassette for expressing non-viral reporter proteins. By way of example, reporter proteins may include a fluorescent protein, luciferase, alkaline phosphatase, beta-galactosidase, beta-lactamase, horseradish peroxidase, and variants thereof.

In some embodiments, the vector may also comprise a DNA nuclear targeting sequence (DTS). A non-limiting example of a DTS may include the SV40 DNA nuclear targeting sequence.

In some embodiments, the vector may also comprise a NF-κB binding site. The SV40 DTS and NF-κB binding sequence facilitate nuclear import of the plasmid DNA, and this facilitates transcription of genetic sequences on the vector.

(b) Transcription Cassettes for vRNAs Expression

The expression vector comprises at least one transcription cassette for vRNA production. Generally speaking, the transcription cassette for vRNA production minimally comprises a Pol I promoter operably linked to a viral cDNA linked to a Pol I transcription termination sequence. In an exemplary embodiment, the transcription cassette will also include a nuclear targeting sequence. The number of transcription cassettes for vRNA production within the expression vector can and will vary depending on the virus that is produced. For example, the expression vector may comprise two, three, four, five, six, seven, or eight or more transcription cassettes for vRNA production. When the virus that is produced is influenza, the expression cassette typically will comprise four transcription cassettes for vRNA production.

The term "viral cDNA", as used herein, refers to a copy of deoxyribonucleic acid (cDNA) sequence corresponding to a vRNA segment of an RNA virus genome. cDNA copies of viral RNA segments may be derived from vRNAs using standard molecular biology techniques known in the art (see, e.g., Sambrook et al. (1989) "Molecular Cloning: A Laboratory Manual," 2nd Ed., Cold Spring Harbor Laboratory Press, Cold Spring Harbor, and Knipe et al (2006) "Fields Virology", Fifth Edition, Lippincott Williams & Wilkins (2007). In some embodiments, the cDNA may be derived from a naturally occurring virus strain or a virus strain commonly used in vitro. In other embodiments, the cDNA may be derived synthetically by generating the cDNA sequence in vitro using methods known in the art. The natural or synthetic cDNA sequence may further be altered to introduce mutations and sequence changes. By way of example, a naturally occurring viral sequence may be altered to attenuate a virus, to adapt a virus for in vitro culture, or to tag the encoded viral proteins.

The selection of promoter can and will vary. The term "promoter", as used herein, may mean a synthetic or naturally derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, may mean that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the nucleic acid sequence it controls. As is known in the art, variation in this distance may be accommodated without loss of promoter function. The promoters may be of viral, prokaryotic, phage or eukaryotic origin. Non-limiting examples of promoters may include T7 promoter, T3 promoter, SP6 promoter, RNA polymerase I promoter and combinations thereof. In some embodiments, the promoters may be different in each transcription cassette. In preferred embodiments, the promoters may be the same in each transcription cassette. In preferred alternatives of this embodiment, the promoters may be RNA polymerase I (Pol I) promoters. In an exemplary alternative of this embodiment, the promoters may be human Pol I promoters. In another exemplary alternative of this embodiment, the promoters may be chicken Pol I promoters. In a further exemplary alternative of this embodiment, the promoters are human Pol I promoters as described in Example 1. In another exemplary alternative of this embodiment, the promoters are chicken Pol I promoters as described in Example 1.

The promoter may be operably linked to the cDNA to produce a negative-sense vRNA or a positive-sense cRNA. In an exemplary alternative of this embodiment, the promoter may be operably linked to the cDNA to produce a negative-sense vRNA.

The transcription cassette also includes a terminator sequence, which causes transcriptional termination at the end of the viral cDNA sequence. By way of a non-limiting example, terminator sequences suitable for the invention may include a Pol I terminator, the late SV40 polyadenylation signal, the CMV polyadenylation signal, the bovine growth hormone polyadenylation signal, or a synthetic polyadenylation signal. In some embodiments, the terminators may be different in each transcription cassette. In a preferred embodiment, the terminators may be the same in each transcription cassette. In one alternative of this embodiment, the Pol I terminator may be a human Pol I terminator. In an exemplary embodiment, the terminator is a murine Pol I terminator. In an exemplary alternative of this embodiment, the terminator sequence of the expression cassettes may be a truncated version of the murine Pol I terminator as described in Example 1.

To function properly during replication, vRNAs transcribed from the transcription cassettes generally have precise 5' and 3' ends that do not comprise an excess of non-virus sequences. Depending on the promoters and terminators used, this may be accomplished by precise fusion to promoters and terminators or, by way of example, the transcription cassette may comprise ribozymes at the ends of transcripts, wherein the ribozymes cleave the transcript in such a way that the sequences of the 5' and 3' termini are generated as found in the vRNA.

As will be appreciated by a skilled artisan, when the expression vector produces influenza virus, the expression vector may comprise at least one transcription cassette for vRNA production. The transcription cassette may be selected from the group consisting of (1) a Pol I promoter operably linked to an influenza virus HA cDNA linked to a Pol I transcription termination sequence; (2) a Pol I promoter operably linked to an influenza virus NA cDNA linked to a Pol I transcription termination sequence; (3) a Pol I promoter operably linked to an influenza virus M cDNA linked to a Pol I transcription termination sequence; and (4) a Pol I promoter operably linked to an influenza virus NS cDNA linked to a Pol I transcription termination sequence. The expression vector may comprise at least 2, 3, or 4 of these transcription cassettes. In an exemplary embodiment, the expression vector will also include either one or two different nuclear targeting sequences (e.g., SV40 DTS and NF-κB binding sequence).

In an exemplary embodiment when the expression vector produces influenza virus, the expression vector will comprise four transcription cassettes for vRNA production. The transcription cassettes for this embodiment will comprise (1) a Pol I promoter operably linked to an influenza virus HA cDNA linked to a Pol I transcription termination sequence; (2) a Pol I promoter operably linked to an influenza virus NA cDNA linked to a Pol I transcription termination sequence; (3) a Pol I promoter operably linked to an influenza virus M cDNA linked to a Pol I transcription termination sequence; and (4) a Pol I promoter operably linked to an influenza virus NS cDNA linked to a Pol I transcription termination sequence. In an exemplary embodiment, the expression vector will also include either one or two different nuclear targeting sequences (e.g., SV40 DTS and NF-κB binding sequence).

(c) Transcription Cassettes for vRNA and mRNA Expression

The expression vector comprises at least one transcription cassette for vRNA and mRNA production. Typically, the transcription cassette for vRNA and mRNA production minimally comprises a Pol I promoter operably linked to a viral cDNA linked to a Pol I transcription termination sequence, and a Pol II promoter operably linked to the viral cDNA and a Pol II transcription termination sequence. In an exemplary embodiment, the transcription cassette will also include a nuclear targeting sequence. The number of transcription cassettes for vRNA and mRNA production within the expression vector can and will vary depending on the virus that is produced. For example, the expression vector may comprise two, three, four, five, six, seven, or eight or more transcription cassettes for vRNA and mRNA production. When the virus that is produced is influenza, the expression cassette typically may comprise four transcription cassettes for vRNA and mRNA production.

The viral cDNA, Pol I promoter and Pol I terminator suitable for producing vRNA is as described above in section (b).

For mRNA production, each transcription cassette comprises a Pol II promoter operably linked to cDNA and a Pol II termination sequence. Non-limiting examples of promoters may include the cytomegalovirus (CMV) promoter, Rous sarcoma virus (RSV) promoter, simian virus 40 (SV40) early promoter, ubiquitin C promoter or the elongation factor 1 alpha (EF1α) promoter. In some embodiments, the promoters may be different in each transcription cassette. In preferred embodiments, the promoters may be the same in each transcription cassette. In preferred alternatives of this embodiment, the promoters may be the CMV Pol II promoter. In an exemplary alternative of this embodiment, the promoters are CMV Pol II promoters as described in Example 1.

Each transcription cassette also comprises a Pol II terminator sequence. By way of non-limiting example, terminator sequences suitable for the invention may include the late SV40 polyadenylation signal, the CMV polyadenylation signal, the bovine growth hormone (BGH) polyadenylation signal, or a synthetic polyadenylation signal. In some embodiments, the terminators may be different in each transcription cassette. In a preferred embodiment, the terminators may be the same in each transcription cassette. In an exemplary embodiment, the terminator is a BGH polyadenylation signal. In an exemplary alternative of this embodiment, the terminator sequence of the expression cassettes may be a truncated version of the BGH polyadenylation signal as described in Example 1.

To function properly in initiating vRNA replication, mRNAs transcribed from the transcription cassettes may contain signals for proper translation by the host cell translation machinery. Most cellular mRNAs transcribed from a Pol II promoter are capped at the 5' end and polyadenylated at the 3' end after transcription to facilitate mRNA translation. However, some cellular mRNAs and many viral mRNAs encode other sequences that facilitate translation of the mRNA in the absence of a 5' cap structure or 3' polyA structure. By way of example, some cellular mRNAs and viral mRNAs may encode an internal ribosomal entry site (IRES), which could functionally replace the 5' cap. By way of another example, some mRNAs and viral mRNAs may encode an RNA structure, such as a pseudoknot, at the 3' end of the mRNA, which could functionally replace the 3' polyA. In an exemplary embodiment, the mRNAs transcribed from the transcription cassettes are capped at the 5' end and polyadenylated at the 3' end.

As will be appreciated by a skilled artisan, when the expression vector produces influenza virus, the expression vector may comprise at least one transcription cassette for vRNA and mRNA production. The transcription cassette may be selected from the group consisting of (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a Pol I transcription termination sequence and a Pol II promoter operably linked to the NP cDNA and a Pol II transcription termination sequence. The expression vector may comprise at least 2, 3, or 4 of these transcription cassettes. In an exemplary embodiment, the expression vector will also include either one or two different nuclear targeting sequences (e.g., SV40 DTS or NF-κB binding sequence).

In an exemplary embodiment when the expression vector produces influenza virus, the expression vector will comprise four transcription cassettes for vRNA and mRNA production. The transcription cassettes for this embodiment will comprise (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a Pol I transcription termination sequence and a Pol II promoter operably linked to the NP cDNA and a Pol II transcription termination sequence. In an exemplary embodiment, each expression plasmid construct will also include either one or two different nuclear translocation signals (e.g., SV40 DTS or NF-κB binding sequence).

(d) Exemplary Expression Vectors

In an exemplary iteration of the invention, a single expression vector will comprise all of the genomic segments necessary for the production of influenza virus in a host cell. As detailed above, for the production of influenza virus HA, NA, NS, and M vRNA must be produced and PA, PB1, PB2, and NP vRNA and mRNA must be produced. For this iteration, the expression vector will comprise four transcription cassettes for vRNA production and four transcription cassettes for vRNA and mRNA production. The four cassettes for vRNA production will comprise (1) a Pol I promoter operably linked to an influenza virus HA cDNA linked to a Pol I transcription termination sequence; (2) a Pol I promoter operably linked to an influenza virus NA cDNA linked to a Pol I transcription termination sequence; (3) a Pol I promoter operably linked to an influenza virus M cDNA linked to a Pol I transcription termination sequence; and (4) a Pol I promoter operably linked to an influenza virus NS cDNA linked to a Pol I transcription termination sequence. The four transcription cassettes for vRNA and mRNA production will comprise (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a Pol I transcription termination sequence and a Pol II promoter operably linked to the NP cDNA and a Pol II transcription termination sequence. The expression vector will preferably also include either one or two different nuclear translocation signals (e.g., SV40 DTS or NF-κB binding sequence). In an exemplary embodiment, the vector is a plasmid. The plasmid will generally be a low or intermediate copy number plasmid. A particularly exemplary expression vector for this embodiment is detailed in the Examples.

The arrangement and direction of transcription cassettes within the single expression vector relative to each other can and will vary without departing from the scope of the invention. It is believed, however, without being bound by any particular theory that arrangement of transcription cassettes in pairs of vRNA cassettes and vRNA and mRNA cassettes is preferable because it may reduce the degree of recombination and as a result, yield an expression vector with increased genetic stability.

It is also envisioned that in certain embodiments, influenza genomic segments may be produced from more than a single expression vector without departing from the scope of the invention. The genomic segments may be produced, for example, from 2, 3, or 4 or more different expression vectors. In an iteration of this embodiment, NS, and M vRNA, and PA, PB1, PB2, and NP vRNA and mRNA are produced from a single expression vector. For this iteration, the expression vector will comprise two transcription cassettes for vRNA production and four transcription cassettes for vRNA and mRNA production. The two transcription cassettes for vRNA production will comprise (1) a Pol I promoter operably linked to an influenza virus M cDNA linked to a Pol I transcription termination sequence; and (2) a Pol I promoter operably linked to an influenza virus NS cDNA linked to a Pol I transcription termination sequence. The four transcription cassettes for vRNA and mRNA production will comprise (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a Pol I transcription termination sequence and a Pol II promoter operably linked to the NP cDNA and a Pol II transcription termination sequence. The expression of HA vRNA and NA vRNA may be from a single expression vector that comprises two transcription cassettes comprising (1) a Pol I promoter operably linked to an influenza virus HA cDNA linked to a Pol I transcription termination sequence; and (2) a Pol I promoter operably linked to an influenza virus NA cDNA linked to a Pol I transcription termination sequence. Alternatively, expression of HA vRNA and NA vRNA may be from two separate expression vectors.

In some embodiments, restriction digestion sites may be placed at convenient locations in the expression vector. By way of example, restriction enzyme sites placed at the extremities of the cDNAs may be used to facilitate replacement of cDNA segments to produce a desired reassortment or strain of the virus. By way of another example, restriction enzyme sites placed at the extremities of the transcription cassettes may be used to facilitate replacement of transcription cassettes to produce a desired reassortment or strain of the virus. Suitable, endonuclease restriction sites include sites that are recognized by restriction enzymes that cleave double-stranded nucleic acid. By way of non-limiting example, these sites may include AarI, AccI, AgeI, Apa, BamHI, BglI, BglII, BsiWI, BssHI, BstBI, ClaI, CviQI, DdeI, DpnI, DraI, EagI, EcoRI, EcoRV, FseI, FspI, HaeII, HaeIII, HhaI, HincII, HindIII, HpaI, HpaII, KpnI, KspI, MboI, MfeI, NaeI, NarI, NcoI, NdeI, NgoMIV, NheI, NotI, PacI, PhoI, PmlI, PstI, PvuI, PvuII, SacI, SacII, SalI, SbfI, SmaI, SpeI, SphI, SrfI, StuI, TaqI, TfiI, TliI, XbaI, XhoI, XmaI, XmnI, and ZraI. In an exemplary alternative of this embodiment, the restriction enzyme site may be AarI.

II. Bacterial Carrier

An additional aspect of the invention comprises a bacterial carrier that can carry and deliver the expression vector described in Section I into a host cell. The host cell may be in vitro (i.e., cultured cells) or in vivo (e.g., an animal) as described in more detail in section III below. The bacterial carrier is typically auxotrophic and may be either a Gram-positive bacterium or Gram-negative bacterium. In this context, the bacterial carrier generally carries at least one gene mutation for an auxotrophic phenotype to enable intracellular release of the expression vector, and at least one gene mutation to enable stable carriage of the expression vector and at least one mutation to impose appropriate attenuation and for other desirable phenotypes such as for escaping the endosome in a eukaryotic cell. Additionally, the bacterial carrier may be a live bacterium or a bacterial ghost. In addition, the bacterial carrier may be attenuated. The bacterial carrier may also carry additional plasmid vectors for better invasion efficiency or for regulated delayed lysis in vivo. Preferably, the bacterial carrier is sensitive to all antimicrobial drugs including antibiotics that might be useful in treating infections with wild-type variants of the particular bacterial carrier being used to deliver the plasmid vector to eukaryotic cells.

As will be appreciated by a skilled artisan, the bacterial carrier may be utilized to deliver a single expression vector or to deliver multiple expression vectors. The single expression vector may encode information for generation of a segmented virus or non-segmented virus; for instance, the expression vector can encode 8 vRNAs, 3 polymerase subunits and nucleoprotein of influenza virus.

Alternatively, the bacterial carrier may be utilized to deliver multiple expression vectors. For example, one p15A ori based expression vector encodes PB2, PB1, PA and NP genes, and the other pBR ori based expression vector encodes HA, NA, M and NS genes.

In yet another embodiment, the bacterial carrier may be utilized to deliver an expression vector for virus generation. For example, the expression vector pYA4519 encodes 8 vRNAs, 3 polymerase subunits and nucleoprotein of influenza virus.

In one embodiment, the bacterial carrier may be utilized to deliver an expression vector in vitro. For instance, the expression vector encodes 8 vRNAs, 3 polymerase subunits and nucleoprotein of influenza virus.

In an alternative embodiment, the bacterial carrier may be utilized to deliver an expression vector in vivo. For example, oral administration with an auxotrophic, attenuated *Salmonella Typhimurium* carrying pYA4930 designed for regulated delayed lysis to deliver pYA4930 into avians.

In one embodiment, the bacterial carrier may be utilized to deliver an expression vector to humans. By way of non-limiting example, the expression vector encodes HA and NA from epidemic influenza virus, and the other 6 segments from cold-adapted influenza virus (e.g. A/AA/6/60). The polybasic cleavage site in HA will be removed to avoid the generation of reassortant virulent virus in the host. In this embodiment, the vRNAs transcription is regulated by human RNA Pol I promoters, and the transcription of mRNAs is regulated by CMV promoters.

In another embodiment, the bacterial carrier may be utilized to deliver expression vectors into other animals. For example, the expression vector encodes HA and NA from a highly pathogenic avian influenza virus (polybasic cleavage site in HA will be removed to avoid the generation of reassortant virulent virus in the host), and the other 6 segments from a cold-adapted influenza virus (e.g. A/AA/6/60).

In each of the foregoing embodiments, the bacterial carrier may be designed to have host-specificity for and be utilized for primates (e.g., humans, monkeys, chimpanzies etc), poultry (e.g., chickens, turkeys, ducks, geese and other fowl), ruminants (e.g., beef cattle, dairy cattle, and sheep, etc), pigs, and companion animals (e.g., horses, dogs, cats, and other pets).

As will be appreciated by a skilled artisan, suitable bacterial carriers may comprise several different bacterial strains to the extent the bacterial strain is capable of maintaining and delivering an expression vector to a host cell. By way of non-limiting example, the bacterial strain may be Gram-negative bacteria, including *Salmonella* spp., *Shigella* spp, *Yersinia* spp., and engineered *Escherichia coli* expressing an invasin gene. In a preferred alternative of this embodiment, the bacterium may be a *Salmonella enterica* serovar. In one alternative of this embodiment, the bacterium may be a *Salmonella enterica* serovar Abortusovis. In another alternative of this embodiment, the *Salmonella bacterium* may be *Salmonella enterica* serovar Typhi. In a preferred embodiment, the bacterium may be a *Salmonella enterica* serovar *Typhimurium* (*Salmonella Typhimurium*). In an exemplary alternative of this embodiment, the *Salmonella Typhimurium* strain is $\chi$9052 (ΔasdA33 Δalr-3 ΔdadB4). In other exemplary alternatives of this embodiment, the *Salmonella Typhimurium* strain is $\chi$11017 (ΔasdA27::TT araC $P_{BAD}$ c2 ΔaraBAD23 Δ(gmd-fcl)-26 Δpmi-2426 ΔrelA198::TT araC $P_{BAD}$ lacI $\Delta P_{murA25}$::araC $P_{BAD}$ murA) or $\chi$11327 (ΔasdA27::TT araC $P_{BAD}$ c2 $\Delta P_{murA25}$::TT araC $P_{BAD}$ murA ΔaraBAD23 Δ(gmd-fcl)-26 ΔrelA198::araC $P_{BAD}$ lacI TTΔpmi-2426 ΔtlpA181 ΔsseL116 $\Delta P_{hilA}$::$P_{trc\ \Delta lacO888}$ hilA ΔsifA26).

In an alternative of this embodiment, the *Salmonella Typhimurium* strains may also comprise deletions of the bacterial nucleic acid sequences recA62, recF126 or both. In an alternative of this embodiment, the *Salmonella Typhimurium* strains may also comprise a deletion of the bacterial nucleic acid sequence for the aroA gene to result in the aroA21419 mutation.

Alternatively, the bacterial strain may be Gram-positive bacteria. By way of non-limiting example, one suitable Gram-positive bacterium is *Listeria monocytogenes*.

In certain embodiments, the bacterial carrier may be attenuated. By way of example, the bacterial carrier may be live bacteria with appropriate attenuation due to a phoP mutation or other means of attenuation if the carrier is derived from a pathogenic bacterium capable of causing disease. In yet another embodiment, the bacterial carrier may be bacteria with a regulated delayed lysis genotype, such as araC $P_{BAD}$ promoter regulated expression of the murA gene. The live bacteria carrying an expression vector may be induced to express a phage lysis gene E or some other lysis gene to form bacterial ghosts.

In an alternative embodiment, the bacterial carrier may carry a mutation in at least one gene for an auxotrophic phenotype. For example, these genes include, but are not limited to aroA, aroC, aroD, llvC, llvE, asd, murA, dadB, and alr.

In certain embodiments to facilitate stable carriage of an expression vector with repetitive sequences, either recA or recF gene inactivation may be included to reduce either intra- or inter-plasmid recombination.

In certain embodiments the bacterial carrier may carry a sifA mutation to facilitate escape from the endosome.

In other embodiments the bacterial carrier may carry an endA mutation to minimize chances of endonuclease digestion of the expression vector.

Several methods generally known in the art utilized to attenuate a bacterial carrier may be employed without departing from the scope of the invention. Suitable non-limiting examples of such attenuation means include gene mutations in phoP, phoQ, cya, crp, cdt, an aro gene, asd, a dap gene, dadB and alr, murA, nadA, pncB, rpsL, ilvE, rpoS, ompR, htrA, rfc, poxA, dam, hemA, sodC, recA, ssrA, sirA, inv, hilA, rpoE, flgM, tonB, slyA, pmi, galE, galU, mviA, rfaH, a pur gene, a pab gene, and fur.

In a further embodiment, the bacterial carrier may also comprise additional plasmid vectors for improving its invasion efficiency. For example, a plasmid expressing the gene encoding invasin from *Yersinia pseudotuberculosis.*

In an additional embodiment, the bacterial carrier may comprise additional plasmid vectors for regulated lysis in vivo. For example, the plasmid pYA3681 (araC $P_{BAD}$ promoter regulates expression of asd and murA genes) in strain χ11020.

III. Methods for Producing a Segmented Virus

The expression vector detailed in section (I) may be utilized to produce a segmented virus in vitro or in vivo. Depending upon the intended use, the resulting virus may, by way of example, be purified, attenuated or inactivated. In some embodiments, the virus is purified and used as a seed virus for further production of virus. In other embodiments, the virus is attenuated for use in a vaccine composition. In yet other embodiments, the virus is inactivated for use in a vaccine composition.

In one aspect, the invention provides a method for producing a virus by introducing the expression vector into a eukaryotic cell. The expression vector may be delivered to the cell using transfection. Methods for transfecting nucleic acids are well known to individuals skilled in the art. Transfection methods include, but are not limited to, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, DreamFect, or ExGen 500.

The expression vector may also be delivered to the cell using a viral vector. Viral vectors suitable for introducing nucleic acids into cells include retroviruses, vaccinia viruses, adenoviruses, adeno-associated viruses, rhabdoviruses, and herpes viruses.

In some embodiments, the expression vector may be introduced into eukaryotic tissue culture cells in vitro. Non-limiting examples of eukaryotic cells used for virus production in vitro may include human embryonic kidney 293 (HEK293) cells, Madin-Darby canine kidney (MDCK) cells, chicken embryonic fibroblasts (CEFs), African green monkey kidney epithelial (vero) cells, or any variants or combinations thereof. In all such cases, the sequences in all expression cassettes recognized by RNA polymerase I would have to be changed to possess DNA sequences recognized by the RNA polymerase I from the species of animal for the particular cell line. This is because RNA polymerase I are species specific. In a preferred embodiment, the expression vector may be introduced into HEK293 cells. In another preferred embodiment, the expression vector may be introduced into a mixture of CEFs and MDCK cells. Upon introduction of the expression vector into the eukaryotic cells, the host cells may then be cultured under conditions that permit production of viral proteins and vRNAs using tissue culture techniques known in the art. By way of non-limiting example, the expression vector, when introduced into a tissue culture cell, yields $10^8$ PFU/ml or more of influenza virus after 6 days.

In other aspects, the expression vector may be introduced into a eukaryotic cell in an animal. Non-limiting examples of animals where the expression vector may be introduced may include humans, horses, pigs, chickens, ducks, and geese. Methods of delivery of the expression vector to a eukaryotic cell may be as described above.

Alternatively, and in a preferred embodiment of the invention, the expression vector may be delivered into the eukaryotic cell via a carrier bacterium as described in Section II. The carrier bacteria typically deliver the expression vector into the eukaryotic cell cytoplasm. Suitable carrier bacteria are described in more detail in Section II.

In yet other aspects, bacterial carrier mediated expression vector delivery can be used to generate several different groups of viruses, including positive-sense RNA viruses, negative-sense RNA viruses and double-stranded RNA (dsRNA) viruses. Non-limiting examples of positive-sense RNA virus include viruses of the family Arteriviridae, Caliciviridae, Coronaviridae, Flaviviridae, Picornaviridae, Roniviridae, and Togaviridae. Non-limiting examples of positive-sense RNA viruses may include SARS-coronavirus, Dengue fever virus, hepatitis A virus, hepatitis C virus, Norwalk virus, rubella virus, West Nile virus, Sindbis virus, Semliki forest virus and yellow fever virus. Non-limiting examples of double-stranded RNA viruses may include viruses of the family Reoviridae and may include aquareovirus, coltivirus, cypovirus, fijivirus, idnoreovirus, mycoreovirus, orbivirus, orthoreovirus, oryzavirus, phytoreovirus, rotavirus, infectious bursal disease virus and seadornavirus. Negative-sense RNA viruses may be viruses belonging to the families Orthomyxoviridae, Bunyaviridae, and Arenaviridae with six-to-eight, three, or two negative-sense vRNA segments respectively. Non-limiting examples of negative-sense RNA viruses may include thogotovirus, isavirus, bunyavirus, hantavirus, nairovirus, phlebovirus, tospovirus, tenuivirus, ophiovirus, arenavirus, deltavirus and influenza virus.

In some embodiments, the bacterial carriers are attenuated as detailed in Section II. As previously described, the bacterial carrier may carry one or more mutations for this purpose. Non-limiting examples are the phoP mutation and the pmi mutation. The bacterial carrier may carry one plasmid to express a lysis gene. Non-limiting example is phage lysis gene E expressing plasmid. The bacterial carrier may carry one plasmid, which complement the mutations on the bacterial carrier chromosome to form a regulated delayed lysis system. For example, χ11020 carrying plasmid pYA3681.

In some embodiments, the expression vector may be modified for generation of attenuated virus. The strategies include, but not limiting to (1) using an attenuated virus genome to construct the single expression vector. For example, using HA and NA from epidemic influenza virus and the other segments from attenuated cold-adapted influenza virus (e.g. A/AA/6/60). Meanwhile the polybasic cleavage site has to be removed from the HA protein. (2) Introducing mutations into viral genes to change the protein sequence. For example, introducing mutations into epidemic influenza virus by reverse genetics to attenuate it, so that the generated virus can be used as vaccine seed. The mutations include (i) removing the polybasic cleavage site from HA protein, (ii) truncating the C-terminal end of the NS1 protein, (iii) and introducing mutations into viral polymerase.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The term “cRNA” refers to a positive-sense RNA copy of a vRNA.

The term “vRNA” refers to a negative-sense genomic viral RNA.

The term “vaccine composition” as used herein means a composition that when administered to a host, typically elicits an immune response against the virus. Such compositions are known in the art.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods for Examples 1-4

Bacterial Strains, Enzymes, Plasmids and Primers

EPI300™ chemically competent *E. coli* (Epicentre) was used for all DNA cloning experiments. Restriction enzyme SrfI was bought from Stratagene (La Jolla, Calif.). All other restriction enzymes were from New England Biolabs (Ipswich, Mass.). Plasmids pTM-Pol I-WSN-All and pCAWS-NP were kindly provided by Dr. Yoshihiro Kawaoka (University of Wisconsin—Madison). Plasmid pYS1190 and pIRES-EGFP were gifts from Dr. Yixin Shi (Arizona State University). Primers used in this study are listed in Table 2. Plasmid constructs used in this study are listed in Table 1.

TABLE 1

Plasmid constructs used in this study.

| Plasmid | Properties | Reference |
|---|---|---|
| pcDNA3.1(-) | Eukaryotic expression vector carrying a CMV promoter and bovine growth hormone polyadenylation signal | Invitrogen |
| pIRES-EGFP | Source of the EGFP gene | Clontech |
| pYS1190 | Source of the mCherry gene | Unpublished |
| pTM-PolI-WSN-All | An 8-unit-plasmid for transcribing PB1, PB2, NS, M, NA, PA, NP, HA vRNAs under human Pol I promoter | -22 |
| pCAWS-NP | Eukaryotic expression of nucleoprotein (NP) used as helper plasmid | -22 |
| pYA3994 | A pBR ori containing plasmid containing GFP gene flanked by $P_{trc}$ promoter and 5ST1T2 terminator | Lab collection |
| pYA4464 | Vector with p15A ori sequence and cat cassette | Lab collection |
| pYA4749 | A GFP expression vector with a p15A ori constructed by fusing DNA segments from pYA3994 and pYA4464 | This study |
| pYA4337 | Gene encoding PB2 inserted into pcDNA3.1(-) | This study |
| pYA4338 | Gene encoding PB1 inserted into pcDNA3.1(-) | This study |
| pYA4339 | Gene encoding PA inserted into pcDNA3.1(-) | This study |
| pYA4379 | Chicken Pol I promoter (CPI) and murine Pol I terminator (MTI) cloned into pcDNA3.1(-) to create a bidirectional vector to synthesize vRNA from CPI and mRNA from CMV promoter | This study |
| pYA4383 | PB2 cDNA cloned into pYA4379 to synthesize mRNA by CMV promoter and vRNA by CPI | This study |
| pYA4384 | PB1 cDNA cloned into pYA4379 to synthesize mRNA by CMV promoter and vRNA by CPI | This study |
| pYA4385 | PA cDNA cloned into pYA4379 to synthesize mRNA by CMV promoter and vRNA by CPI | This study |
| pYA4386 | NP cDNA cloned into pYA4379 to synthesize mRNA by CMV promoter and vRNA by CPI | This study |
| pYA4387 | EGFP gene cloned into pYA4379 to synthesize mRNA by CMV promoter and antisense RNA (vRNA-like) by CPI | This study |
| pYA4380 | CPI and MTI cloned into modified pcDNA3.1 (-) to synthesize vRNA | This study |
| pYA4388 | HA cDNA inserted into the AarI sites in pYA4380 to synthesize vRNA by CPI | This study |
| pYA4389 | NA cDNA cloned in pYA4380 to synthesize vRNA by CPI | This study |
| pYA4390 | M cDNA cloned in pYA4380 to synthesize vRNA by CPI | This study |
| pYA4391 | NS cDNA cloned in pYA4380 to synthesize vRNA by CPI | This study |
| pYA4392 | EGFP gene cloned into pYA4380 to transcribe antisense RNA (vRNA-like) by CPI | This study |

TABLE 1-continued

| Plasmid constructs used in this study. | | |
|---|---|---|
| Plasmid | Properties | Reference |
| pYA4688 | CPI replaced with human Pol I promoter in pYA4380 to transcribe EGFP gene into antisense RNA (vRNA-like) | This study |
| pYA4519 | 8 influenza cDNA cassettes cloned into one plasmid to synthesize vRNAs by CPI and PB2, PB1, PA and NP mRNA/protein by CMV promoter | This study |
| pYA4731 | The mCherry gene cloned in between CMV and BGH-polyA terminator in pcDNA3.1(-) | This study |
| pYA4732 | The CMV-mCherry-BGH-polyA cassette from pYA4731 inserted in the SrfI site on pYA4519 | This study |

TABLE 2

| Primers used in this study | | | |
|---|---|---|---|
| Primer Name | SEQ ID | Sequence | Application |
| CP1 | 1 | 5'-tcggtcgcttcgcggaggtggctgg-3' | Clone chicken RNA Pol I promoter from genomic DNA |
| CP2 | 2 | 5'-gtgatcgccttctccggctttttt-3' | Clone chicken RNA Pol I promoter from genomic DNA |
| PI-1 | 3 | 5'-taaaagctttctgcagaattcgccctt-3' | Amplify chicken RNA Pol I promoter (nt -415 to -1) |
| PI-2 | 4 | 5'-ttaggtaccacctgctcctacagacgaac-3' | Amplify chicken RNA Pol I promoter (nt -415 to -1) |
| TI-1 | 5 | 5'-taaggtaccacctgctgctccccccaacttc-3' | Amplify murine Pol I terminator (41bp) |
| TI-3 | 6 | 5'-ttagctagcgtgtcgcccggagta-3' | Amplify murine Pol I terminator (41bp) |
| BsmBI-EGFP1 | 7 | 5'-taacgtctctctgtagtagaaacaagg tagtttttttacttgtacagctcg-3' | Add nontranslational sequence of M segment to EGFP gene |
| BsmBI-EGFP2 | 8 | 5'- ttacgtctctggggagcaaaagcaggtagatattg aaagatggtgagcaagggcg-3' | Add nontranslational sequence of M segment to EGFP gene |
| FP-cherry | 9 | 5'-acctctagaatggtgagcaagggcgag-3' | Clone mCherry gene into pcDNA31(−) |
| RP-cherry | 10 | 5'-taagaattcttacttgtacagctcgtc-3' | Clone mCherry gene into pcDNA31(−) |
| P1 | 11 | 5'-taactcgagatggaaagaataaaag-3' | Clone PB2 ORF into pcDNA3.1(−) |
| P2 | 12 | 5'-ttaggtaccctaattgatggccatc-3' | Clone PB2 ORF into pcDNA3.1(−) |
| P3 | 13 | 5'-taactcgagatggatgtcaatccga-3' | Clone PB1 ORF into pcDNA3.1(−) |
| P4 | 14 | 5'-ttaggtaccctatttttgccgtctg-3' | Clone PB1 ORF into pcDNA3.1(−) |
| P5 | 15 | 5'-taactcgagatggaagatttgtgc-3' | Clone PA ORF into pcDNA3.1(−) |
| P6 | 16 | 5'-ttaggtaccctatctcaatgcatgt-3' | Clone PA ORF into pcDNA3.1(−) |
| AarI-PB2-1 | 17 | 5'-taacacctgcagtcctgtagtagaaacaaggtcgt-3' | Clone PB2 cDNA into pYA4379 |
| AarI-PB2-2 | 18 | 5'-ttacacctgcgactggggagcgaaagcaggtcaat-3' | Clone PB2 cDNA into pYA4379 |
| AarI-PB1-1 | 19 | 5'-taacacctgcagtcctgtagtagaaacaaggcatt-3' | Clone PB1 cDNA into pYA4379 |
| AarI-PB1-2 | 20 | 5'-ttacacctgcgactggggagcgaaagcaggcaaac-3' | Clone PB1 cDNA into pYA4379 |
| BsmBI-PA-1 | 21 | 5'-taacgtctctctgtagtagaaacaaggtact-3' | Clone PA cDNA into pYA4379 |
| BsmBI-PA-2 | 22 | 5'-ttacgtctctggggagcgaaagcaggtactg-3' | Clone PA cDNA into pYA4379 |
| BsmBI-NP-1 | 23 | 5'-taacgtctctctgtagtagaaacaagggtat-3' | Clone NP cDNA into pYA4379 |
| BsmBI-NP-2 | 24 | 5'-ttacgtctctggggagcaaaagcagggtaga-3' | Clone NP cDNA into pYA4379 |

TABLE 2-continued

| Primers used in this study | | | |
|---|---|---|---|
| Primer Name | SEQ ID | Sequence | Application |
| BsmBI-HA-1 | 25 | 5'-taacgtctctctgtagtagaaacaagggtg-3' | Clone HA cDNA into pYA4380 |
| BsmBI-HA-2 | 26 | 5'-ttacgtctctggggagcaaaagcaggggaa-3' | Clone HA cDNA into pYA4380 |
| AarI-NA-1 | 27 | 5'-taacacctgcagtcctgtagtagaaacaaggagtt-3' | Clone NA cDNA into pYA4380 |
| AarI-NA-2 | 28 | 5'-ttacacctgcgactggggagcgaaagcaggagttt-3' | Clone NA cDNA into pYA4380 |
| BsmBI-M-1 | 29 | 5'-taacgtctctctgtagtagaaacaaggtagt-3' | Clone M cDNA into pYA4380 |
| BsmBI-M-2 | 30 | 5'-ttacgtctctggggagcaaaagcaggtagat-3' | Clone M cDNA into pYA4380 |
| BsmBI-NS-1 | 31 | 5'-taacgtctctctgtagtagaaacaagggtgt-3' | Clone NS cDNA into pYA4380 |
| BsmBI-NS-2 | 32 | 5'-ttacgtctctggggagcaaaagcagggtgac-3' | Clone NS cDNA into pYA4380 |
| SrfI-PB2 | 33 | 5'-taagcccgggcgttgacattgattattg-3' | Amplify PB2 dual promoter cassette |
| NgoMIV-NotI-PB2 | 34 | 5'-ttagccggcttagcggccgccatagagcccaccgcat-3' | Amplify PB2 dual promoter cassette |
| BssHII-PB1 | 35 | 5'-taagcgcgcgttgacattgattattgac-3' | Amplify PB1 dual promoter cassette |
| NgoMIV-SbfI-PB1 | 36 | 5'-ttagccggcttacctgcaggccatagagcccaccgca-3' | Amplify PB1 dual promoter cassette |
| KpnI-PA | 37 | 5'-taaggtaccgttgacattgattattgac-3' | Amplify PA dual promoter cassette |
| NgoMIV-PacI-PA | 38 | 5'-ttagccggcttattaattaaccatagagcccaccgca-3' | Amplify PA dual promoter cassette |
| ApaI-NP* | 39 | 5'-taagggcccgttgacattgattattgac-3' | Amplify NP dual promoter cassette |
| NgoMIV-PmII-NP* | 40 | 5'-ttagccggcttacacgtgccatagagcccaccgcatc-3' | Amplify NP dual promoter cassette |
| PmII-HA | 41 | 5'-taacacgtggtgtcgcccggagtactgg-3' | Amplify HA mono promoter cassette |
| NgoMIV-HA | 42 | 5'-ttagccggctcggtcgcttcgcggaggt-3' | Amplify HA mono promoter cassette |
| PacI-NA | 43 | 5'-taattaattaagtgtcgcccggagtact-3' | Amplify NA mono promoter cassette |
| NgoMIV-NA | 44 | 5'-ttagccggcttagggccctcggtcgcttcgcggag-3' | Amplify NA mono promoter cassette |
| SbfI-M | 45 | 5'-taacctgcagggtgtcgcccggagtact-3' | Amplify M mono promoter cassette |
| NgoMIV-M | 46 | 5'-ttagccggcttaggtacctcggtcgcttcgcggag-3' | Amplify M mono promoter cassette |
| NotI-NS | 47 | 5'-taagcggccgcgtgtcgcccggagtact-3' | Amplify NS mono promoter cassette |
| NgoMIV-NS | 48 | 5'-ttagccggcttagcgcgctcggtcgcttcgcggag-3' | Amplify NS mono promoter cassette |

*also used to amplify CMV-mCherry-BGH cassette from pYA4731 to construct pYA4732

Cell Culture.

Chicken embryonic fibroblasts (CEFs) were prepared by standard trypsinization of decapitated 8-day old embryos. CEFs, human embryonic kidney (HEK293) cells and Madin-Darby canine kidney (MDCK) cells were maintained in Dulbecco's modified Eagle's medium (DMEM) supplemented with 10% fetal bovine serum (FBS), 100 U/ml penicillin and 100 μg/ml streptomycin. To co-culture CEFs and MDCK cells, each cell type was grown in 75 $cm^2$ flasks, trypsinized, and ⅓ volume of each was mixed with growth media to a total volume of 40 ml. The mixed cells were seeded into six-well plates at 3 ml per well. All cells were maintained at 37° C. in 5% $CO_2$.

Construction of Chicken Pol I Promoter-Based Reporter plasmids.

Plasmid pcDNA3.1(−) (Invitrogen, Carlsbad, Calif.) carrying the cytomegalovirus (CMV) promoter and the bovine growth hormone (BGH) polyadenylation signal that together form the Pol II promoter-terminator system, was used to construct vector pYA4379 (SEQ ID NO:57). Briefly, chicken Pol I promoter (CPI) was cloned from chicken genomic DNA (18). The truncated murine Pol I terminator (MTI) was amplified from plasmid pTM-Pol I-WSN-All. Using unique enzyme sites introduced by PCR, CPI region (nt: −415 to −1) and MTI (41 bp) were connected with KpnI site to produce SEQ ID NO:61 (Table 3), and placed between NheI and HindIII on pcDNA3.1(−) downstream of the CMV promoter to construct the bidirectional transcription vector pYA4379 (SEQ ID NO:57) (FIG. 1A). The two AarI sites introduced inbetween CPI and MTI will allow cloning of an insert without introducing any additional nucleotides at either end. Plasmid pYA4380 (SEQ ID NO:58) was constructed by excising the CMV promoter fragment from pcDNA3.1(−) using enzymes SpeI and HindIII followed by insertion of the CPI-MTI fusion product (FIG. 1A).

TABLE 3

| Sequence of fused CPI and MTI. Sequence of chicken RNA polymerase I promoter (CPI) is underlined and sequence of murine Pol I terminator (MTI) is given in bold. Sequence of two AarI sites is highlighted with gray background. | |
|---|---|
| SEQ ID NO: 61 | TCGGTCGCTTCGCGGAGGTGGCTGGGGCACGGCGGAAC<br>GGTCTACCTGGTCCCGGCGGGCACCGTCCGGCTCGGTC<br>TCTCCGCGGCGGCGGCGGCTAGGGGTCGCTGCCGGGG<br>CGTCTCGGAAACGGCGGAACGGTCTACCCGGGTGCTAC<br>CGTCTCGCGCTCTCCGCGGCGGCGGCTAGAGGTCGCTG<br>CCGGGGCGGCTTGCGATCCGCGTCCAGGTCTACCCCGT<br>TTCGGATTGTCTTGGCCGCTCTGGCTGTGGGGGGGGGC<br>GCTACAGCTCCGGAGCTGCCAGAGGCGTCGCTGTAATTT<br>TGTACCTCCAGTTACGTCGAGGTAAACCTCGGCTGCCGT<br>CGGAGCCGCTGCCGGTAGTCGGCGCCTATGGGACTAGA<br>ACGTTTTTTTCGGATGCCTTATATGTTCGTCTGTAGGAGC<br>AGGTGGTACCACCTGCTGCT**CCCCCCCAACTTCGGAGGT**<br>**CGACCAGTACTCCGGGCGACAC** |

Figure 1B:
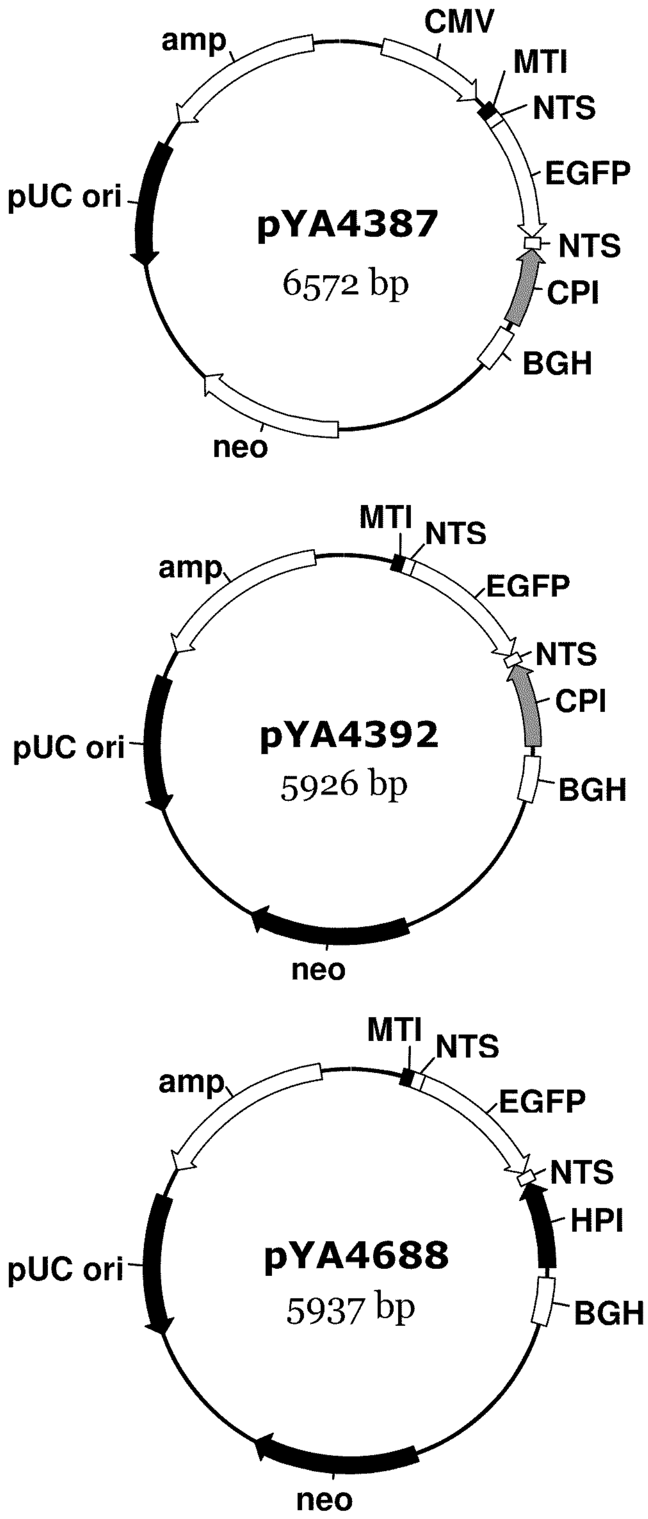

Plasmid pIRES-EGFP (Clontech; Mountain View, Calif.) was the source of the enhanced green fluorescent protein (EGFP) gene used to measure promoter activities in plasmids pYA4379 (SEQ ID NO:57) and pYA4380 (SEQ ID NO:58). The EGFP gene was amplified by PCR from pIRES-EGFP using primers that introduce 5' and 3' non-translating sequences (NTS) from M segment of the WSN virus. The 5'-NTS-EGFP-NTS-3' fragment was cloned into the AarI sites inbetween CPI and MTI in plasmid pYA4379 (SEQ ID NO:57) and in pYA4380 (SEQ ID NO:58) to obtain plasmids pYA4387 and pYA4392, respectively (FIG. 1B). Plasmid pYA4688 was derived from pYA4392 bp replacing the chicken Pol I promoter with human Pol I promoter derived from pTM-Pol I-WSN-All (FIG. 1B). Genes encoding PB2, PB1 and PA were individually cloned into plasmid pcDNA3.1(−) to obtain plasmids pYA4337, pYA4338 and pYA4339, respectively. In transfection experiments, those three plasmids were used in combination with plasmid pCAWS-NP to provide viral polymerase and nucleoprotein.

Construction of the 8-unit plasmid pYA4519 (SEQ ID NO: 60)

Figure 3:
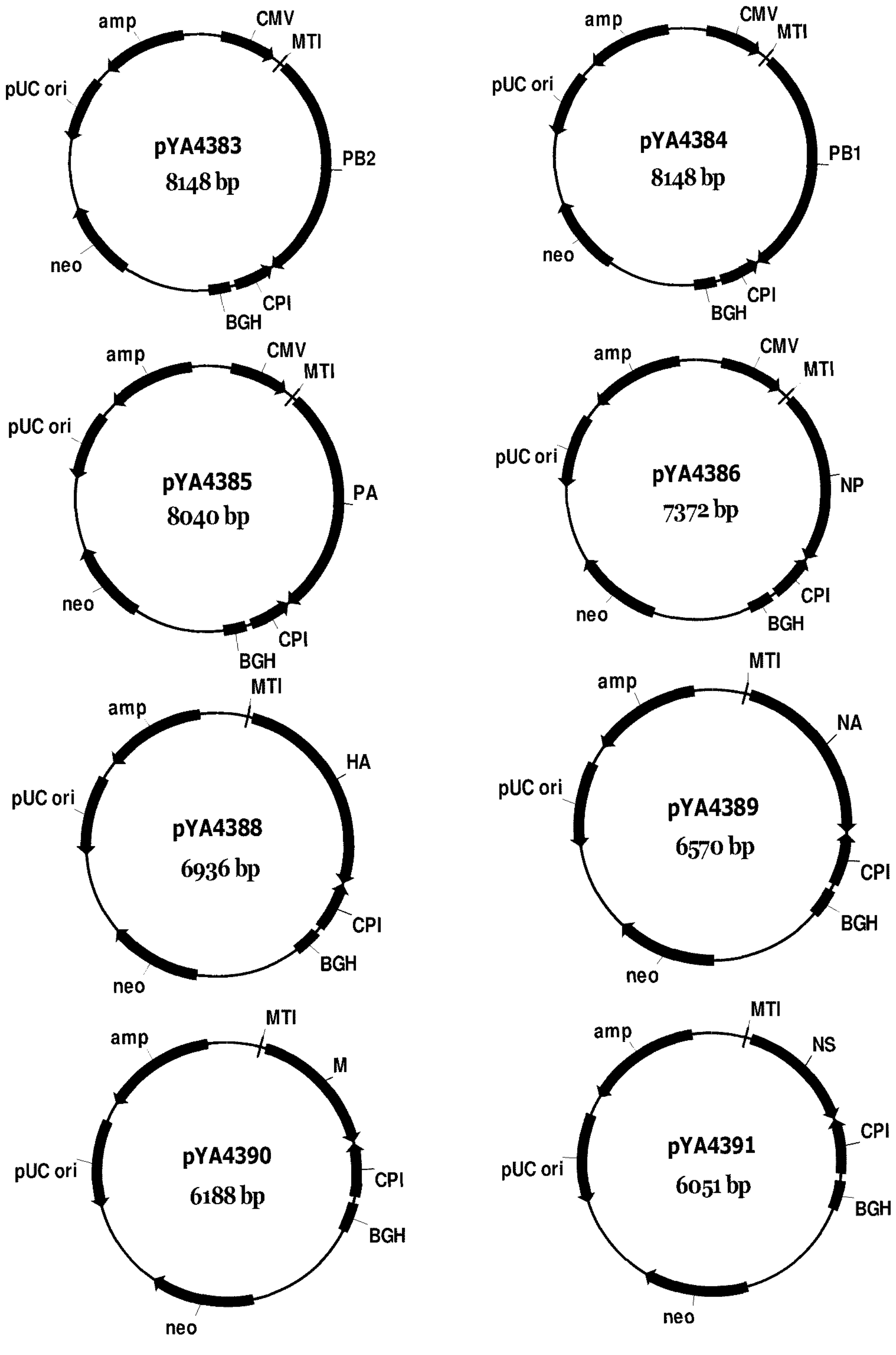
FIG. 3 depicts the "eight-plasmid" system of influenza A virus. Plasmids pYA4383, pYA4384, pYA4385, and pYA4386 were constructed by individually cloning the PB2, PB1, PA and NP genes into pYA4379 (SEQ ID NO: 57). Plasmids pYA4388, pYA4389, pYA4390 and pYA4391 were constructed by individually cloning the HA, NA, M and NS genes into plasmid pYA4380 (SEQ ID NO: 58).
Figure 4:
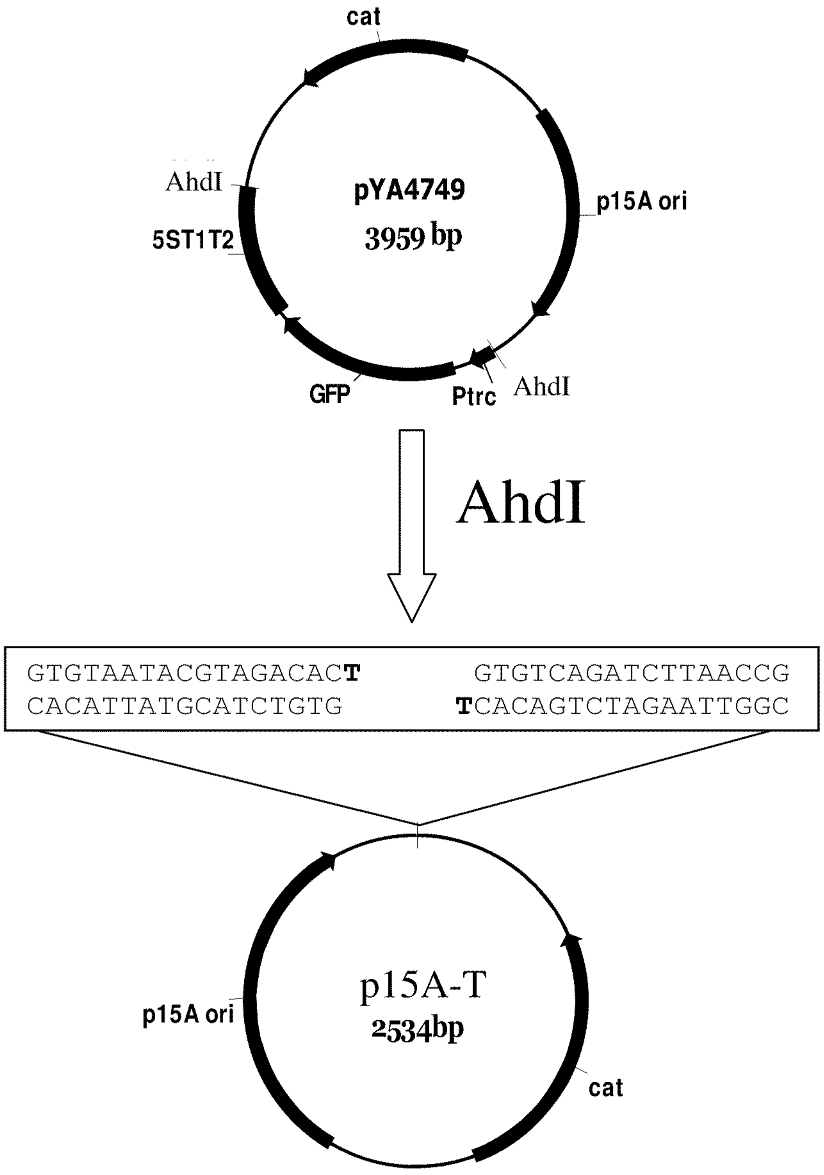
FIG. 4 depicts the generation of the p15A ori based T vector. Boxed sequence depicts the T-overhang resulting from excision of the GFP cassette with AhdI. The T-overhang was generated to facilititate convenient cloning of DNA fragments containing an A-overhang at each 3' end (see SEQ. ID NO: 59).
Figure 5:
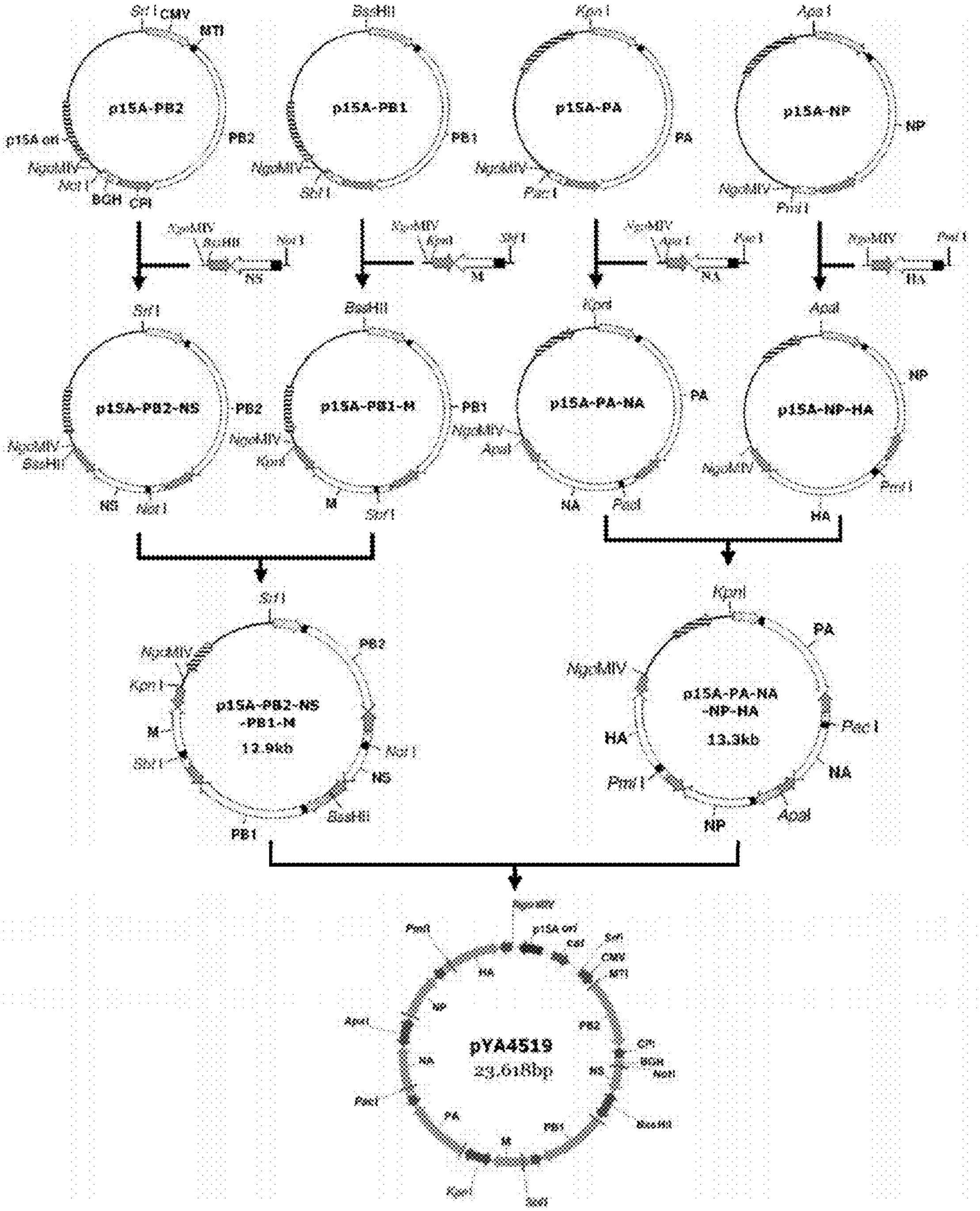
FIG. 5 depicts the step-wise construction of the 8-unit-plasmid pYA4519 (SEQ ID NO: 60). (A) PB2, PB1, PA and NP bi-directional cassettes (CPI and MTI in one direction, and cytomegalovirus (CMV) promoter and bovine growth hormone (BGH) polyA sequence in the other direction) were amplified from pYA4379 (SEQ ID NO:57)-derived plasmids (pYA4383, pYA4384, pYA4385, and pYA4386), and each cassette was individually cloned into a p15A-T vector to obtain four 1-unit plasmids p15A-PB2, p15A-PB1, p15A-PA, and p15A-NP. (B) The NS, M, NA and HA vRNA-transcribing cassettes were amplified from pYA4380 (SEQ ID NO:58)-derived plasmids (pYA4391, pYA4390, pYA4389 and pYA4388) by introducing compatible restriction sites and were each cloned into a 1-unit plasmid to obtain four 2-unit plasmids; p15A-PB2-NS, p15A-PB1-M, p15A-PA-NA, and p15A-NP-HA. (C) Each of the two 4-unit plasmids p15A-PB2-NS-PB1-M and p15A-PA-NA-NP-HA was constructed by fusing transcribing cassettes from two of 2-unit plasmids shown in B. (D) The DNA fragment containing PA-NA-NP-HA vRNA transcribing cassettes was excised using KpnI and NgoMIV and ligated into the compatible sites in the 4-unit plasmid p15A-PB2-NS-PB1-M to obtain a 23.6 kb long 8-unit-plasmid pYA4519 (SEQ ID NO:60) to transcribe the whole set of influenza vRNAs via the chicken RNA polymerase I promoter (CPI) and to synthesize influenza virus RNA polymerase (PB1, PB2, PA) and nucleoprotein (NP) by the cytomegalovirus (CMV) promoter. All constructs carry the p15A ori of replication. Plasmids are not drawn to scale. p15A-PB1, polymerase B1 cDNA cassette cloned in p15A-T vector; p15A-PB2, polymerase B2 cDNA cassette cloned in p15A-T vector, p15A-PA, polymerase A cDNA cassette cloned in p15A-T vector; p15A-NP, nucleoprotein cDNA cassette cloned in p15A-T vector; HA=hemagglutinin, NA=neuraminidase, M=matrix protein, NS=non-structural protein.

The 8-unit plasmid pYA4519 was constructed in four stages: a) Construction of eight 1-unit plasmids. Plasmid pTM-PolI-WSN-All provides the whole set of genomic cDNAs of influenza A/WSN/33 virus. The cDNA fragments for PB2, PB1, PA, and NP were individually transferred into the AarI sites on pYA4379 (SEQ ID NO:57) to obtain plasmids pYA4383, pYA4384, pYA4385, and pYA4386, respectively (Table 1, FIG. 3). Each of the HA, NA, M and NS cDNAs was similarly cloned into pYA4380 (SEQ ID NO:58) to obtain plasmids pYA4388, pYA4389, pYA4390, and pYA4391, respectively (Table 1, FIG. 3). b) Construction of cloning vector p15A-T. DNA fragments from two different plasmids were fused to construct the cloning vector p15A-T: Plasmid pYA4464 (Table 1) was the source for p15A ori and the cat gene and plasmid pYA3994 was the source of the $P_{trc}$-GFP-5ST1T2 expression cassette. An approximately 2550 bp DNA fragment containing both p15A-origin of replication and the cat gene was excised from plasmid pYA4464. A 1400 bp $P_{trc}$-GFP-5ST1T2 expression cassette was amplified from plasmid pYA3994 (Table 1) using primers that introduced sites for enzymes SnaBI and AhdI towards the 5' end and sites for AhdI and BglII towards the 3' end of the cassette. The PCR product was digested at the ends and ligated with the previously obtained 2550 bp fragment to generate a 3900 bp GFP expression vector pYA4749 (SEQ ID NO: 59, FIG. 4). The GFP expression cassette was excised out of pYA4749 bp digesting with AhdI leaving behind a linear 2530 bp vector p15A with a 3'-T overhang (generated due to AhdI digestion, FIG. 4). This linear vector will henceforth be referred to as plasmid p15A-T and will be used for convenient insertion of DNA fragments with an additional overhanging A nucleotide. c) Cloning of dual-promoter cassettes into p15A-T. cDNA cassettes of PB1, PB2, PA, and NP, along with their promoter-terminator bidirectional elements were individually amplified from pYA4384, pYA4383, pYA4385, and pYA4386, respectively, using high fidelity Pfu polymerase (PfuUltra, Stratagene) and primers that introduced unique restriction sites at both the 5' and the 3' ends of the PCR products. To generate a 3'-A overhang, the four amplicons were individually mixed with 5U of Taq DNA polymerase (New England Biolabs) and 0.5 mM dATP at 37° C. for 30 min. Purified products were each ligated with p15A-T linear vector to obtain four 1-unit plasmids p15A-PB2, p15A-PB1, p15A-PA, and p15A-NP (Table 1 and FIG. 5, upper panel). To construct 2-unit plasmids, mono-promoter cassettes of the remaining four viral genes (HA, NA, M, and NS) were amplified from plasmids pYA4388, pYA4389, pYA4390, and pYA4391, respectively, and cloned into unique restriction sites available on each of the 1-unit plasmids (FIG. 5). For instance, the CPI-NS-MTI fragment was amplified from pYA4391 using primers that engineer NotI and NgoMIV sites at the ends of the amplicon and was then cloned into the same sites on the 1-unit plasmid p15A-PB2 to obtain a two-unit plasmid p15A-PB2-NS (FIG. 5). Plasmids p15A-PB1-M, p15A-PA-NA, and p15A-NP-HA were also constructed by a similar procedure. As a step-wise incremental process, cDNA fragments from two different 2-unit plasmids were fused to obtain a 4-unit plasmid. The structures of the two 4-unit plasmids p15A-PB2-NS-PB1-M (12.9 kb) and p15A-PA-NA-NP-HA (13.3 kb) were shown (FIG. 5). d) Fusion of eight cDNA cassettes into a single plasmid. The DNA fragment containing PA-NA-NP-HA cassettes was excised from p15-PA-NA-NP-HA and cloned in between the KpnI and NgoMIV sites in the other four-unit plasmid to obtain the single 8-unit plasmid pYA4519 (FIG. 5) (SEQ ID NO:60). It is a 23.6 kb long plasmid containing unique restriction sites (SrfI, NotI, BssHII, SbfI, KpnI, PacI, ApaI, PmlI and NgoMIV) between every two cassettes and plasmid backbone to facilitate either any addition or replacement of genes in this plasmid. During the construction of the 4-unit and 8-unit plasmids, large DNA fragments were stained with crystal violet to avoid DNA damaging effects of ultraviolet light (30). These manipulations can also be performed in laboratory space equipped with yellow fluorescent lighting fixtures.

The 711 bp mCherry gene was amplified from pYS1190 (Table 1) and cloned between the CMV promoter and BGH terminator sequences on plasmid pcDNA3.1(−) to generate the reference plasmid pYA4731. The CMV-mCherry-BGH-polyA cassette was amplified from pYA4731 and cloned into the SrfI site on plasmid pYA4519 (SEQ ID NO:60) to obtain pYA4732 (pYA4519-mCherry) (Table 1).

Transfection.

CEFs and HEK293 cells grown in 6-well plates were transfected according to the manufacturer's instructions. Briefly, 2 μl of Lipofectamine 2000 (Invitrogen) per μg plasmid DNA were individually diluted in 100 μl of Opti-MEM. After 5 min incubation at room temperature (RT), the diluted transfection reagent was mixed with the DNA. After 40 min incubation at RT, the transfection mix was added to pre-washed cells. After further incubation at RT for 3 h, the transfection medium was replaced with DMEM supplemented with 10% FBS. At 24 h post transfection, images were acquired using the Zeiss Axio Cam Mrc-5 mounted onto a Zeiss Axioskop 40-fluorescent microscope.

Virus Generation.

For generation of influenza virus, CEFs or co-cultured CEFs/MDCK cells were transfected with plasmid DNA as described above. After 3 h incubation, the transfection medium was replaced with 2 ml of Opti-MEM containing 0.3% bovine serum albumin (BSA), penicillin and streptomycin. At 24 hr post transfection, each well was supplemented with 1 ml of Opti-MEM containing 2 μg/ml TPCK-trypsin, 0.3% BSA, penicillin and streptomycin. At three to six days post transfection, cell supernatants were titrated onto MDCK cell monolayers to estimate influenza virus titer. All experiments were done in triplicates.

Example 1

EGFP Expression in Vectors with Dual- or Mono-Promoter Unit

The bidirectional dual promoter transcription vector pYA4379 (SEQ ID NO:57) was constructed by inserting Pol I promoter-terminator elements in plasmid pcDNA3.1(−). Here, cytomegalovirus promoter (CMV) and bovine growth hormone (BGH) polyadenylation signal (BGH) together constitute the Pol II promoter-terminator unit to synthesize mRNA, whereas, chicken Pol I promoter (CPI) and murine Pol I terminator (MTI) together constitute the Pol I promoter-terminator unit to transcribe antisense RNA of the target gene (FIG. 1A). Alternatively, the unidirectional vector pYA4380 (SEQ ID NO:58) containing the Pol unit but lacking the CMV promoter was created for the synthesis of antisense RNA alone (FIG. 1A). Plasmids pYA4387 and pYA4392 were derived from pYA4379 (SEQ ID NO:57) and pYA4380 (SEQ ID NO:58), respectively, by inserting the reporter gene EGFP between CPI and MTI to monitor the promoter activities in both plasmids (FIG. 1B). Another unidirectional plasmid pYA4688 was derived from pYA4392 by replacing human the Pol I promoter (HPI) for CPI and used as a control for monitoring EGFP synthesis (FIG. 1B).

Figure 2:
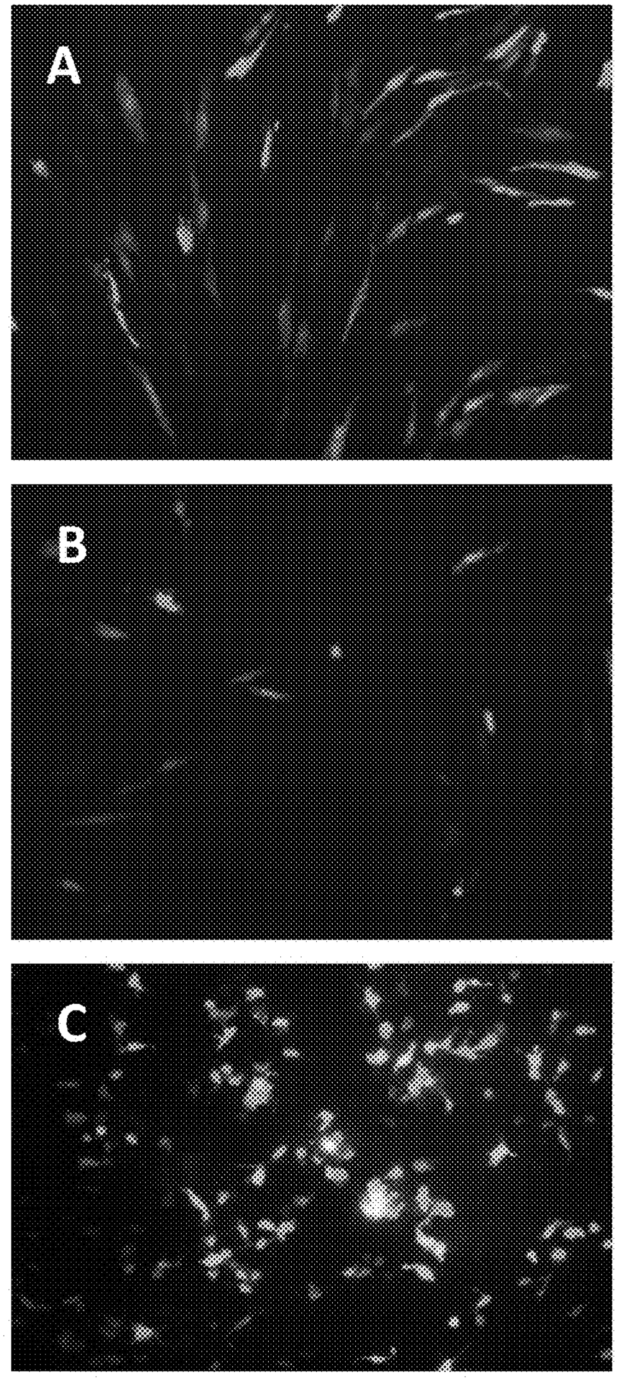
FIG. 2 depicts EGFP synthesis as a measure of protein and vRNA synthesis. Chicken embryonic fibroblasts (CEFs) transfected with pYA4387 (A); CEFs transfected with pYA4392 and four helper plasmids pYA4337 (expressing PB2), pYA4338 (expressing PB1), pYA4339 (expressing PA), and pCAWS-NP (expressing NP) (B); HEK (human embryonic kidney) 293 cells transfected with pYA4688 and four helper plasmids pYA4337 (PB2), pYA4338 (PB1), pYA4339 (PA) and pCAWS-NP (C). Images were taken 24 h post transfection at 100× magnification.

To test the promoter activity in each plasmid, CEFs were independently transfected with plasmids (pYA4387 and pYA4392) and HEK293 cells were transfected with plasmid pYA4688 to monitor EGFP expression as a measure of promoter activity. CEFs transfected with pYA4387 were visibly green confirming the synthesis of a functional EGFP protein (FIG. 2A). As expected, synthesis of EGFP was not observed in CEFs or in HEK293 cells when transfected with the either pYA4392 or pYA4688 (data not shown), as only the vRNA-like antisense RNA was synthesized by the Pol I unit in both cases. Expression was restored only upon co-transfection with pYA4337 (PB2), pYA4338 (PB1), pYA4339 (PA) and pCAWS-NP that together provide influenza RNA polymerases and the nucleoprotein required for vRNA replication and transcription to synthesize a functional EGFP (FIGS. 2B and C). These data suggested that pYA4387, pYA4392 and pYA4688 (and thus the parent plasmids pYA4379 (SEQ ID NO:57) and pYA4380 (SEQ ID NO:58)) carry functional promoter-terminator units and could transcribe the cloned cDNA into vRNA-like molecules in CEFs. However, the percentage of cells expressing EGFP was higher in HEK293 than in CEFs (FIG. 2).

Example 2

One-Plasmid System pYA4519 (SEQ ID NO:60)

We chose influenza A/WSN/33 virus as our model virus and cDNAs for all eight segments were obtained from the plasmid pTM-PolI-WSN-All. FIG. 5 outlines the sequential construction of plasmids to obtain the 8-unit plasmid pYA4519 (SEQ ID NO:60). To generate an 8-unit one-plasmid construct, we first constructed a p15A-T cloning vector from two plasmids pYA4464 and pYA3994 (see Materials and Methods). We amplified bidirectional cassettes of PB2, PB1, PA, and NP from plasmids pYA4383, pYA4384, pYA4385, and pYA4386, respectively (see Materials and Methods, and Table 1), and cloned individually into the p15A-T vector to obtain four 1-unit plasmids expressing viral mRNA (FIG. 5). The vRNA expression cassettes (CPI-cDNA-MTI) for HA, NA, M, and NS were then cloned into the 1-unit plasmids to obtain four 2-unit plasmids (FIG. 5). Two 2-unit plasmids were fused to obtain a 4-unit plasmid and two of those were ligated together to obtain a 23.6 kb-long 8-unit plasmid pYA4519 (SEQ ID NO:60) (FIG. 5). Plasmid pYA4519 (SEQ ID NO:60) contains a p15A origin of replication adjacent to a chloramphenicol resistance gene (cat). It is designed to synthesize both vRNA and mRNA from cDNA of each of PB1, PB2, PA and NP and vRNA from cDNA of each of HA, NA, M, and NS segments. The origin of replication, the resistance marker or any of the antigenic elements from this plasmid can be conveniently replaced with any other phenotypic determinants to generate reassortant influenza virus in cultured cells. Unique restriction sites also facilitate addition of a reporter gene cassette to monitor transfection efficiency of the plasmid. Plasmid pYA4519 (SEQ ID NO:60) was stably maintained at 37° C. in *E. coli* strains containing a recA mutation.

Example 3

Transfection Efficiency of pYA4519 (SEQ ID NO:60)

Figure 6:
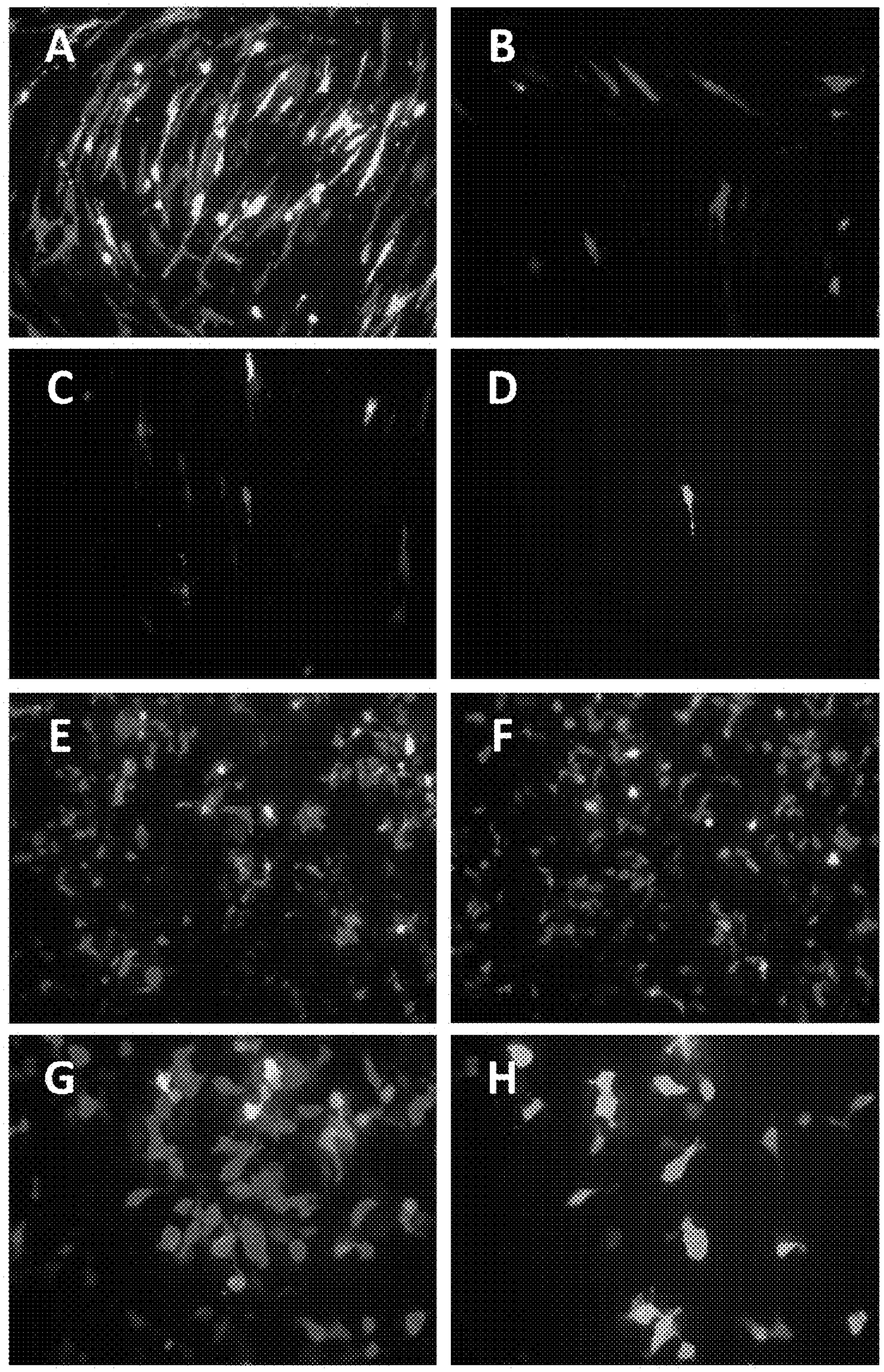
FIG. 6 depicts the transfection efficiency of the 8-unit-plasmid. CEFs (A and B) and HEK293 cells (E to F) cells transfected with plasmid pYA4731 (pcDNA-mCherry; A and E) or plasmid pYA4732 (pYA4519-mCherry; B and F). CEFs co-transfected with pYA4732 and pYA4392. Expression of mCherry gene (C) and EGFP gene (D) in CEFs was recorded from the same field. HEK293 cells co-transfected with 2 μg of pYA4732 and pYA4688 (G and H). Expression of EGFP gene (G) and mCherry gene (H) was recorded from the same field. Images were taken 24 h post transfection. Magnification, A to F, 100×; G and H, 200×.

To determine the transfection and nuclear targeting efficiency of pYA4519 (SEQ ID NO:60), we introduced the mCherry gene into the vector pcDNA3.1(−) downstream of the CMV promoter to generate pYA4731 (pcDNA-mCherry). The entire CMV-mCherry-BGH-polyA cassette was then transferred into the 8-unit plasmid pYA4519 (SEQ ID NO:60) to generate pYA4732 (pYA4519-mCherry) and then to compare the expression of the reporter gene in CEFs and HEK293 cells. Expression of the mCherry gene from the reference plasmid pYA4731 was similar in both CEFs and HEK293 cells (FIGS. 6A and E), suggesting similar levels of transfection and nuclear translocation efficiency of the small plasmid in both cell lines. However, CEFs and HEK293 cells differed in both aspects when synthesis of mCherry from the large plasmid pYA4732 was compared (FIGS. 6B and F). The level of mCherry synthesis from pYA4732 was much higher in HEK293 (FIG. 6E) than in CEFs (FIG. 6B). Expression of mCherry from pYA4732 was comparable to that from the reference plasmid pYA4731 in case of HEK293 cells (FIGS. 6E and F), whereas, in CEFs the efficiency decreased dramatically with the increase in plasmid size (compare FIGS. 6A and B). We hypothesized that the lower mCherry synthesis in CEFs (from pYA4732) may be due to limited translocation of the large plasmid into the CEFs nucleus. To test this hypothesis, we co-transfected CEFs with pYA4732 and pYA4392 (pYA4380-EGFP) and co-transfected HEK293 with pYA4732 and pYA4688 to measure the synthesis of both mCherry (FIGS. 6C and G) and EGFP (4D and F) proteins from the same field. Since the EGFP gene is cloned between the CPI-MTI Pol I unit on pYA4392 and the HPI-MTI Pol I unit on pYA4688 (resulting only in the generation of vRNA-like molecules), synthesis of a functional EGFP protein in either case is only possible in the presence of all the viral polymerases and the nucleoprotein provided from plasmid pYA4732. We observed EGFP synthesis both in HEK293 and CEFs, but the percentage of HEK293 cells synthesizing both mCherry and EGFP was much greater than in the CEFs (compare FIGS. 6C and D with FIGS. 6G and F) suggesting a lower translocation of the 8-unit plasmid into the CEFs nucleus.

Example 4

Generation of Influenza Virus from Plasmid(s)

Efficiency of influenza virus recovery was compared between our 1-unit eight-plasmid system (plasmids pYA4383, pYA4384, pYA4385, pYA4386, pYA4388, pYA4389, pYA4390, and pYA4391) and our novel one-plasmid 8-unit system pYA4519 (SEQ ID NO:60). Cultured CEFs were either transfected with pYA4519 (SEQ ID NO:60) or co-transfected with eight plasmids (pYA4383, pYA4384, pYA4385, pYA4386, pYA4388, pYA4389, pYA4390, and pYA4391) to provide all the necessary viral components as described in Materials and Methods. The mean titer at 3-days and 6-days post transfection was approximately 300 and $1\times10^3$ PFU/ml influenza viruses, respectively, when transfected with pYA4519 (SEQ ID NO:60), whereas the virus yield using the eight-plasmid method estimated at the same time points was approximately 50 and 700 PFU/ml, respectively, (Table 4). Virus yield was much higher in cocultured CEFs/MDCK cells transfected by plasmid pYA4519 (SEQ ID NO:60) with approximately $1\times10^4$ PFU/ml and $1\times10^8$ PFU/ml estimated on the 3 and 6 days post transfection, respectively. This was expected as MDCK cells are known to support the growth of influenza virus better than CEF cells. Together these results suggested that recovery of influenza virus from pYA4519 (SEQ ID NO:60) transfected cells was more efficient than from the previously developed eight-plasmid system.

TABLE 4

| Influenza A virus generation in CEFs (PFU/ml) | | | | | | |
|---|---|---|---|---|---|---|
| | $3^{rd}$ day post transfection | | | $6^{th}$ day post transfection | | |
| Plasmid(s) | No. 1[a] | No. 2[a] | No. 3[a] | No. 1[a] | No. 2[a] | No. 3[a] |
| 8 × 1-unit plasmids[b] | 40 | 60 | 60 | 1280 | 440 | 480 |
| PYA4519 | 400 | 260 | 280 | 1800 | 1000 | 1000 |

[a]Triplicate wells.
[b]Plasmids pYA4383, pYA4384, pYA4385, pYA4386, pYA4388, pYA4389, pYA4390, and PYA4391.

Discussion for Examples 1-4

The goal of this study was to construct the influenza virus genome on a single plasmid and rescue the virus from cultured chicken cells. We chose the influenza virus WSN strain as the model virus and with the combination of reverse genetics and the dual promoter system successfully constructed an 8-unit plasmid pYA4519 (SEQ ID NO:60). Care was also taken to limit the use of multiple CMV promoters in our plasmid to reduce the number of repetitive sequences that may promote intra-plasmid recombination and thus decrease plasmid stability. The 8-unit plasmid was designed to produce influenza polymerase complex (PB1, PB2 and PA), nucleoprotein (NP) and 8 viral RNAs (PB1, PB2, PA, NP, HA, NA, M and NS) in avian cells (FIG. 5). By transfection, the "one-plasmid" system showed more efficient virus generation in CEFs than our 1-unit (a unit stands for a cDNA corresponding to one influenza segment, it may be flanked only by Pol I and MTI, or flanked by both Pol I/Pol II plus their terminators) eight-plasmid system (Table 4). Generation of influenza virus from a minimal number of plasmid constructs has been a long-term challenge and through this study for the first time we demonstrated successful recovery of influenza virus from expression of a single plasmid.

Factors such as plasmid constructs used, and the host cell line, affect the efficiency of virus recovery (22), and our study provides additional vital evidence in their support. We compared both transfection and viral recovery efficiency between CEFs and HEK293 cells. Both cell types could be transfected with equal efficiency when smaller size plasmids were used (FIG. 2 and FIGS. 6A and E). The viral yield however was higher in HEK293 cells when compared to CEFs. This difference could be attributed to either lower production of vRNAs, or lower conversion from vRNAs to protein or both, in chicken cells. Transfection experiments involving the large size plasmid pYA4519-mCherry (25.3 kb), however, indicated that HEK293 cells are better recipients than the CEFs. Two important conclusions can be drawn from these observations; firstly, our data suggested that plasmid size plays an important role in successful viral recovery. Whereas efficient virus recovery and reporter gene expression in CEFs was possible by transfecting with multiple smaller plasmids (FIG. 2 and Table 4), a similar attempt using a larger plasmid (25.3 kb) had limited success, suggesting the plasmid size as a potential limiting factor. Alternatively, expression might improve in other avian species or in different cells in those species. Secondly, it is known that virus recovery is higher in 293T cells than in Vero cells or CEFs (18, 22, 23, 27). This was one important criterion for higher virus yield from the three-plasmid system developed by Neumann et. al. Our results indicated that HEK293 cells are not only highly transfectable cells, but also can be transfected with large size plasmids. Furthermore, certain cell-specific factors in HEK293 cells seem to promote nuclear translocation of larger plasmids more effectively than other cell types such as CEFs. We are hence working towards improving translocation of pYA4519 (SEQ ID NO:60) into the nucleus of CEFs by including a nuclear targeting sequence, such as the promoter/enhancer region of simian virus 40 (SV40) (6).

Our plasmid construct should also facilitate the design of a much simpler approach to develop influenza vaccine seeds. Currently, influenza vaccine seeds use the "2+6" strategy, in which the HA and NA segments are taken from an epidemic strain and the remaining 6 segments of the influenza viral genome are taken from either the high productive strain PR8 (A/PR/8/34) or the cold-adapted strain (e.g. A/AA/6/60) (4, 10, 12). Construction of one plasmid producing all the necessary backbone segments and proteins from donor virus provides a simpler and more efficient "1+2" approach to generate influenza vaccine seeds.

The currently used influenza vaccines for human use are the inactivated and attenuated forms of the virus and are administered via the intramuscular or the intranasal routes. Manufacturing these vaccines using cell culture or embryonated chicken eggs is both expensive and a time-consuming process. An inexpensive and oral influenza vaccine remains a medical priority, especially for pandemic influenza. Our one plasmid offers a viable option to generate attenuated influenza virus in vivo where the plasmid can be delivered orally or intranasally using a recombinant bacterial strain. Our laboratory has been successful in constructing recombinant attenuated strains of *Salmonella enterica* Serovar *Typhimurium* that are designed for enhanced antigen delivery in the host and ensure regulated delayed lysis of the pathogen to inhibit long-term host colonization (5). To construct such an attenuated strain that could effectively deliver plasmid DNA into the host will be the next step towards developing a recombinant bacteria based-vaccine against influenza to be used both in the poultry industry and for pandemic influenza.

In our pilot study, we choose the influenza virus WSN strain for validation of our one-plasmid system. For developing a bacterial based influenza vaccine, the expression vector must be modified to generate attenuated influenza virus. One strategy would be constructing the single expression vector with HA and NA from epidemic influenza virus and the other 6 segments from a cold-adapted influenza strain (e.g. A/AA/6/60) (4, 12). Another strategy is to introduce mutations into viral polymerase coding genes and another to employ a truncated NS1 (nonstructural protein 1) gene to obtain attenuated influenza virus (7, 29, 33). Additionally, the HA segment from influenza vaccine may form a new ressortant virus with the other segments from a preexisting influenza virus in the host. The polybasic cleavage peptides of the HA proteins are required for high pathogenicity of influenza viruses (36). Thus, for vaccine development, the polybasic cleavage site in HA will be replaced with a consensus sequence derived from HA-encoding sequences from avirulent strains (28, 33).

Example 5

Construction of the 8-Unit Plasmid pYA4562

Figure 7:
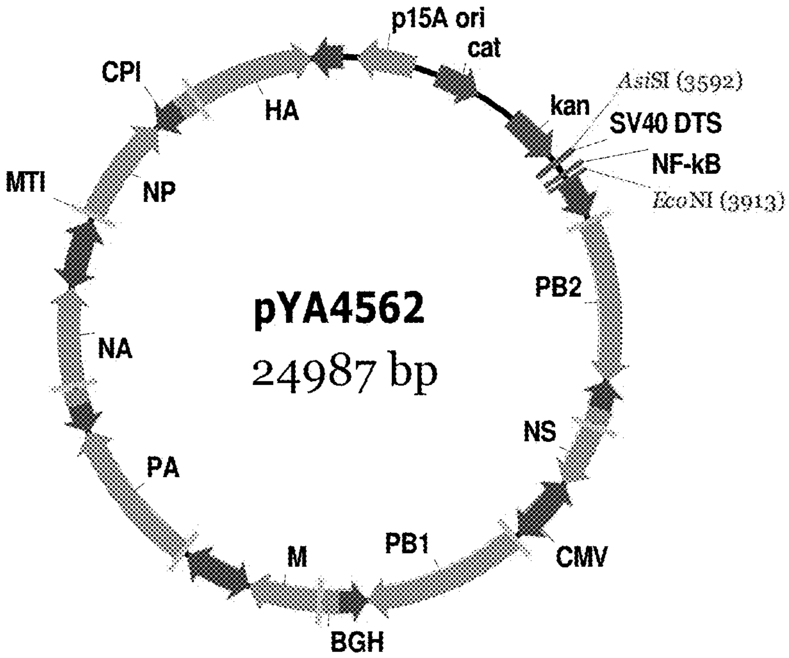
FIG. 7 depicts the 8-unit plasmid pYA4562, which is a derivative of pYA4519 with the addition of DNA nuclear targeting sequence (DTS) from simian virus 40 (SV40), and NF-κB binding sequence.

Optimal gene expression from the 8-unit plasmid requires efficient translocation of the plasmid construct into the nucleus of the host cells. Nuclear targeting sequence and NF-κB binding site have been reported to improve the nuclear import of DNA construct (6, 19). In our study, transfection of chicken cells with plasmid pYA4732 did not result in efficient expression of mCherry (Example 3). One possible reason is the lack of a nuclear targeting sequence to facilitate the nuclear import of pYA4732 (and its parental plasmid pYA4519). Here the SV40 nuclear targeting sequence (SV40 DTS) and NF-κB binding site were introduced into plasmid pYA4519 to enhance its nuclear import. The SV40 DTS was obtained from a commercial vector pBICEP-CMV-3 (Sigma) and the NF-κB binding site was obtained from plasmid pYA4545 (from Clonebank in Curtiss' lab). Then they were fused with a kanamycin-resistance cassette (kan) by PCR. The entire fusion fragment was inserted into the SrfI site of pYA4519 to generate pYA4562 (FIG. 7). This modification has led to higher virus yield in bacterial carrier-mediated plasmid delivery (example 9).

Example 6

*Salmonella* Mediated Delivery of EGFP Reporter Plasmid pYA4336

Figure 8A:
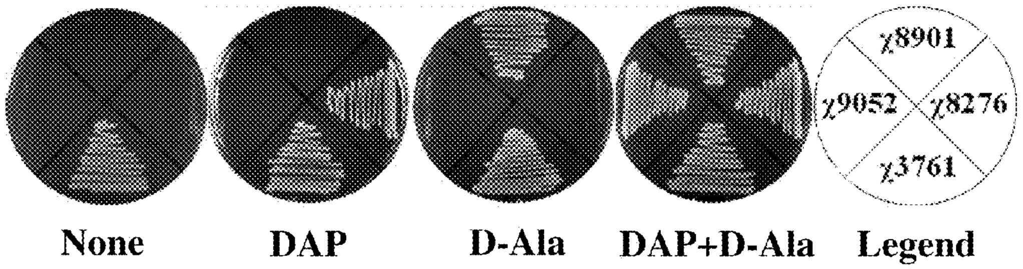
FIG. 8 depicts *Salmonella* mediated delivery of EGFP reporter plasmid pYA4336. A. *Salmonella* carriers showed conditional growth on LB-agar plates supplementing with 50 μg/ml DAP and/or 100 μg/ml DL-alanine. B. The pelleted *Salmonella* carriers were resuspended in LB broth and incubated at 37° C. overnight (standstill). Then, the bacterial cells were collected by centrifugation and stained with propidium iodide (PI) and SYTO9. The dead cells are stained in red fluorescence. The live cells are in green fluorescence. C. Reporter plasmid pYA4336 which only express EGFP in animal cells. D. Plasmid pYA4336 was delivered into CEFs by different *Salmonella* carriers. As a control, CEFs were also incubated with a mixture of bacterial carrier χ9052 and 15 μg of pYA4336. Cell nuclei were stained with 4'-6-Diamidino-2-phenylindole (DAPI).
Figure 8B:
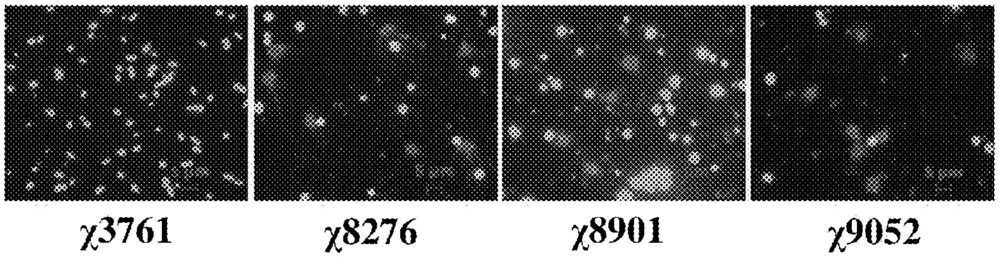
Figure 8C:
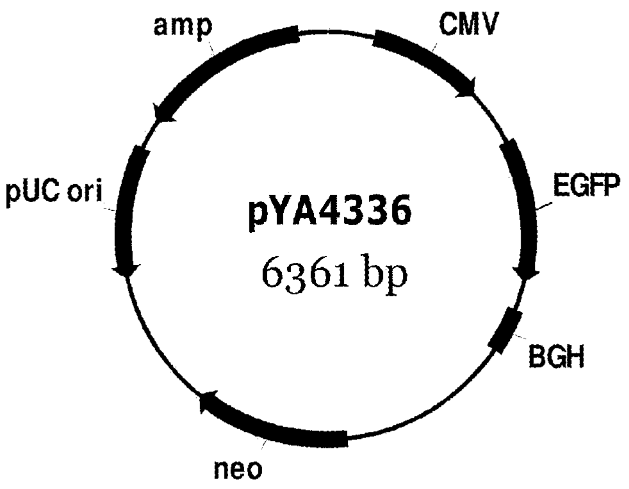
Figure 8D:
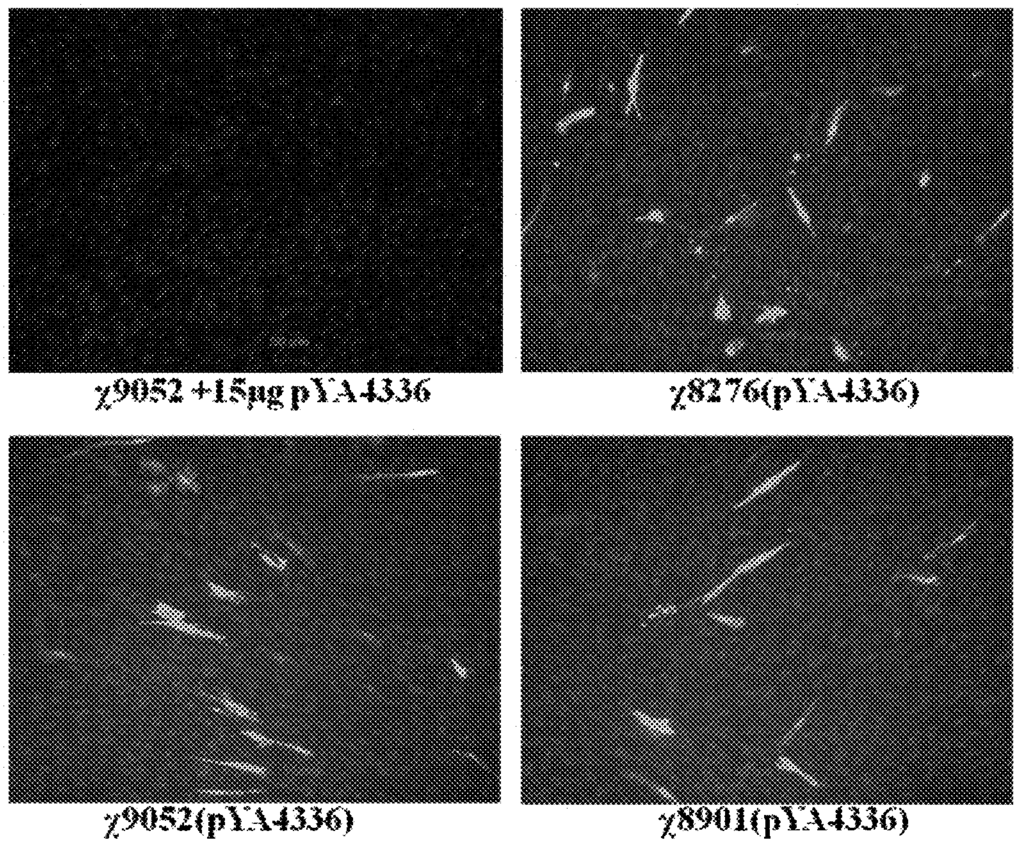

To mediate the delivery of plasmid DNA, an auxotrophic *Salmonella Typhimurium* strain χ9052 (ΔasdA33 Δalr-3 ΔdadB4) was selected. Inactivation of the asd gene causes an obligate requirement for the essential amino acid diaminopimelic acid (DAP), whereas inactivation of both the alr and dadB genes confers an absolute requirement for D-alanine. Both DAP and D-alanine are essential unique subunits of the peptidoglycan ridgid layer of the bacterial cell wall. A replicating bacterial cell requires these components for cell wall synthesis and neither of these amino acids is present in animal tissues. In the absence of these nutrients in the host cell, the integrity of the bacterial cell wall is compromised and the bacterium undergoes lysis in the host. Lysis of the intracellular bacterial cell would release the expression vector into the host cytoplasm, and the nuclear targeting sequence(s) on the vector would then promote the translocation of the expression vector into the nucleus, ultimately resulting in the desired expression of viral genes. The conditional growth on LB agar plates with or without supplement(s) was observed for three bacterial carriers, including χ8276 (ΔasdA27), χ8901 (Δalr-3 ΔdadB4) and χ9052 (ΔasdA33 Δalr-3 ΔdadB4). The wild-type *S. Typhimurium* control strain showed growth on each plate (FIG. 8A). In another assay, each *Salmonella* carrier was resuspended and incubated in LB broth without any supplements for 24 hours. Then the bacterial cells were gently pelleted (8,000 rpm for 5 min) and stained with Live/Dead BacLight Bacterial Viability kit (Molecular probes, cat. L13152). Under the fluorescence microscope the carrier strains χ8276, χ8901 and χ9052 showed much bigger size and more dead cells (red fluorescence) than the wild-type strain χ3761 (FIG. 8B). Surprisingly, the genomic DNA stained with PI (red fluorescence) was even found to flush out from the dead bacterial cells. Comparing with wild-type control, the three carrier strains showed much more cell debris that can not be stained with fluoresceins due to the loss of genomic DNA. Those data proved that the incomplete bacterial cell wall was unable to protect the bacterial cell membrane from damage of stress, permeation pressure and other factors. Plasmid pYA4336 is a derivative of pcDNA3.1(−) obtained by cloning the EGFP gene under the control of the CMV promoter (FIG. 8C). *Salmonella Typhimurium* χ8276, χ8901 and χ9052 carrying pYA4336 each was cultured in 3 ml of LB medium containing 100 μg/ml DL-alanine, 50 μg/ml diaminopimelic acid (DAP) and 100 μg/ml ampicillin at 30° C. The bacterial pellet was resuspended in DMEM without fetal bovine serum (FBS) and antibiotics. Chicken embryonic fibroblasts (CEFs) cultured in a 6-well plate were incubated with the bacteria at 37° C. for 1 h. 24 hours later, the cells were observed in the fluorescence microscope for EGFP expression (FIG. 8D). Though EGFP expressing cells could be observed from CEFs infected by either of the bacterial carriers, the χ9052(pYA4336) seemed to result in the most efficient plasmid delivery in repeated experiments (data not shown).

Example 7

Determination of the Structural Integrity of the 8-Unit Plasmid in Strains of *Salmonella Typhimurium*

For bacterial carrier-mediated plasmid delivery, it is essential that the structural integrity of the target plasmid construct be maintained. RecA and RecF (encoded by genes recA and recF, respectively) catalyze recombination of homologus DNA sequences on one plasmid or between two plasmids. The 8-unit plasmid construct carries numerous such repeated DNA elements in the form of Pol I and Pol II promoters and terminators. These repeated sequences are very good substrates for both RecA- and RecF-enzyme mediated recombination. We hence determined the individual effect of the inactivation of these genes in *Salmonella.*

The recA and recF deletion mutations were individually introduced into *Salmonella Typhimurium* χ9052 (ΔasdA33 Δalr-3 ΔdadB4). The resulting strains are χ9834 (ΔasdA33 Δalr-3 ΔdadB4 ΔrecA62) and χ11018 (Δasd-33 Δalr-3 ΔdadB4 ΔrecF126), respectively.

Figure 9:
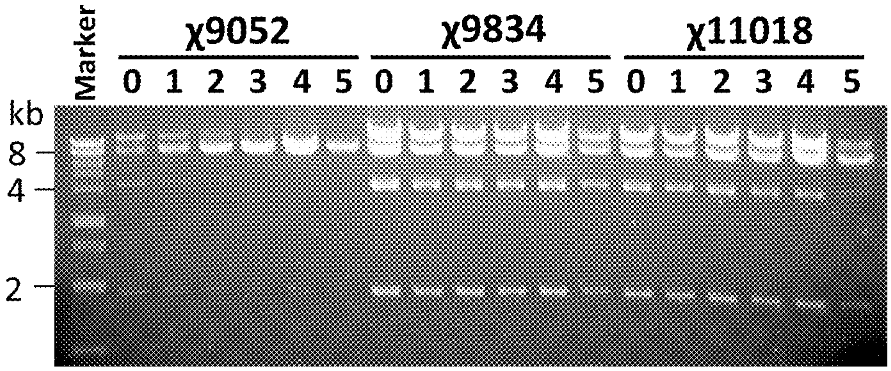
FIG. 9 depicts a restriction digestion analysis of plasmid pYA4519 after continuous passages in *Salmonella* strains χ9052, χ9834, and χ11018. The passage number is noted above each lane. The first lane (M) contains a DNA marker for size reference (10 kb, 8 kb, 6 kb, 5 kb, 4 kb, 3 kb, 2.5 kb, 2 kb and 1.5 kb).

*Salmonella* strains χ9052, χ9834 and χ11018 were each transformed with plasmid pYA4519, plated onto LB plates and incubated overnight at 37° C. From each strain, a correct clone was obtained and diluted 1:1000 into 3 ml LB medium and grown at 37° C. for 12 h. The dilution and growth process was repeated for 4 additional cycles. Plasmid DNA was extracted from 1.5 ml of culture from each cycle of growth. An aliquot of plasmid from each sample was digested with BamHI and separated on a 1.2% agarose gel. Bacteria from the final cultures were spread onto supplemented LB-agar plates and incubated overnight at 37° C. Plasmid DNA was extracted from single colonies and structural integrity of the plasmid was verified by comparing the restriction profile upon BamHI digestion (FIG. 9). Accumulated recombination events lead to gene deletions on plasmid pYA4519, therefore resulting in changes of the restriction map generated by BamHI digestion.

We noted that at time 0, before passage, the plasmid yield from the $Rec^+$ strain, χ9052, was less than that obtained from the two rec mutants. After the second cycle of growth there was a reduction in the amount of DNA in most of the expected bands, indicating that the plasmid structure was deteriorating after each passage. Qualitatively, the plasmid structure appeared to be stable for the first four passages in strains χ9834 (ΔrecA62), and χ11018 (ΔrecF126). In this experiment we demonstrate that deletion of recA and recF in *Salmonella Typhimurium* significantly minimizes Rec-dependent recombination of the plasmid, thus ensuring structural integrity of our 8-unit plasmid in spite of repetitive sequences.

Example 8

χ9834-Mediated Delivery of Plasmid pYA4732

Figure 10A:
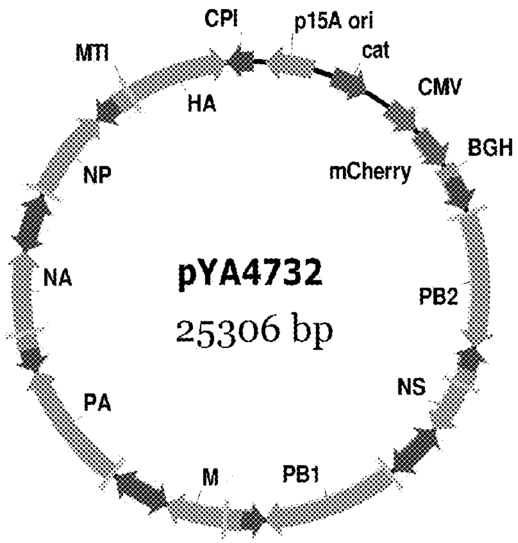
FIG. 10 depicts the 8-unit plasmid pYA4732 (pYA4519-mCherry) and CEFs infected by χ9834 carrying pYA4732. As a control, CEFs were also infected by χ9834 carrying pYA4731. Cell nuclei were stained with 4'-6-Diamidino-2-phenylindole (DAPI).

The goal of this experiment was to determine whether *Salmonella* could mediate the delivery of the large expression vector into cultured chicken cells. Plasmid pYA4732 (FIG. 10A) was derived from the 8-unit plasmid pYA4519 by inserting a eukaryotic mCherry expression cassette that is from plasmid pYA4731. The mCherry gene is used as a reporter gene in this experiment; wherein, expression of the gene product signifies successful lysis of the bacterium in the host cytoplasm and eventual translocation of the plasmid construct to the host cell nucleus. *Salmonella Typhimurium* strain χ9834 (ΔasdA33 Δalr-3 ΔdadB4 ΔrecA62) was selected to deliver pYA4732. This strain has obligate requirements for diaminopimelic acid (DAP) and D-alanine by virtue of the ΔasdA33 Δalr-3 ΔdadB4 mutations. The strain will thus undergo lysis in the host cells in the absence of the above mentioned nutrients. Bacterial cell lysis ensures release of the plasmid DNA into the *Salmonella* containing vacuole (SCV) and it can then be transported into the nucleus through a yet unknown mechanism, resulting in expressing the genes under question. This strain also carries a recA62 deletion to reduce plasmid recombination in pYA4732.

Figure 10B:
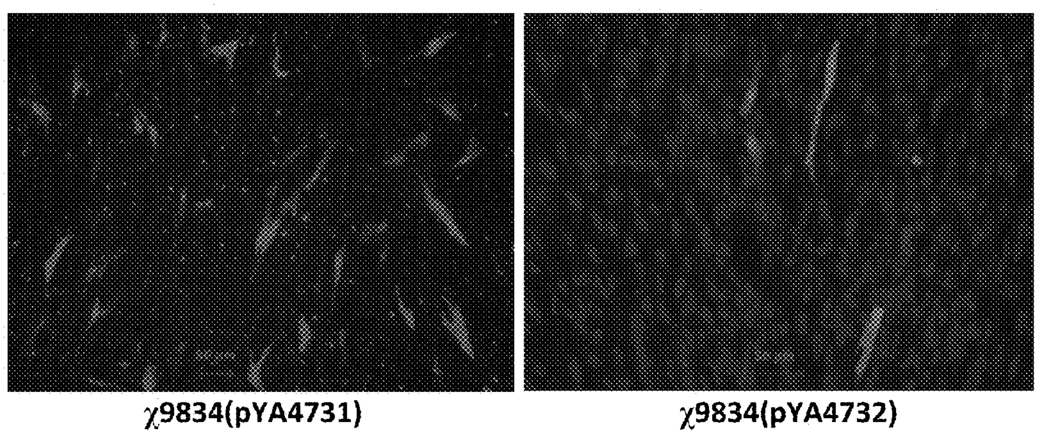

*Salmonella Typhimurium* χ9834 carrying pYA4732 was cultured in 3 ml of LB medium containing 100 μg/ml DL-alanine, 50 μg/ml DAP and 25 μg/ml chloramphenicol at 30° C. As a control, the χ9834 carrying pYA4731 was cultured in 3 ml of LB medium containing 100 μg/ml DL-alanine, 50 μg/ml DAP and 100 μg/ml carbencillin at 30° C. The overnight cultures were pelleted and resuspended in DMEM without fetal bovine serum and antibiotics. Chicken embryonic fibroblasts (CEFs) in 6-well plates were incubated with the bacteria at 37° C. for 1 h. 24 h later, the cells were observed under fluorescence microscope. The results showed that the large plasmid pYA4732 could be delivered into cultured chicken fibroblasts and was expressed. In contrast, the small reporter plasmid pYA4731 was more efficiently delivered by the *Salmonella* carrier (FIG. 10B). These results suggest that the large size plasmid suffers from inefficient nuclear import in bacterial-mediated plasmid delivery as well as in transfection. Of note, the plasmid pYA4731 also expresses mCherry in prokaryotic cells, as observed in *E. coli* and *Salmonella* strains. It is most likely results from the inframe ATG codon close to the 5' terminus and the adjacent upstream SD sequence. Therefore, live bacterial cells are observed as red spots for cells infected by χ9834(pYA4731).

Example 9

Influenza Virus Rescued from Co-Cultured CEFs/MDCK Cells by Infection with χ9834 carrying pYA4519 or pYA4562

The goal of this experiment was to determine whether *Salmonella*-mediated delivery of the 8-unit plasmid into chicken cells leads to the generation of influenza virus. Based on the transfection data (Table 4), the chicken embryonic fibroblasts did not support the replication of the influenza virus WSN strain (no substantial increase of virus titers between the 3rd and 6th day post transfection). The MDCK cells on the other hand are known to support the growth of the influenza virus WSN strain. A co-culture of chicken embryonic fibroblasts (CEFs) and Madin-Darby canine kidney (MDCK) cells supports the propagation of the influenza virus. Virus generated and released from transfected CEFs can infect the adjacent MDCK cells that support replication of the virus. Transfection of co-cultured CEFs/MDCK cells with the 8-unit plasmid pYA4519 resulted in higher titers of influenza virus (Example 4). *Salmonella Typhimurium* χ9834 carrying pYA4519 or pYA4562 were cultured in 3 ml of LB medium containing 100 μg/ml DL-alanine, 50 μg/ml DAP and 25 μg/ml chloramphenicol at 30° C. with shaking (200 rpm) for 20 h. In each case, 1 ml of bacterial culture was harvested and resuspended in 1 ml of DMEM without fetal bovine serum (FBS) and antibiotics.

Figure 11:
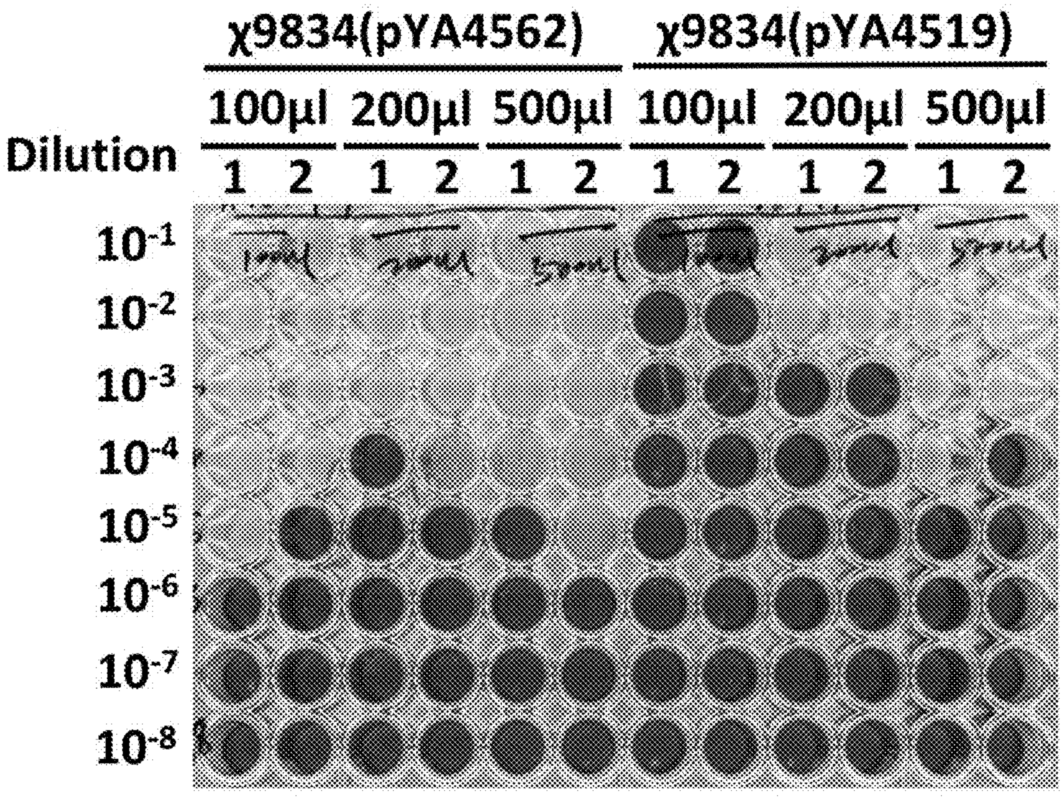
FIG. 11 depicts a 96-well plate for measuring $TCID_{50}$ of influenza virus rescued from cocultured CEFs/MDCK (Madin-Darby canine kidney) cells by infection with *Salmonella Typhimurium* carrying pYA4519 or pYA4562.

CEFs and MDCK cells grown in 75 $cm^2$ flasks were trypsinized, and ⅓ volume of each was mixed with DMEM containing 10% FBS to a total volume of 40 ml. The mixed cells were seeded into six-well plates at 3 ml per well. All cells were maintained at 37° C. in 5% $CO_2$. The cells were washed with DPBS for three times. 100 μl, 200 μl and 500 μl of resuspended bacteria were added into each well. DMEM was added to a final volume of 1 ml and mixed by rocking back and forth. The cells were incubated at 37° C. in a $CO_2$ incubator for 1 h. For each well, media was changed to 2 ml of Opti-MEM containing 0.3% BSA, 10 μg/ml gentamycin. One day post-infection, each well was supplemented with 1 ml of Opti-MEM containing 0.3% BSA, 10 μg/ml gentamycin and 2 μg/ml TPCK-trypsin (The final concentration is 0.7 μg/ml). Six days post-infection, supernatants from each well were collected for hemagglutination tests (Table 5) and $TCID_{50}$ determinations (FIG. 11). The latter result indicates generation of active influenza virus.

CEFs/MDCK co-culture infected with χ9834 carrying pYA4562 generated higher titers of influenza virus, supporting our hypothesis that inclusion of additional nuclear targeting sequences in the 8-unit plasmid enhances the nuclear translocation, hence the viral yield.

TABLE 5

Hemagglutination test on the supernatants from co-cultured CEFs/MDCK cells infected by *Salmonella* delivering 8-unit expression plasmids

| | χ9834(pYA4562) | | | χ9834(pYA4519) | | | |
|---|---|---|---|---|---|---|---|
| Dilution | 100 μl | 200 μl | 500 μl | 100 μl | 200 μl | 500 μl | WSN virus (Positive control) |
| 1:2 | + | + | + | − | − | + | + |
| 1:4 | + | + | + | − | − | − | + |
| 1:8 | + | − | + | − | − | − | + |
| 1:16 | − | − | − | − | − | − | + |
| 1:32 | − | − | − | − | − | − | − |
| 1:64 | − | − | − | − | − | − | − |

+, Hemagglutination of chicken red blood cells.
−, No hemagglutination observed.

Example 10

Construction of 8-Unit Plasmids Carrying HA and NA Genes from LPAI Virus

To generate of attenuated influenza virus in vivo and to determine the immune response against the attenuated strain, it is necessary to construct a plasmid encoding an attenuated virus. So that the virus generated in vivo can be determined by virus shielding, and the immune response can be determined by subsequent challenge with influenza virus.

The influenza A virus (A/chicken/TX/167280-4/02 (H5N3) is an isolate from White Leghorns chickens. It belongs to a low pathogenic avian influenza virus and causes clinical symptoms such as wheezing and swollen heads. The viral HA segment (AY296085, henceforth referred to as Tx02HA), shares homology with low pathogenic virus (16). It hence makes an ideal challenge strain. On the other hand, an avirulent influenza A virus can be generated from a single expression vector encoding Tx02HA and Tx02NA (NA segments derived from Tx02 virus) segments and the remaining 6 segments from a mouse adapted influenza virus, such as the WSN virus.

Figure 12A:
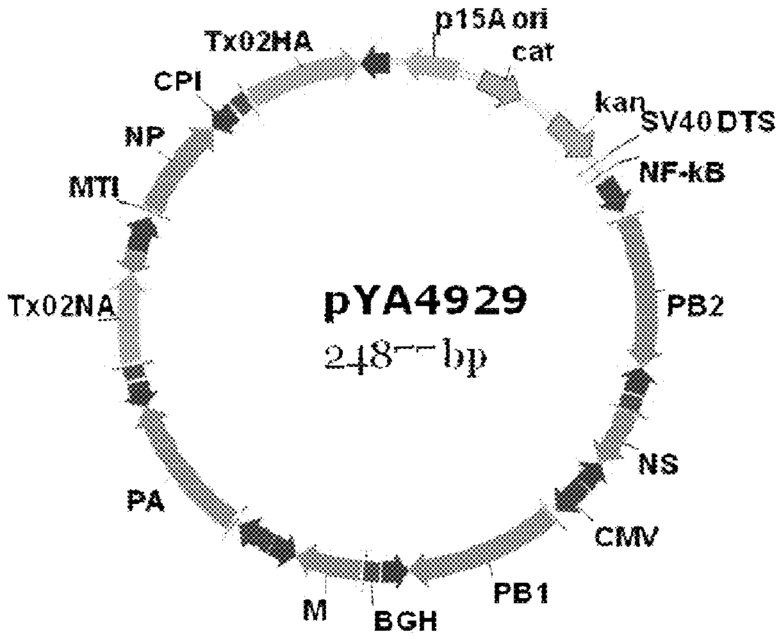
FIG. 12 depicts the 8-unit plasmids carrying HA and NA genes from influenza A virus (A/chicken/TX/167280-4/02 (H5N3). The chloramphenicol resistance marker (cat) and kanamycin resistance marker (kan) in plasmid pYA4929 (A) were replaced with aroA cassette derived from pYA4784. The resulting plasmid is designated as pYA4930 (B).
Figure 12B:
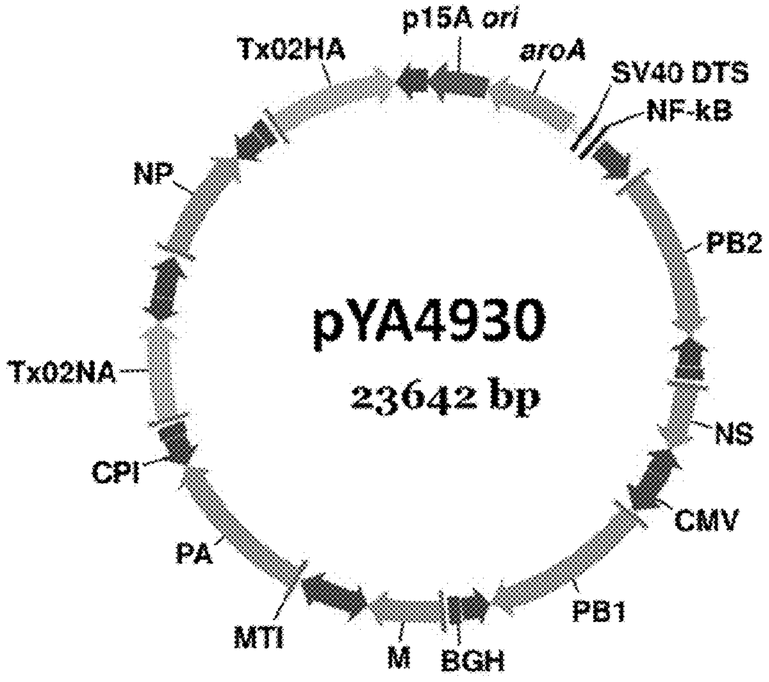

Based on these considerations, the Tx02HA and Tx02NA genes were amplified from influenza A virus (A/chicken/TX/167280-4/02(H5N3) by RT-PCR and cloned between CPI and MTI in the p15A ori plasmids pYA4591 and pYA4592 to generate plasmids pYA4593 and pYA4592-Tx02NA. The CPI-Tx02HA-MTI cassette was amplified from pYA4593 to replace the WSN HA cassette in pYA4519 to obtain plasmid pYA4693. The CPI-Tx02NA-MTI cassette was amplified from pYA4592-Tx02NA to replace the WSN NA cassette in pYA4693 to obtain plasmid pYA4929 (FIG. 12A). Subsequently, the cat and kan markers in pYA4929 were replaced with aroA cassette derived from pYA4784 which is p15A ori based $AroA^+$ vector. The resulting plasmid was designated as pAY4930 (FIG. 12B). Both pYA4929 and pYA4930 were designed to yield an avian influenza virus of low pathogenicity suitable for immunization of poultry. In other applications, the sequence encoding the influenza virus could be modified to attenuate the strain's ability to cause disease symptoms without eliminating or adversely altering its immunogenicity, such that the immunized bird (animal) develops protective immunity against influenza virus.

Another feasible alternative is to directly inject this plasmid construct into the target host using a gene gun to also result in the generation of live attenuated influenza virus, which can also stimulate a protective immune response against other related pathogenic strains of influenza virus.

One can also vaccinate in ovo either by directly injecting the plasmid DNA into the embryonated chicken eggs or by bacterial carrier-mediated delivery to generate live attenuated influenza vaccine. Viral yield by direct injection of the plasmid DNA is at least 1000-fold lower than that obtained by delivering the plasmid construct via a bacterial carrier.

Example 11

Ongoing Studies

Figure 13A:
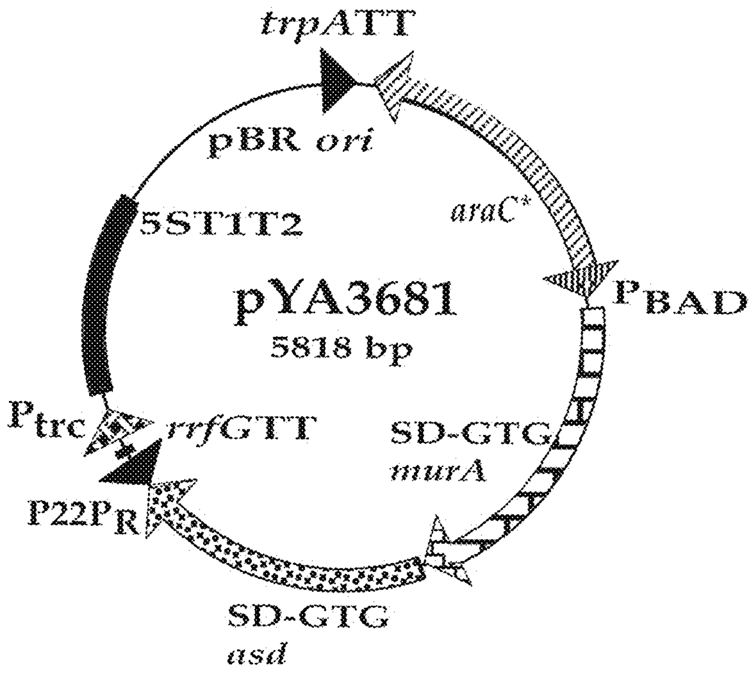
FIG. 13 depicts plasmids pYA3681, pYA4594, pYA4589 and pYA4595. These plasmids express both asd and murA genes under the regulation of the araC $P_{BAD}$ activator-promoter.
Figure 13B:
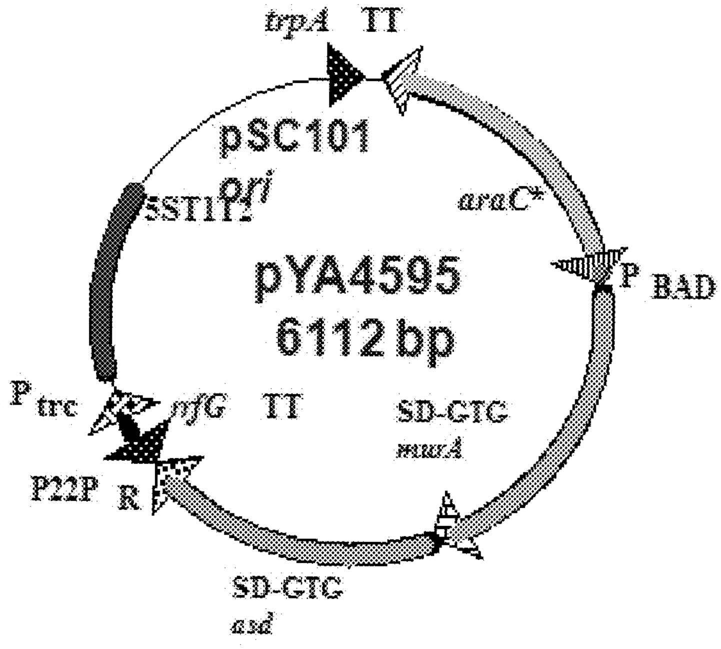
Figure 13C:
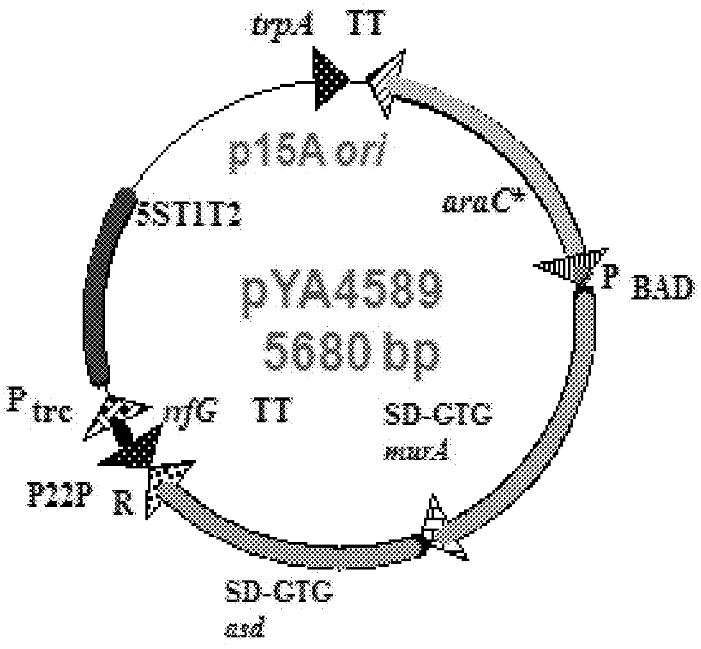
Figure 13D:
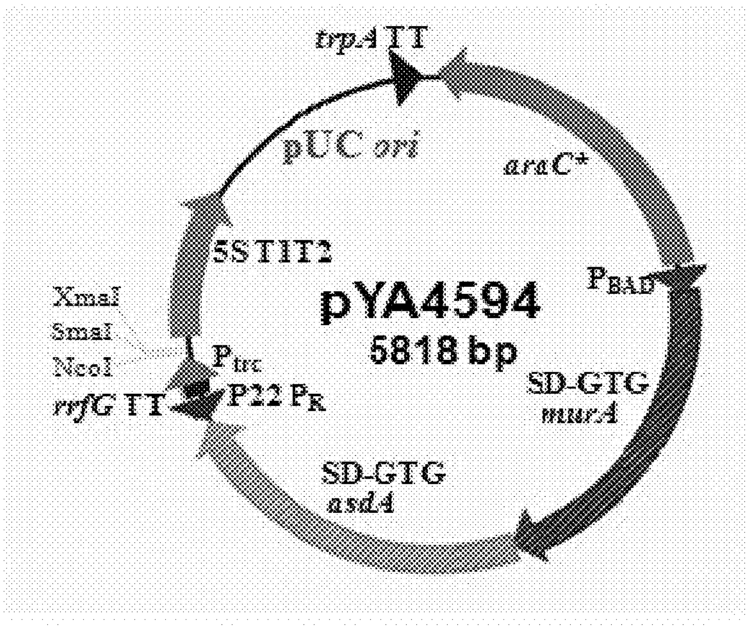

Our laboratory has earlier constructed a "lysis-vector" pYA3681 (FIG. 13) for the regulated delayed lysis system (15). This vector can be used in conjunction with any *Salmonella* strain containing asd and $\Delta P_{murA}$::TT araC $P_{BAD}$ murA mutations, as seen in both strain genotypes described below. Three different derivatives of pYA3681 have been constructed by replacing the origin of replication: pSC101 ori (pYA4595, FIG. 13B), p15A ori (pYA4589, FIG. 13C), and pUC ori (pYA4594, FIG. 13D). Each of these plasmids can complement the ΔasdA27::TT araC $P_{BAD}$ c2 and $\Delta P_{murA25}$::TT araC $P_{BAD}$ murA mutations in a *Salmonella* strain to form a regulated delayed lysis in vivo system. For example, a *Salmonella* strain carrying such a plasmid can be cultured in LB medium supplemented with 0.2% arabinose, and behaves as a wild-type strain in terms of colonization and invasion of the host. The ΔaraBAD23 mutation in turn compromises the ability of the bacterium to metabolize arabinose. Replication of bacteria in the absence of arabinose (conditions encountered in vivo) causes cessation in synthesis of Asd and MurA enzymes, which are continuously diluted at each cell division. This ultimately results in lysis of the strain and release of the bacterial cell contents, including the plasmid expression vector DNA, into the host cell cytoplasm. Compared to the direct lysis system (Examples 6, 8 and 9), the regulated delayed lysis in vivo system can improve *Salmonella*-mediated plasmid delivery in vivo. The plasmids with different copy numbers allow one to pre-select the timing (number of cell divisions) for *Salmonella* cells to begin lysing after animal inoculation/immunization.

Vaccine Strain:

We have generated various *Salmonella Typhimurium* strains listed below. We are proposing to introduce ΔrecA62 or ΔrecF126 into some strains to enhance stable maintenance of the expression vector. In other cases, we need to add ΔsifA26 or ΔendA2311 to enable escape from the endosome or prevent endonuclease cutting of released plasmid DNA, respectively. In other cases, the ΔaroA21426 mutation is added to maintain the single 8-unit plasmid specifying synthesis and assembly of influenza virus.

χ11017: ΔasdA27::TT araC $P_{BAD}$ c2 ΔaraBAD23 Δ(gmd-fcl)-26 Δpmi-2426 ΔrelA198::TT araC $P_{BAD}$ lacI TT $\Delta P_{murA25}$::TT araC $P_{BAD}$ murA χ11020: ΔasdA27::TT araC $P_{BAD}$ c2 ΔaraBAD23 Δ(gmd-fcl)-26 Δpmi-2426 ΔrelA198::TT araC $P_{BAD}$ lacI TT $\Delta P_{murA25}$::TT araC $P_{BAD}$ murA ΔaroA21319

χ11228: ΔasdA27::TT araC $P_{BAD}$ c2 $\Delta P_{murA25}$::TT araC $P_{BAD}$ murA ΔaraBAD23 Δ (gmd-fcl)-26 ΔrelA198::araC $P_{BAD}$ lacI TTΔpmi-2426 ΔtlpA181 ΔsseL116

χ11326: ΔasdA27::TT araC $P_{BAD}$ c2 $\Delta P_{murA25}$::TT araC $P_{BAD}$ murA ΔaraBAD23 Δ(gmd-fcl)-26 ΔrelA198::araC $P_{BAD}$ lacI TTΔpmi-2426 ΔtlpA181 ΔsseL116 ΔsifA26

χ11327: ΔasdA27::TT araC $P_{BAD}$ c2 $\Delta P_{murA25}$::TT araC $P_{BAD}$ murA ΔaraBAD23 Δ(gmd-fcl)-26 ΔrelA198::araC $P_{BAD}$ lacI TTΔpmi-2426 ΔtlpA181 ΔsseL116 $\Delta P_{hilA}$::$P_{trc\ \Delta lacO888}$ hilA ΔsifA26

χ11233: ΔasdA27::TT araC $P_{BAD}$ c2 $\Delta P_{murA25}$::TT araC $P_{BAD}$ murA Δ(araC $P_{BAD}$)-5::P22 $P_R$ araBAD Δ(gmd-fcl)-26 ΔrelA198::araC $P_{BAD}$ lacI TT Δpmi-2426 ΔaroA21419 $\Delta P_{hilA}$::$P_{trc\ \Delta lacO888}$ hilA Vaccine Vector:

We have constructed a 8-unit plasmid pYA4930 with a wild-type aroA cassette (FIG. 12). This will serve two purposes: a) complementation of the ΔaroA21419 mutation in χ11020, and b) stable maintenance of pYA4930 in χ11020. AroA is an essential enzyme for the synthesis of various aromatic amino acids and vitamins, hence survival of the *Salmonella* strain with an ΔaroA mutation requires amino acid and/or vitamin supplements in the growth medium. Alternatively, the mutation can be complemented by providing the gene on a plasmid. Here we chose to clone the aroA cassette in the 8-unit plasmid pYA4693, so that, the obligate requirement of the AroA enzyme (in the absence of external aromatic acid supplementation) would ensure stable maintenance of the expression vector in the strain χ11020. Additionally, we have truncated the NS1 gene which could be included in plasmid pYA4930 to attenuate the virus if necessary. Although the likelihood of this plasmid to produce a high pathogenic influenza virus is minimal (see Example 10).

The χ11020-derived strain with recA deletion (or recF deletion) will be harbored with plasmid pYA4930 and one of the lysis vectors (pYA3681, pYA4589, pYA4595, or pYA4594), so that the regulated lysis of the bacterial carrier will mediate the delivery of plasmid pYA4930.

Vaccination:

Chickens will be vaccinated with the above described recombinant strains via three different routes; intranasally, orally, or intramuscularly. The influenza A virus (A/chicken/TX/167280-4/02(H5N3)) is an isolate from White Leghorn chickens. It causes clinical signs, such as wheezing and swollen heads, and belongs to a low pathogenic avian influenza virus (16). This virus will be used to challenge the immunized chickens to evaluate the protection efficiency (clinical symptoms and virus shielding).

REFERENCES

1. Bartlett, J. G. 2006. Planning for avian influenza. Ann. Intern. Med. 145:141-144.
2. Bartlett, J. G., and F. G. Hayden. 2005. Influenza A (H5N1): will it be the next pandemic influenza? Are we ready? Ann. Intern. Med. 143:460-462.
3. CDC. 2008. Update: influenza activity—United States, Sep. 30, 2007-Apr. 5, 2008, and composition of the 2008-09 influenza vaccine. MMWR Morb. Mortal. Wkly Rep. 57:404-409.
4. Chen, Z., A. Aspelund, G. Kemble, and H. Jin. 2006. Genetic mapping of the cold-adapted phenotype of B/Ann Arbor/1/66, the master donor virus for live attenuated influenza vaccines (FluMist). Virology 345:416-423.
5. Curtiss, R., 3rd, S. Y. Wanda, B. M. Gunn, X. Zhang, S. A. Tinge, V. Ananthnarayan, H. Mo, S. Wang, and W. Kong. 2009. *Salmonella enterica* serovar *Typhimurium* strains with regulated delayed attenuation in vivo. Infect. Immun. 77:1071-1082.
6. Dean, D. A. 1997. Import of plasmid DNA into the nucleus is sequence specific. Exp. Cell Res. 230:293-302.
7. Egorov, A., S. Brandt, S. Sereinig, J. Romanova, B. Ferko, D. Katinger, A. Grassauer, G. Alexandrova, H. Katinger, and T. Muster. 1998. Transfectant influenza A viruses with long deletions in the NS1 protein grow efficiently in Vero cells. J. Virol. 72:6437-6441.
8. Enami, M., W. Luytjes, M. Krystal, and P. Palese. 1990. Introduction of site-specific mutations into the genome of influenza virus. Proc. Natl. Acad. Sci. USA 87:3802-3805.
9. Fodor, E., L. Devenish, O. G. Engelhardt, P. Palese, G. G. Brownlee, and A. Garcia-Sastre. 1999. Rescue of influenza A virus from recombinant DNA. J. Virol. 73:9679-9682.
10. Gerdil, C. 2003. The annual production cycle for influenza vaccine. Vaccine 21:1776-1779.
11. Hoffmann, E., G. Neumann, G. Hobom, R. G. Webster, and Y. Kawaoka. 2000. "Ambisense" approach for the generation of influenza A virus: vRNA and mRNA synthesis from one template. Virology 267:310-317.
12. Jin, H., B. Lu, H. Zhou, C. Ma, J. Zhao, C. F. Yang, G. Kemble, and H. Greenberg. 2003. Multiple amino acid residues confer temperature sensitivity to human influenza virus vaccine strains (FluMist) derived from cold-adapted A/Ann Arbor/6/60. Virology 306:18-24.
13. Kilbourne, E. D. 1959. Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest. 38:266-274.
14. Klumpp, K., R. W. Ruigrok, and F. Baudin. 1997. Roles of the influenza virus polymerase and nucleoprotein in forming a functional RNP structure. EMBO J. 16:1248-1257.
15. Kong, W., S. Y. Wanda, X. Zhang, W. Bollen, S. A. Tinge, K. L. Roland, and R. Curtiss, 3rd. 2008. Regulated programmed lysis of recombinant *Salmonella* in host tissues to release protective antigens and confer biological containment. Proc. Natl. Acad. Sci. USA 105:9361-9366.

16. Lee, C. W., D. A. Senne, J. A. Linares, P. R. Woolcock, D. E. Stallknecht, E. Spackman, D. E. Swayne, and D. L. Suarez. 2004. Characterization of recent H5 subtype avian influenza viruses from US poultry. Avian Pathol. 33:288-297.
17. Luytjes, W., M. Krystal, M. Enami, J. D. Parvin, and P. Palese. 1989. Amplification, expression, and packaging of foreign gene by influenza virus. Cell 59:1107-1113.
18. Massin, P., P. Rodrigues, M. Marasescu, S. van der Werf, and N. Naffakh. 2005. Cloning of the chicken RNA polymerase I promoter and use for reverse genetics of influenza A viruses in avian cells. J. Virol. 79:13811-13816.
19. Mesika, A., I. Grigoreva, M. Zohar, and Z. Reich. 2001. A regulated, NF κB-assisted import of plasmid DNA into mammalian cell nuclei. Mol. Ther. 3:653-657.
20. Molinari, N. A., I. R. Ortega-Sanchez, M. L. Messonnier, W. W. Thompson, P. M. Wortley, E. Weintraub, and C. B. Bridges. 2007. The annual impact of seasonal influenza in the US: measuring disease burden and costs. Vaccine 25:5086-5096.
21. Murti, K. G., R. G. Webster, and I. M. Jones. 1988. Localization of RNA polymerases on influenza viral ribonucleoproteins by immunogold labeling. Virology 164:562-566.
22. Neumann, G., K. Fujii, Y. Kino, and Y. Kawaoka. 2005. An improved reverse genetics system for influenza A virus generation and its implications for vaccine production. Proc. Natl. Acad. Sci. USA 102:16825-16829.
23. Neumann, G., T. Watanabe, H. Ito, S. Watanabe, H. Goto, P. Gao, M. Hughes, D. R. Perez, R. Donis, E. Hoffmann, G. Hobom, and Y. Kawaoka. 1999. Generation of influenza A viruses entirely from cloned cDNAs. Proc. Natl. Acad. Sci. USA 96:9345-9350.
24. Neumann, G., A. Zobel, and G. Hobom. 1994. RNA polymerase I-mediated expression of influenza viral RNA molecules. Virology 202:477-479.
25. Noda, T., H. Sagara, A. Yen, A. Takada, H. Kida, R. H. Cheng, and Y. Kawaoka. 2006. Architecture of ribonucleoprotein complexes in influenza A virus particles. Nature 439:490-492.
26. Osterholm, M. T. 2005. Preparing for the next pandemic. N. Engl. J. Med. 352:1839-1842.
27. Ozaki, H., E. A. Govorkova, C. Li, X. Xiong, R. G. Webster, and R. J. Webby. 2004. Generation of high-yielding influenza A viruses in African green monkey kidney (Vero) cells by reverse genetics. J. Virol. 78:1851-1857.
28. Park, M. S., J. Steel, A. Garcia-Sastre, D. Swayne, and P. Palese. 2006. Engineered viral vaccine constructs with dual specificity: avian influenza and Newcastle disease. Proc. Natl. Acad. Sci. USA 103:8203-8208.
29. Quinlivan, M., D. Zamarin, A. Garcia-Sastre, A. Cullinane, T. Chambers, and P. Palese. 2005. Attenuation of equine influenza viruses through truncations of the NS1 protein. J. Virol. 79:8431-8439.
30. Rand, K. N. 1996. Crystal violet can be used to visualize DNA bands during gel electrophoresis and to improve cloning efficiency. Tech. Tips Online. http://www.sciencedirect.com/science/journal/13662120.
31. Schulman, J. L., and E. D. Kilbourne. 1969. Independent variation in nature of hemagglutinin and neuraminidase antigens of influenza virus: distinctiveness of hemagglutinin antigen of Hong Kong-68 virus. Proc. Natl. Acad. Sci. USA 63:326-333.
32. Simonsen, L., K. Fukuda, L. B. Schonberger, and N. J. Cox. 2000. The impact of influenza epidemics on hospitalizations. J. Infect. Dis. 181:831-837.
33. Steel, J., A. C. Lowen, L. Pena, M. Angel, A. Solorzano, R. Albrecht, D. R. Perez, A. Garcia-Sastre, and P. Palese. 2009. Live attenuated influenza viruses containing NS1 truncations as vaccine candidates against H5N1 highly pathogenic avian influenza. J. Virol. 83:1742-1753.
34. Taubenberger, J. K., and D. M. Morens. 2006. 1918 Influenza: the mother of all pandemics. Emerg. Infect. Dis. 12:15-22.
35. Tumpey, T. M., C. F. Basler, P. V. Aguilar, H. Zeng, A. Solorzano, D. E. Swayne, N. J. Cox, J. M. Katz, J. K. Taubenberger, P. Palese, and A. Garcia-Sastre. 2005. Characterization of the reconstructed 1918 Spanish influenza pandemic virus. Science 310:77-80.
36. Webster, R. G., W. J. Bean, O. T. Gorman, T. M. Chambers, and Y. Kawaoka. 1992. Evolution and ecology of influenza A viruses. Microbiol Rev 56:152-79.

37. Zobel, A., G. Neumann, and G. Hobom. 1993. RNA polymerase I catalysed transcription of insert viral cDNA. Nucleic. Acids. Res. 21:3607-3614.

Sequences of this Study.

Influenza A Virus Genes.

All influenza A/WSN/33 virus genes were derived from plasmid pTM-PolI-WSN-All (A gift from Dr. Yoshihiro Kawaoka, University of Wisconsin—Madison). The sequence of each gene was listed as following.

```
>PB2 (SEQ ID NO: 49)
   1  agcgaaagca ggtcaattat attcaatatg gaaagaataa aagaactaag
      gaatctaatg

  61  tcgcagtctc gcactcgcga gatactcaca aaaaccaccg tggaccatat
      ggccataatc

 121  aagaagtaca catcaggaag acaggagaag aacccagcac ttaggatgaa
      atggatgatg

 181  gcaatgaaat atccaattac agcagacaag aggataacgg aaatgattcc
      tgagagaaat

 241  gagcagggac aaactttatg gagtaaaatg aatgacgccg gatcagaccg
      agtgatggta

 301  tcacctctgg ctgtgacatg gtggaatagg aatggaccag tgacaagtac
      agttcattat

 361  ccaaaaatct acaaaactta ttttgaaaaa gtcgaaaggt taaaacatgg
      aacctttggc
```

-continued

```
 421 cctgtccatt ttagaaacca agtcaaaata cgtcgaagag ttgacataaa
     tcctggtcat

 481 gcagatctca gtgccaaaga ggcacaggat gtaatcatgg aagttgtttt
     ccctaacgaa

 541 gtgggagcca ggatactaac atcggaatcg caactaacga caaccaaaga
     gaagaaagaa

 601 gaactccagg gttgcaaaat ttctcctctg atggtggcat acatgttgga
     gagagaactg

 661 gtccgcaaaa cgagattcct cccagtggct ggtggaacaa gcagtgtgta
     cattgaagtg

 721 ttgcatttga cccaaggaac atgctgggaa cagatgtaca ctccaggagg
     ggaggcgagg

 781 aatgatgatg ttgatcaaag cttaattatt gctgctagaa acatagtaag
     aagagccaca

 841 gtatcagcag atccactagc atctttattg gagatgtgcc acagcacgca
     gattggtgga

 901 ataaggatgg taaacatcct taggcagaac ccaacagaag agcaagccgt
     ggatatttgc

 961 aaggctgcaa tgggactgag aattagctca tccttcagtt ttggtggatt
     cacatttaag

1021 agaacaagcg gatcatcagt caagagagag gaagaggtgc ttacgggcaa
     tcttcagaca

1081 ttgaagataa gagtacatga gggatatgaa gagttcacaa tggttgggag
     aagagcaaca

1141 gctatactca gaaaagcaac caggagattg attcagctga tagtgagtgg
     gagagacgaa

1201 cagtcgattg ccgaagcaat aattgtggcc atggtatttt cacaagagga
     ttgtatgata

1261 aaagcagtta gaggtgacct gaatttcgtc aatagggcga atcagcgatt
     gaatcccatg

1321 caccaacttt tgagacattt tcagaaggat gcaaaggtgc tctttcaaaa
     ttggggaatt

1381 gaatccatcg acaatgtgat gggaatgatc gggatattgc ccgacatgac
     tccaagcacc

1441 gagatgtcaa tgagaggagt gagaatcagc aaaatggggg tagatgagta
     ttccagcgcg

1501 gagaagatag tggtgagcat tgaccgtttt ttgagagtta gggaccaacg
     tgggaatgta

1561 ctactgtctc ccgaggagat cagtgaaaca cagggaacag agaaactgac
     aataacttac

1621 tcatcgtcaa tgatgtggga gattaatggt cctgaatcag tgttggtcaa
     tacctatcag

1681 tggatcatca gaaactggga aactgttaaa attcagtggt cccagaatcc
     tacaatgctg

1741 tacaataaaa tggaatttga gccatttcag tctttagttc caaaggccgt
     tagaggccaa

1801 tacagtgggt ttgtgagaac tctgttccaa caaatgaggg atgtgcttgg
     gacatttgat

1861 accgctcaga taataaaact tcttcccttc gcagccgctc caccaaagca
     aagtagaacg

1921 cagttctcct cattgactat aaatgtgagg ggatcaggaa tgagaatact
     tgtaaggggc

1981 aattctccag tattcaacta caacaagacc actaaaagac tcacagttct
     cggaaaggat
```

-continued

```
2041 gctggccctt taactgaaga cccagatgaa ggcacagctg gagttgagtc
     cgcagttctg

2101 agaggattcc tcattctggg caaagaagac aggagatatg gaccagcatt
     aagcataaat

2161 gaactgagca accttgcgaa aggagagaag gctaatgtgc taattgggca
     aggagacgtg

2221 gtgttggtaa tgaaacggaa acggaactct agcatactta ctgacagcca
     gacagcgacc

2281 aaaagaattc ggatggccat caattagtgt cgaatagttt aaaaacgacc
     ttgtttctac

2341 t

>PB1 (SEQ ID NO: 50)
   1 agcgaaagca ggcaaaccat ttgaatggat gtcaatccga ctttactttt
     cttaaaagtg

  61 ccagcacaaa atgctataag cacaactttc ccttatactg gagaccctcc
     ttacagccat

 121 gggacaggaa caggatacac catggatact gtcaacagga cacatcagta
     ctcagaaagg

 181 ggaagatgga caacaaacac cgaaactgga gcaccgcaac tcaacccgat
     tgatgggcca

 241 ctgccagaag acaatgaacc aagtggttat gcccaaacag attgtgtatt
     ggaagcaatg

 301 gccttccttg aggaatccca tcctggtatc tttgagacct cgtgtcttga
     aacgatggag

 361 gttgttcagc aaacacgagt ggacaagctg acacaaggcc gacagaccta
     tgactggact

 421 ctaaatagga accagcctgc tgcaacagca ttggccaaca caatagaagt
     gttcagatca

 481 aatggcctca cggccaatga atctggaagg ctcatagact tccttaagga
     tgtaatggag

 541 tcaatgaaca aagaagaaat ggagatcaca actcattttc agagaaagag
     acgagtgaga

 601 gacaatatga ctaagaaaat ggtgacacag agaacaatag gtaaaaggaa
     gcagagattg

 661 aacaaaagga gttatctaat tagggcatta accctgaaca caatgaccaa
     agatgctgag

 721 agagggaagc taaaacggag agcaattgca accccaggga tgcaaataag
     ggggtttgta

 781 tactttgttg agacactagc aaggagtata tgtgagaaac ttgaacaatc
     aggattgcca

 841 gttggaggca atgagaagaa agcaaagttg gcaaatgttg taaggaagat
     gatgaccaat

 901 tctcaggaca ctgaaatttc tttcaccatc actggagata acaccaaatg
     gaacgaaaat

 961 cagaaccctc ggatgttttt ggccatgatc acatatataa ccagaaatca
     gcccgaatgg

1021 ttcagaaatg ttctaagtat tgctccaata atgttctcaa acaaaatggc
     gagactggga

1081 aaggggtaca tgtttgagag caagagtatg aaaattagaa ctcaaatacc
     tgcagaaatg

1141 ctagcaagca tcgatttgaa atacttcaat gattcaacta gaaagaagat
     tgaaaaaatc

1201 cggccgctct taatagatgg gactgcatca ttgagccctg gaatgatgat
     gggcatgttc
```

-continued

```
1261 aatatgttaa gtactgtatt aggcgtctcc atcctgaatc ttggacaaaa
     gagacacacc

1321 aagactactt actggtggga tggtcttcaa tcttctgatg attttgctct
     gattgtgaat

1381 gcacccaatc atgaagggat tcaagccgga gtcaacaggt tttatcgaac
     ctgtaagcta

1441 cttggaatta atatgagcaa gaaaaagtct tacataaaca gaacaggtac
     atttgaattc

1501 acaagttttt tctatcgtta tgggtttgtt gccaatttca gcatggagct
     tcccagcttt

1561 ggggtgtctg ggatcaacga gtctgcggac atgagtattg gagttactgt
     catcaaaaac

1621 aatatgataa acaatgatct tggtccagca accgctcaaa tggcccttca
     gctgttcatc

1681 aaagattaca ggtacacgta ccggtgccat agaggtgaca cacaaataca
     aacccgaaga

1741 tcatttgaaa taaagaaact gtgggagcaa acccattcca aagctggact
     gctggtctcc

1801 gacggaggcc caaatttata caacattaga aatctccaca ttcctgaagt
     ctgcttgaaa

1861 tgggaattaa tggatgagga ttaccagggg cgtttatgca acccactgaa
     cccatttgtc

1921 aaccataaag acattgaatc agtgaacaat gcagtgataa tgccagcaca
     tggtccagcc

1981 aaaaacatgg agtatgatgc tgttgcaaca acacactcct ggatccccaa
     aagaaatcga

2041 tccatcttga atacaagcca aagaggaata cttgaagatg aacaaatgta
     ccaaaagtgc

2101 tgcaacttat ttgaaaaatt cttccccagc agttcataca gaagaccagt
     cgggatatcc

2161 agtatggtgg aggctatggt ttccagagcc cgaattgatg cacgaattga
     tttcgaatct

2221 ggaaggataa agaaagagga gttcactgag atcatgaaga tctgttccac
     cattgaagag

2281 ctcagacggc aaaaatagtg aatttagctt gtccttcatg aaaaaatgcc
     ttgtttctac

2341 t
```

>PA (SEQ ID NO: 51)

```
   1 agcgaaagca ggtactgatt caaaatggaa gattttgtgc gacaatgctt
     caatccgatg

  61 attgtcgagc ttgcggaaaa ggcaatgaaa gagtatggag aggacctgaa
     aatcgaaaca

 121 aacaaatttg cagcaatatg cactcacttg gaagtgtgct tcatgtattc
     agattttcac

 181 ttcatcgatg agcaaggcga gtcaatagtc gtagaacttg gcgatccaaa
     tgcacttttg

 241 aagcacagat ttgaaataat cgagggaaga gatcgcacaa tagcctggac
     agtaataaac

 301 agtatttgca acactacagg ggctgagaaa ccaaagtttc taccagattt
     gtatgattac

 361 aagaagaata gattcatcga aattggagta acaaggagag aagttcacat
     atactatctg

 421 gaaaaggcca ataaaattaa atctgagaag acacacatcc acattttctc
     attcactggg
```

-continued 481 gaggaaatgg ccacaaaggc cgactacact ctcgatgaag aaagcagggc taggatcaaa 541 accaggctat tcaccataag acaagaaatg gctagcagag gcctctggga ttcctttcgt 601 cagtccgaga gaggcgaaga gacaattgaa gaaagatttg aaatcacagg aacaatgcgc 661 aagcttgccg accaaagtct cccgccaaac ttctccagcc ttgaaaaatt tagagcctat 721 gtggatggat tcgaaccgaa cggctacatt gagggcaagc tttctcaaat gtccaaagaa 781 gtaaatgcta gaattgaacc tttttgaaa tcaacaccac gaccacttag acttccggat 841 gggcctccct gttctcagcg gtccaaattc ctgctgatgg atgccttaaa attaagcatt 901 gaggacccaa gtcatgaggg agaggggata ccgctatatg atgcaatcaa atgcatgaga 961 acattctttg gatggaagga acccaatgtt gttaaaccac acgaaaaggg aataaatcca 1021 aattatcttc tgtcatggaa gcaagtactg gcagaactgc aggacattga gaatgaggag 1081 aaaattccaa ggactaaaaa tatgaagaaa acgagtcagt taaagtgggc acttggtgag 1141 aacatggcac cagaaaaggt agactttgac gattgtaaag atgtaggcga tttgaagcaa 1201 tatgatagtg atgaaccaga attgaggtcg cttgcaagtt ggattcagaa tgagttcaac 1261 aaggcatgtg aactgaccga ttcaagctgg atagagctcg atgagattgg agaagatgcg 1321 gctccaattg aacacattgc aagcatgaga aggaattatt tcacagcaga ggtgtctcat 1381 tgcagagcca cagaatacat aatgaagggg gtgtacatca atactgcctt gcttaatgca 1441 tcctgtgcag caatggatga tttccaatta attccaatga taagcaagtg tagaactaag 1501 gagggaaggc gaaagaccaa tttgtacggt ttcatcataa aaggaagatc ccacttaagg 1561 aatgacaccg atgtggtaaa ctttgtgagc atggagtttt ccctcactga cccaagactt 1621 gaaccacaca aatgggagaa gtactgtgtt cttgaggtag gagatatgct tctaagaagt 1681 gccataggcc atgtgtcaag gcctatgttc ttgtatgtga ggacaaatgg aacctcaaaa 1741 attaaaatga aatgggggat ggaaatgagg cgttgcctcc ttcagtcact tcaacaaatc 1801 gagagtatga ttgaagctga gtcctctgtc aaggagaaag acatgaccaa agagttcttt 1861 gaaaacaaat cagaaacatg gcccgttgga gagtccccca aaggagtgga ggaaggttcc 1921 attgggaagg tctgcagaac tttattggca aagtcggtat tcaacagctt gtatgcatct 1981 ccacaactag aaggattttc agctgaatca agaaaactgc ttcttatcgt tcaggctctt 2041 agggacaacc tggaacctgg gacctttgat cttggggggc tatatgaagc aattgaggag -continued 2101 tgcctgatta atgatccctg ggttttgctt aatgcttctt ggttcaactc cttcctcaca 2161 catgcattga gatagttgtg gcaatgctac tatttgctat ccatactgtc caaaaaagta 2221 ccttgtttct act

>NP (SEQ ID NO: 52)

1 agcaaaagca gggtagataa tcactcacag agtgacatcg aaatcatggc gaccaaaggc 61 accaaacgat cttacgaaca gatggagact gatggagaac gccagaatgc cactgaaatc 121 agagcatctg tcggaaaaat gattgatgga attggacgat tctacatcca aatgtgcacc 181 gaacttaaac tcagtgatta tgagggacgg ctgattcaga acagcttaac aatagagaga 241 atggtgctct ctgcttttga cgagaggagg aataaatatc tagaagaaca tcccagtgcg 301 gggaaagatc ctaagaaaac tggaggacct atatacagga gagtagatgg aaagtggagg 361 agagaactca tcctttatga caaagaagaa ataagacgaa tctggcgcca agctaataat 421 ggtgacgatg caacggctgg tctgactcac atgatgatct ggcactccaa tttgaatgat 481 gcaacttacc agaggacaag agctcttgtt cgcacaggaa tggatcccag gatgtgctca 541 ctgatgcagg gttcaaccct ccctaggagg tctggggccg caggtgctgc agtcaaagga 601 gttggaacaa tggtgatgga attgatcaga atgatcaaac gtgggatcaa tgatcggaac 661 ttctggaggg gtgagaatgg acggagaaca aggattgctt atgaaagaat gtgcaacatt 721 ctcaaaggga aatttcaaac agctgcacaa agaacaatgg tggatcaagt gagagagagc 781 cggaatccag gaaatgctga gttcgaagat ctcatctttt tagcacggtc tgcactcata 841 ttgagagggt cagttgctca caagtcctgc ctgcctgcct gtgtgtatgg atctgccgta 901 gccagtggat acgactttga aagagaggga tactctctag tcggaataga ccctttcaga 961 ctgcttcaaa acagccaagt atacagccta atcagaccaa atgagaatcc agcacacaag 1021 agtcaactgg tgtggatggc atgccattct gctgcatttg aagatctaag agtatcaagc 1081 ttcatcagag ggacgaaagt ggtcccaaga gggaagcttt ccactagagg agttcaaatt 1141 gcttccaatg aaaacatgga gactatggaa tcaagtaccc ttgaactgag aagcagatac 1201 tgggccataa ggaccagaag tggagggaac accaatcaac agagggcttc ctcgggccaa 1261 atcagcatac aacctacgtt ctcagtacag agaaatctcc cttttgacag accaaccatt 1321 atggcagcat tcactgggaa tacagagggg agaacatctg acatgagaac cgaaatcata 1381 aggctgatgg aaagtgcaag accagaagat gtgtctttcc aggggcgggg agtcttcgag -continued

```
1441 ctctcggacg aaaaggcaac gagcccgatc gtgccctcct ttgacatgag
     taatgaagga

1501 tcttatttct tcggagacaa tgcagaggag tacgacaatt aaagaaaaat
     acccttgttt

1561 ctact
```

>HA (SEQ ID NO: 53)

```
   1 agcaaaagca ggggaaaata aaaacaacca aaatgaaggc aaaactactg
     gtcctgttat

  61 atgcatttgt agctacagat gcagacacaa tatgtatagg ctaccatgcg
     aacaactcaa

 121 ccgacactgt tgacacaata ctcgagaaga atgtggcagt gacacattct
     gttaacctgc

 181 tcgaagacag ccacaacggg aaactatgta aattaaaagg aatagcccca
     ctacaattgg

 241 ggaaatgtaa catcaccgga tggctcttgg gaaatccaga atgcgactca
     ctgcttccag

 301 cgagatcatg gtcctacatt gtagaaacac caaactctga gaatggagca
     tgttatccag

 361 gagatctcat cgactatgag gaactgaggg agcaattgag ctcagtatca
     tcattagaaa

 421 gattcgaaat atttcccaag gaaagttcat ggcccaacca cacattcaac
     ggagtaacag

 481 tatcatgctc ccatagggga aaaagcagtt tttacagaaa tttgctatgg
     ctgacgaaga

 541 aggggggattc atacccaaag ctgaccaatt cctatgtgaa caataaaggg
     aaagaagtcc

 601 ttgtactatg ggtgttcat cacccgtcta gcagtgatga gcaacagagt
     ctctatagta

 661 atggaaatgc ttatgtctct gtagcgtctt caaattataa caggagattc
     accccggaaa

 721 tagctgcaag gcccaaagta agagatcaac atgggaggat gaactattac
     tggaccttgc

 781 tagaacccgg agacacaata atatttgagg caactggtaa tctaatagca
     ccatggtatg

 841 ctttcgcact gagtagaggg tttgagtccg gcatcatcac ctcaaacgcg
     tcaatgcatg

 901 agtgtaacac gaagtgtcaa acaccccagg gagctataaa cagcaatctc
     cctttccaga

 961 atatacaccc agtcacaata ggagagtgcc caaaatatgt caggagtacc
     aaattgagga

1021 tggttacagg actaagaaac atcccatcca ttcaatacag aggtctattt
     ggagccattg

1081 ctggttttat tgaggggggga tggactggaa tgatagatgg atggtatggt
     tatcatcatc

1141 agaatgaaca gggatcaggc tatgcagcgg atcaaaaaag cacacaaaat
     gccattaacg

1201 ggattacaaa caaggtgaac tctgttatcg agaaaatgaa cactcaattc
     acagctgtgg

1261 gtaaagaatt caacaactta gaaaaaagga tggaaaattt aaataaaaaa
     gttgatgatg

1321 ggtttctgga catttggaca tataatgcag aattgttagt tctactggaa
     aatgaaagga

1381 ctttggattt ccatgactta aatgtgaaga atctgtacga gaaagtaaaa
     agccaattaa
```

-continued

```
1441 agaataatgc caaagaaatc ggaaatgggt gttttgagtt ctaccacaag
     tgtgacaatg

1501 aatgcatgga aagtgtaaga aatgggactt atgattatcc aaaatattca
     gaagaatcaa

1561 agttgaacag ggaaaagata gatggagtga aattggaatc aatgggggtg
     tatcagattc

1621 tggcgatcta ctcaactgtc gccagttcac tggtgctttt ggtctccctg
     ggggcaatca

1681 gtttctggat gtgttctaat gggtctttgc agtgcagaat atgcatctga
     gattaggatt

1741 tcagaaatat aaggaaaaac acccttgttt ctact
```

>NA (SEQ ID: 54)

```
   1 agcgaaagca ggagtttaaa tgaatccaaa ccagaaaata ataaccattg
     ggtcaatctg

  61 tatggtagtc ggaataatta gcctaatatt gcaaatagga aatataatct
     caatatggat

 121 tagccattca attcaaaccg gaaatcaaaa ccatactgga atatgcaacc
     aaggcagcat

 181 tacctataaa gttgttgctg ggcaggactc aacttcagtg atattaaccg
     gcaattcatc

 241 tctttgtccc atccgtgggt gggctataca cagcaaagac aatggcataa
     gaattggttc

 301 caaaggagac gtttttgtca taagagagcc ttttatttca tgttctcact
     tggaatgcag

 361 gaccttttt ctgactcaag gcgccttact gaatgacaag cattcaaggg
     ggacctttaa

 421 ggacagaagc ccttataggg ccttaatgag ctgccctgtc ggtgaagctc
     cgtccccgta

 481 caattcaagg tttgaatcgg ttgcttggtc agcaagtgca tgtcatgatg
     gaatgggctg

 541 gctaacaatc ggaatttctg gtccagatga tggagcagtg gctgtattaa
     aatacaaccg

 601 cataataact gaaaccataa aaagttggag gaagaatata ttgagaacac
     aagagtctga

 661 atgtacctgt gtaaatggtt catgttttac cataatgacc gatggcccaa
     gtgatgggct

 721 ggcctcgtac aaaattttca agatcgagaa ggggaaggtt actaaatcga
     tagagttgaa

 781 tgcacctaat tctcactacg aggaatgttc ctgttaccct gataccggca
     aagtgatgtg

 841 tgtgtgcaga gacaattggc acggttcgaa ccgaccatgg gtgtccttcg
     accaaaacct

 901 agattataaa ataggataca tctgcagtgg ggttttcggt gacaacccgc
     gtcccaaaga

 961 tggaacaggc agctgtggcc cagtgtctgc tgatggagca aacggagtaa
     agggattttc

1021 atataagtat ggcaatggtg tttggatagg aaggactaaa agtgacagtt
     ccagacatgg

1081 gtttgagatg atttgggatc ctaatggatg gacagagact gatagtaggt
     tctctatgag

1141 acaagatgtt gtggcaataa ctaatcggtc agggtacagc ggaagtttcg
     ttcaacatcc

1201 tgagctaaca gggctagact gtatgaggcc ttgcttctgg gttgaattaa
     tcagggggct
```

-continued 1261 acctgaggag gacgcaatct ggactagtgg gagcatcatt tctttttgtg
gtgtgaatag 1321 tgatactgta gattggtctt ggccagacgg tgctgagttg ccgttcacca
ttgacaagta 1381 gtttgttcaa aaaactcctt gtttctact

>M (SEQ ID NO: 55)

1 agcaaaagca ggtagatatt gaaagatgag tcttctaacc gaggtcgaaa
cgtacgttct 61 ctctatcgtc ccgtcaggcc ccctcaaagc cgagatcgca cagagacttg
aagatgtctt 121 tgcagggaag aacaccgatc ttgaggttct catggaatgg ctaaagacaa
gaccaatcct 181 gtcacctctg actaagggga ttttaggatt tgtgttcacg ctcaccgtgc
ccagtgagcg 241 gggactgcag cgtagacgct ttgtccaaaa tgctcttaat gggaacggag
atccaaataa 301 catggacaaa gcagttaaac tgtataggaa gcttaagagg gagataacat
tccatggggc 361 caaagaaata gcactcagtt attctgctgg tgcacttgcc agttgtatgg
gcctcatata 421 caacaggatg gggctgtga ccactgaagt ggcatttggc ctggtatgcg
caacctgtga 481 acagattgct gactcccagc atcggtctca taggcaaatg gtgacaacaa
ccaatccact 541 aatcagacat gagaacagaa tggttctagc cagcactaca gctaaggcta
tggagcaaat 601 ggctggatcg agtgagcaag cagcagaggc catggatatt gctagtcagg
ccaggcaaat 661 ggtgcaggcg atgagaaccg ttgggactca tcctagctcc agtgctggtc
taaaagatga 721 tcttcttgaa aatttgcagg cctatcagaa acgaatgggg gtgcagatgc
aacgattcaa 781 gtgatcctct cgtcattgca gcaaatatca ttggaatctt gcacttgata
ttgtggattc 841 ttgatcgtct ttttttcaaa tgcatttatc gtcgctttaa atacggtttg
aaaagagggc 901 cttctacgga aggagtgcca gagtctatga gggaagaata tcgaaaggaa
cagcagaatg 961 ctgtggatgt tgacgatggt cattttgtca acatagagct ggagtaaaaa
actaccttgt 1021 ttctact

>NS (SEQ ID NO: 56)

1 agcaaaagca gggtgacaaa gacataatgg atccaaacac tgtgtcaagc
tttcaggtag 61 attgctttct ttggcatgtc cgcaaaagag ttgcagacca agaactaggt
gatgccccat 121 tccttgatcg gcttcgccga gatcagaagt ccctaagagg aagaggcagc
actcttggtc 181 tggacatcga aacagccacc cgtgctggaa agcaaatagt ggagcggatt
ctgaaggaag 241 aatctgatga ggcactcaaa atgaccatgg cctctgtacc tgcatcgcgc
tacctaactg 301 acatgactct tgaggaaatg tcaaggcact ggttcatgct catgcccaag
cagaaagtgg -continued 361 caggccctct ttgtatcaga atggaccagg cgatcatgga taagaacatc atactgaaag 421 cgaacttcag tgtgattttt gaccggctgg agactctaat attactaagg gccttcaccg 481 aagaggggac aattgttggc gaaatttcac cactgccctc tcttccagga catactgatg 541 aggatgtcaa aaatgcagtt ggggtcctca tcggaggact tgaatggaat aataacacag 601 ttcgagtctc tgaaactcta cagagattcg cttggagaag cagtaatgag aatgggagac 661 ctccactcac tccaaaacag aaacggaaaa tggcgggaac aattaggtca gaagtttgaa 721 gaaataagat ggttgattga agaagtgaga cacagactga agataacaga gaatagtttt 781 gagcaaataa catttatgca agccttacaa ctattgcttg aagtggagca agagataaga 841 actttctcgt ttcagcttat ttaataataa aaaacaccct tgtttctact Plasmid Sequences 1. Plasmid pYA4379 (SEQ ID NO: 57)
Ampicillin resistance gene (amp): complement(4837 . . . 5697)
BGH polyA signal 1433 . . . 1657
CMV promoter 232 . . . 819
Neomycin resistance gene (neo): 2541 . . . 3335
pUC ori complement(4022 . . . 4692)
Chicken PolI promoter (CPI): complement(968 . . . 1382)
Murine PolI terminator (MTI): 901 . . . 941

1 gacggatcgg gagatctccc gatcccctat ggtgcactct cagtacaatc tgctctgatg 61 ccgcatagtt aagccagtat ctgctccctg cttgtgtgtt ggaggtcgct gagtagtgcg 121 cgagcaaaat ttaagctaca acaaggcaag gcttgaccga caattgcatg aagaatctgc 181 ttagggttag gcgttttgcg ctgcttcgcg atgtacgggc cagatatacg cgttgacatt 241 gattattgac tagttattaa tagtaatcaa ttacggggtc attagttcat agcccatata 301 tggagttccg cgttacataa cttacggtaa atggcccgcc tggctgaccg cccaacgacc 361 cccgcccatt gacgtcaata atgacgtatg ttcccatagt aacgccaata gggactttcc 421 attgacgtca atgggtggag tatttacggt aaactgccca cttggcagta catcaagtgt 481 atcatatgcc aagtacgccc cctattgacg tcaatgacgg taaatggccc gcctggcatt 541 atgcccagta catgacctta tgggactttc ctacttggca gtacatctac gtattagtca 601 tcgctattac catggtgatg cggttttggc agtacatcaa tgggcgtgga tagcggtttg 661 actcacgggg atttccaagt ctccacccca ttgacgtcaa tgggagtttg ttttggcacc 721 aaaatcaacg ggactttcca aaatgtcgta acaactccgc cccattgacg caaatgggcg 781 gtaggcgtgt acggtgggag gtctatataa gcagagctct ctggctaact agagaaccca 841 ctgcttactg gcttatcgaa attaatacga ctcactatag ggagacccaa gctggctagc 901 gtgtcgcccg gagtactggt cgacctccga agttgggggg gagcagcagg tggtaccacc 961 tgctcctaca gacgaacata taaggcatcc gaaaaaaacg ttctagtccc ataggcgccg 1021 actaccggca gcggctccga cggcagccga ggtttacctc gacgtaactg gaggtacaaa 1081 attacagcga cgcctctggc agctccggag ctgtagcgcc cccccccaca gccagagcgg -continued

```
1141 ccaagacaat ccgaaacggg gtagacctgg acgcggatcg caagccgccc cggcagcgac

1201 ctctagccgc cgccgcggag agcgcgagac ggtagcaccc gggtagaccg ttccgccgtt

1261 tccgagacgc cccggcagcg acccctagcc gccgccgccg cggagagacc gagccggacg

1321 gtgcccgccg ggaccaggta gaccgttccg ccgtgcccca gccacctccg cgaagcgacc

1381 gaaagggcga attctgcaga aagcttaagt ttaaaccgct gatcagcctc gactgtgcct

1441 tctagttgcc agccatctgt tgtttgcccc tcccccgtgc cttccttgac cctggaaggt

1501 gccactccca ctgtcctttc ctaataaaat gaggaaattg catcgcattg tctgagtagg

1561 tgtcattcta ttctgggggg tggggtgggg caggacagca agggggagga ttgggaagac

1621 aatagcaggc atgctgggga tgcggtgggc tctatggctt ctgaggcgga aagaaccagc

1681 tggggctcta gggggtatcc ccacgcgccc tgtagcggcg cattaagcgc ggcgggtgtg

1741 gtggttacgc gcagcgtgac cgctacactt gccagcgccc tagcgcccgc tcctttcgct

1801 ttcttccctt cctttctcgc cacgttcgcc ggctttcccc gtcaagctct aaatcggggg

1861 ctccctttag ggttccgatt tagtgcttta cggcacctcg accccaaaaa acttgattag

1921 ggtgatggtt cacgtagtgg gccatcgccc tgatagacgg tttttcgccc tttgacgttg

1981 gagtccacgt tctttaatag tggactcttg ttccaaactg gaacaacact caaccctatc

2041 tcggtctatt cttttgattt ataagggatt ttgccgattt cggcctattg gttaaaaaat

2101 gagctgattt aacaaaaatt taacgcgaat taattctgtg gaatgtgtgt cagttagggt

2161 gtggaaagtc cccaggctcc ccagcaggca gaagtatgca aagcatgcat ctcaattagt

2221 cagcaaccag gtgtggaaag tccccaggct ccccagcagg cagaagtatg caaagcatgc

2281 atctcaatta gtcagcaacc atagtcccgc ccctaactcc gcccatcccg cccctaactc

2341 cgcccagttc cgcccattct ccgccccatg gctgactaat tttttttatt tatgcagagg

2401 ccgaggccgc ctctgcctct gagctattcc agaagtagtg aggaggcttt tttggaggcc

2461 taggcttttg caaaaagctc ccgggagctt gtatatccat tttcggatct gatcaagaga

2521 caggatgagg atcgtttcgc atgattgaac aagatggatt gcacgcaggt tctccggccg

2581 cttgggtgga gaggctattc ggctatgact gggcacaaca gacaatcggc tgctctgatg

2641 ccgccgtgtt ccggctgtca gcgcaggggc gcccggttct ttttgtcaag accgacctgt

2701 ccggtgccct gaatgaactg caggacgagg cagcgcggct atcgtggctg gccacgacgg

2761 gcgttccttg cgcagctgtg ctcgacgttg tcactgaagc gggaagggac tggctgctat

2821 tgggcgaagt gccggggcag gatctcctgt catctcacct tgctcctgcc gagaaagtat

2881 ccatcatggc tgatgcaatg cggcggctgc atacgcttga tccggctacc tgcccattcg

2941 accaccaagc gaaacatcgc atcgagcgag cacgtactcg gatggaagcc ggtcttgtcg

3001 atcaggatga tctggacgaa gagcatcagg ggctcgcgcc agccgaactg ttcgccaggc

3061 tcaaggcgcg catgcccgac ggcgaggatc tcgtcgtgac ccatggcgat gcctgcttgc

3121 cgaatatcat ggtggaaaat ggccgctttt ctggattcat cgactgtggc cggctgggtg

3181 tggcggaccg ctatcaggac atagcgttgg ctacccgtga tattgctgaa gagcttggcg

3241 gcgaatgggc tgaccgcttc ctcgtgcttt acggtatcgc cgctcccgat tcgcagcgca

3301 tcgccttcta tcgccttctt gacgagttct tctgagcggg actctggggt tcgaaatgac

3361 cgaccaagcg acgcccaacc tgccatcacg agatttcgat tccaccgccg ccttctatga
```

-continued

```
3421 aaggttgggc ttcggaatcg ttttccggga cgccggctgg atgatcctcc agcgcgggga
3481 tctcatgctg gagttcttcg cccaccccaa cttgtttatt gcagcttata atggttacaa
3541 ataaagcaat agcatcacaa atttcacaaa taaagcattt ttttcactgc attctagttg
3601 tggtttgtcc aaactcatca atgtatctta tcatgtctgt ataccgtcga cctctagcta
3661 gagcttggcg taatcatggt catagctgtt tcctgtgtga aattgttatc cgctcacaat
3721 tccacacaac atacgagccg gaagcataaa gtgtaaagcc tggggtgcct aatgagtgag
3781 ctaactcaca ttaattgcgt tgcgctcact gcccgctttc cagtcgggaa acctgtcgtg
3841 ccagctgcat taatgaatcg gccaacgcgc ggggagaggc ggtttgcgta ttgggcgctc
3901 ttccgcttcc tcgctcactg actcgctgcg ctcggtcgtt cggctgcggc gagcggtatc
3961 agctcactca aaggcggtaa tacggttatc cacagaatca ggggataacg caggaaagaa
4021 catgtgagca aaaggccagc aaaaggccag gaaccgtaaa aaggccgcgt tgctggcgtt
4081 tttccatagg ctccgccccc tgacgagca tcacaaaaat cgacgctcaa gtcagaggtg
4141 gcgaaacccg acaggactat aaagatacca ggcgtttccc cctggaagct ccctcgtgcg
4201 ctctcctgtt ccgaccctgc cgcttaccgg atacctgtcc gcctttctcc cttcgggaag
4261 cgtggcgctt tctcatagct cacgctgtag gtatctcagt tcggtgtagg tcgttcgctc
4321 caagctgggc tgtgtgcacg aaccccccgt tcagcccgac cgctgcgcct tatccggtaa
4381 ctatcgtctt gagtccaacc cggtaagaca cgacttatcg ccactggcag cagccactgg
4441 taacaggatt agcagagcga ggtatgtagg cggtgctaca gagttcttga agtggtggcc
4501 taactacggc tacactagaa gaacagtatt tggtatctgc gctctgctga agccagttac
4561 cttcggaaaa agagttggta gctcttgatc cggcaaacaa accaccgctg gtagcggttt
4621 ttttgtttgc aagcagcaga ttacgcgcag aaaaaaagga tctcaagaag atcctttgat
4681 cttttctacg gggtctgacg ctcagtggaa cgaaaactca cgttaaggga ttttggtcat
4741 gagattatca aaaaggatct tcacctagat ccttttaaat taaaaatgaa gttttaaatc
4801 aatctaaagt atatatgagt aaacttggtc tgacagttac caatgcttaa tcagtgaggc
4861 acctatctca gcgatctgtc tatttcgttc atccatagtt gcctgactcc ccgtcgtgta
4921 gataactacg atacgggagg gcttaccatc tggccccagt gctgcaatga taccgcgaga
4981 cccacgctca ccggctccag atttatcagc aataaaccag ccagccggaa gggccgagcg
5041 cagaagtggt cctgcaactt tatccgcctc catccagtct attaattgtt gccgggaagc
5101 tagagtaagt agttcgccag ttaatagttt gcgcaacgtt gttgccattg ctacaggcat
5161 cgtggtgtca cgctcgtcgt ttggtatggc ttcattcagc tccggttccc aacgatcaag
5221 gcgagttaca tgatccccca tgttgtgcaa aaaagcggtt agctccttcg gtcctccgat
5281 cgttgtcaga agtaagttgg ccgcagtgtt atcactcatg gttatggcag cactgcataa
5341 ttctcttact gtcatgccat ccgtaagatg cttttctgtg actggtgagt actcaaccaa
5401 gtcattctga gaatagtgta tgcggcgacc gagttgctct tgcccggcgt caatacggga
5461 taataccgcg ccacatagca gaactttaaa agtgctcatc attggaaaac gttcttcggg
5521 gcgaaaactc tcaaggatct taccgctgtt gagatccagt tcgatgtaac ccactcgtgc
5581 acccaactga tcttcagcat cttttacttt caccagcgtt tctgggtgag caaaaacagg
5641 aaggcaaaat gccgcaaaaa agggaataag ggcgacacgg aaatgttgaa tactcatact
5701 cttccttttt caatattatt gaagcattta tcagggttat tgtctcatga gcggatacat
5761 atttgaatgt atttagaaaa ataaacaaat aggggttccg cgcacatttc cccgaaaagt
5821 gccacctgac gtc
```

-continued

2. Plasmid pYA4380 (SEQ ID NO: 58)
Ampicillin resistance gene (amp): complement(4191 . . . 5051)
BGH gene polyA signal 787 . . . 1011
Neomycin resistance gene (neo): 1895 . . . 2689
pUC ori complement(3376 . . . 4046)
Murine PolI terminator (MTI): 255 . . . 295
chicken RNA PolI promoter(CPI): complement(322 . . . 736)

```
   1 gacggatcgg gagatctccc gatcccctat ggtgcactct cagtacaatc tgctctgatg
  61 ccgcatagtt aagccagtat ctgctccctg cttgtgtgtt ggaggtcgct gagtagtgcg
 121 cgagcaaaat ttaagctaca acaaggcaag gcttgaccga caattgcatg aagaatctgc
 181 ttagggttag gcgttttgcg ctgcttcgcg atgtacgggc cagatatacg cgttgacatt
 241 gattattgac tagcgtgtcg cccggagtac tggtcgacct ccgaagttgg gggggagcag
 301 caggtggtac cacctgctcc tacagacgaa catataaggc atccgaaaaa aacgttctag
 361 tcccataggc gccgactacc ggcagcggct ccgacggcag ccgaggttta cctcgacgta
 421 actggaggta caaaattaca gcgacgcctc tggcagctcc ggagctgtag cgcccccccc
 481 cacagccaga gcggccaaga caatccgaaa cggggtagac ctggacgcgg atcgcaagcc
 541 gccccggcag cgacctctag ccgccgccgc ggagagcgcg agacggtagc acccgggtag
 601 accgttccgc cgtttccgag acgccccggc agcgacccct agccgccgcc gccgcggaga
 661 gaccgagccg gacggtgccc gccgggacca ggtagaccgt tccgccgtgc cccagccacc
 721 tccgcgaagc gaccgaaagg gcgaattctg cagaaagctt aagtttaaac cgctgatcag
 781 cctcgactgt gccttctagt tgccagccat ctgttgtttg cccctccccc gtgccttcct
 841 tgaccctgga aggtgccact cccactgtcc tttcctaata aaatgaggaa attgcatcgc
 901 attgtctgag taggtgtcat tctattctgg ggggtggggt ggggcaggac agcaaggggg
 961 aggattggga agacaatagc aggcatgctg gggatgcggt gggctctatg gcttctgagg
1021 cggaaagaac cagctggggc tctagggggt atccccacgc gccctgtagc ggcgcattaa
1081 gcgcggcggg tgtggtggtt acgcgcagcg tgaccgctac acttgccagc gccctagcgc
1141 ccgctccttt cgctttcttc ccttcctttc tcgccacgtt cgccggcttt ccccgtcaag
1201 ctctaaatcg ggggctccct ttagggttcc gatttagtgc tttacggcac ctcgacccca
1261 aaaaacttga ttagggtgat ggttcacgta gtgggccatc gccctgatag acggtttttc
1321 gccctttgac gttggagtcc acgttcttta atagtggact cttgttccaa actggaacaa
1381 cactcaaccc tatctcggtc tattcttttg atttataagg gattttgccg atttcggcct
1441 attggttaaa aaatgagctg atttaacaaa aatttaacgc gaattaattc tgtggaatgt
1501 gtgtcagtta gggtgtggaa agtccccagg ctccccagca ggcagaagta tgcaaagcat
1561 gcatctcaat tagtcagcaa ccaggtgtgg aaagtcccca ggctccccag caggcagaag
1621 tatgcaaagc atgcatctca attagtcagc aaccatagtc ccgcccctaa ctccgcccat
1681 cccgccccta actccgccca gttccgccca ttctccgccc catggctgac taattttttt
1741 tatttatgca gaggccgagg ccgcctctgc ctctgagcta ttccagaagt agtgaggagg
1801 cttttttgga ggcctaggct tttgcaaaaa gctcccggga gcttgtatat ccattttcgg
1861 atctgatcaa gagacaggat gaggatcgtt tcgcatgatt gaacaagatg gattgcacgc
1921 aggttctccg gccgcttggg tggagaggct attcggctat gactgggcac aacagacaat
1981 cggctgctct gatgccgccg tgttccggct gtcagcgcag gggcgcccgg ttctttttgt
2041 caagaccgac ctgtccggtg ccctgaatga actgcaggac gaggcagcgc ggctatcgtg
2101 gctggccacg acgggcgttc cttgcgcagc tgtgctcgac gttgtcactg aagcgggaag
```

-continued

```
2161 ggactggctg ctattgggcg aagtgccggg gcaggatctc ctgtcatctc accttgctcc
2221 tgccgagaaa gtatccatca tggctgatgc aatgcggcgg ctgcatacgc ttgatccggc
2281 tacctgccca ttcgaccacc aagcgaaaca tcgcatcgag cgagcacgta ctcggatgga
2341 agccggtctt gtcgatcagg atgatctgga cgaagagcat caggggctcg cgccagccga
2401 actgttcgcc aggctcaagg cgcgcatgcc cgacggcgag gatctcgtcg tgacccatgg
2461 cgatgcctgc ttgccgaata tcatggtgga aaatggccgc ttttctggat tcatcgactg
2521 tggccggctg ggtgtggcgg accgctatca ggacatagcg ttggctaccc gtgatattgc
2581 tgaagagctt ggcggcgaat gggctgaccg cttcctcgtg ctttacggta tcgccgctcc
2641 cgattcgcag cgcatcgcct tctatcgcct tcttgacgag ttcttctgag cgggactctg
2701 gggttcgaaa tgaccgacca agcgacgccc aacctgccat cacgagattt cgattccacc
2761 gccgccttct atgaaaggtt gggcttcgga atcgttttcc gggacgccgg ctggatgatc
2821 ctccagcgcg gggatctcat gctggagttc ttcgcccacc ccaacttgtt tattgcagct
2881 tataatggtt acaaataaag caatagcatc acaaatttca caaataaagc atttttttca
2941 ctgcattcta gttgtggttt gtccaaactc atcaatgtat cttatcatgt ctgtataccg
3001 tcgacctcta gctagagctt ggcgtaatca tggtcatagc tgtttcctgt gtgaaattgt
3061 tatccgctca caattccaca caacatacga gccggaagca taaagtgtaa agcctggggt
3121 gcctaatgag tgagctaact cacattaatt gcgttgcgct cactgcccgc tttccagtcg
3181 ggaaacctgt cgtgccagct gcattaatga atcggccaac gcgcggggag aggcggtttg
3241 cgtattgggc gctcttccgc ttcctcgctc actgactcgc tgcgctcggt cgttcggctg
3301 cggcgagcgg tatcagctca ctcaaaggcg gtaatacggt tatccacaga atcaggggat
3361 aacgcaggaa agaacatgtg agcaaaaggc cagcaaaagg ccaggaaccg taaaaaggcc
3421 gcgttgctgg cgtttttcca taggctccgc ccccctgacg agcatcacaa aaatcgacgc
3481 tcaagtcaga ggtggcgaaa cccgacagga ctataaagat accaggcgtt tccccctgga
3541 agctccctcg tgcgctctcc tgttccgacc ctgccgctta ccggatacct gtccgccttt
3601 ctcccttcgg gaagcgtggc gctttctcat agctcacgct gtaggtatct cagttcggtg
3661 taggtcgttc gctccaagct gggctgtgtg cacgaacccc ccgttcagcc cgaccgctgc
3721 gccttatccg gtaactatcg tcttgagtcc aacccggtaa gacacgactt atcgccactg
3781 gcagcagcca ctggtaacag gattagcaga gcgaggtatg taggcggtgc tacagagttc
3841 ttgaagtggt ggcctaacta cggctacact agaagaacag tatttggtat ctgcgctctg
3901 ctgaagccag ttaccttcgg aaaaagagtt ggtagctctt gatccggcaa acaaaccacc
3961 gctggtagcg gtttttttgt ttgcaagcag cagattacgc gcagaaaaaa aggatctcaa
4021 gaagatcctt tgatcttttc tacggggtct gacgctcagt ggaacgaaaa ctcacgttaa
4081 gggattttgg tcatgagatt atcaaaaagg atcttcacct agatcctttt aaattaaaaa
4141 tgaagtttta aatcaatcta aagtatatat gagtaaactt ggtctgacag ttaccaatgc
4201 ttaatcagtg aggcacctat ctcagcgatc tgtctatttc gttcatccat agttgcctga
4261 ctccccgtcg tgtagataac tacgatacgg gagggcttac catctggccc cagtgctgca
4321 atgataccgc gagacccacg ctcaccggct ccagatttat cagcaataaa ccagccagcc
4381 ggaagggccg agcgcagaag tggtcctgca actttatccg cctccatcca gtctattaat
4441 tgttgccggg aagctagagt aagtagttcg ccagttaata gtttgcgcaa cgttgttgcc
4501 attgctacag gcatcgtggt gtcacgctcg tcgtttggta tggcttcatt cagctccggt
4561 tcccaacgat caaggcgagt tacatgatcc cccatgttgt gcaaaaaagc ggttagctcc
```

-continued

```
4621 ttcggtcctc cgatcgttgt cagaagtaag ttggccgcag tgttatcact catggttatg

4681 gcagcactgc ataattctct tactgtcatg ccatccgtaa gatgcttttc tgtgactggt

4741 gagtactcaa ccaagtcatt ctgagaatag tgtatgcggc gaccgagttg ctcttgcccg

4801 gcgtcaatac gggataatac cgcgccacat agcagaactt taaaagtgct catcattgga

4861 aaacgttctt cggggcgaaa actctcaagg atcttaccgc tgttgagatc cagttcgatg

4921 taacccactc gtgcacccaa ctgatcttca gcatctttta ctttcaccag cgtttctggg

4981 tgagcaaaaa caggaaggca aaatgccgca aaaaagggaa taagggcgac acggaaatgt

5041 tgaatactca tactcttcct ttttcaatat tattgaagca tttatcaggg ttattgtctc

5101 atgagcggat acatatttga atgtatttag aaaaataaac aaataggggt tccgcgcaca

5161 tttccccgaa aagtgccacc tgacgtc
```

3. Plasmid pYA4749 (SEQ ID NO: 59)
Chloramphenicol resistance gene (cat): complement (3519 . . . 219)
p15A ori: 581 . . . 1429
GFP Gene: 1800 . . . 2516
$P_{trc}$ promoter: 1638 . . . 1740
5ST1T2 terminator: 2549 . . . 3052

```
   1 gaattccgga tgagcattca tcaggcgggc aagaatgtga ataaaggccg gataaaactt

  61 gtgcttattt ttctttacgg tctttaaaaa ggccgtaata tccagctgaa cggtctggtt

 121 ataggtacat tgagcaactg actgaaatgc ctcaaaatgt tctttacgat gccattggga

 181 tatatcaacg gtggtatatc cagtgatttt tttctccatt ttagcttcct tagctcctga

 241 aaatctcgat aactcaaaaa atacgcccgg tagtgatctt atttcattat ggtgaaagtt

 301 ggaacctctt acgtgccgat caacgtctca ttttcgccaa aagttggccc agggcttccc

 361 ggtatcaaca gggacaccag gatttattta ttctgcgaag tgatcttccg tcacaggtat

 421 ttattcggcg caaagtgcgt cgggtgatgc tgccaactta ctgatttagt gtatgatggt

 481 gtttttgagg tgctccagtg gcttctgttt ctatcagctg tccctcctgt tcagctactg

 541 acggggtggt gcgtaacggc aaaagcaccg ccggacatca gcgctagcgg agtgtatact

 601 ggcttactat gttggcactg atgagggtgt cagtgaagtg cttcatgtgg caggagaaaa

 661 aaggctgcac cggtgcgtca gcagaatatg tgatacagga tatattccgc ttcctcgctc

 721 actgactcgc tacgctcggt cgttcgactg cggcgagcgg aaatggctta cgaacggggc

 781 ggagatttcc tggaagatgc caggaagata cttaacaggg aagtgagagg gccgcggcaa

 841 agccgttttt ccataggctc cgcccccctg acaagcatca cgaaatctga cgctcaaatc

 901 agtggtggcg aaacccgaca ggactataaa gataccaggc gtttccccct ggcggctccc

 961 tcgtgcgctc tcctgttcct gcctttcggt ttaccggtgt cattccgctg ttatggccgc

1021 gtttgtctca ttccacgcct gacactcagt tccgggtagg cagttcgctc caagctggac

1081 tgtatgcacg aaccccccgt tcagtccgac cgctgcgcct tatccggtaa ctatcgtctt

1141 gagtccaacc cggaaagaca tgcaaaagca ccactggcag cagccactgg taattgattt

1201 agaggagtta gtcttgaagt catgcgccgg ttaaggctaa actgaaagga caagttttgg

1261 tgactgcgct cctccaagcc agttacctcg gttcaaagag ttggtagctc agagaacctt

1321 cgaaaaaccg ccctgcaagg cggttttttc gttttcagag caagagatta cgcgcagacc

1381 aaaacgatct caagaagatc atcttattaa tcagataaaa tatttctaga tcgtccattc

1441 cgacagcatc gccagtcact atggcgtgct gctagcgcta tatgcgttga tgcaatttct

1501 atgcgcaccc gttctcggag cactgtccga ccgctttggc cgccgcccag tcctgctcgc

1561 ttcgctactt ggagccacta tcgactacgc gatcatggcg accacacccg tcctgtgtaa
```

-continued

```
1621 tacgtagaca ctgtgtctcc ggaagacctt ccattctgaa atgagctgtt gacaattaat
1681 catccggctc gtataatgtg tggaattgtg agcggataac aatttcacac aggaaacaga
1741 ccatgggaat tcgagctcgg tacccgggga tcctctagat ttaagaagga gatatacata
1801 tgagtaaagg agaagaactt ttcactggag ttgtcccaat tcttgttgaa ttagatggtg
1861 atgttaatgg gcacaaattt tctgtcagtg gagagggtga aggtgatgca acatacggaa
1921 aacttaccct taaatttatt tgcactactg gaaaactacc tgttccatgg ccaacacttg
1981 tcactacttt cgcgtatggt cttcaatgct ttgcgagata cccagatcat atgaaacagc
2041 atgacttttt caagagtgcc atgcccgaag gttatgtaca ggaaagaact atatttttca
2101 aagatgacgg gaactacaag acacgtgctg aagtcaagtt tgaaggtgat acccttgtta
2161 atagaatcga gttaaaaggt attgatttta aagaagatgg aaacattctt ggacacaaat
2221 tggaatacaa ctataactca cacaatgtat acatcatggc agacaaacaa aagaatggaa
2281 tcaaagttaa cttcaaaatt agacacaaca ttgaagatgg aagcgttcaa ctagcagacc
2341 attatcaaca aaatactcca attggcgatg gccctgtcct tttaccagac aaccattacc
2401 tgtccacaca atctgccctt tcgaaagatc ccaacgaaaa gagagaccac atggtccttc
2461 ttgagtttgt aacagctgct gggattacac atggcatgga tgaactatac aaataaatgt
2521 ccagacctgc agccaagctc ccaagcttgg ctgttttggc ggatgagaga agattttcag
2581 cctgatacag attaaatcag aacgcagaag cggtctgata aaacagaatt tgcctggcgg
2641 cagtagcgcg gtggtcccac ctgaccccat gccgaactca gaagtgaaac gccgtagcgc
2701 cgatggtagt gtggggtctc cccatgcgag agtagggaac tgccaggcat caaataaaac
2761 gaaaggctca gtcgaaagac tgggcctttc gttttatctg ttgtttgtcg gtgaacgctc
2821 tcctgagtag gacaaatccg ccgggagcgg atttgaacgt tgcgaagcaa cggcccggag
2881 ggtggcgggc aggacgcccg ccataaactg ccaggcatca aattaagcag aaggccatcc
2941 tgacggatgg cctttttgcg tttctacaaa ctcttttgtt tatttttcta aatacattca
3001 aatatgtatc cgctcatgag acaataaccc tgataaatgc ttcaataatg gagacacagt
3061 gtcagatctt aaccggcagc gcccaacagt cccccggcca cggggcctgc caccataccc
3121 acgccgaaac aagcgccctg caccattatg ttccggatct gcatcgcagg atgctgctgg
3181 ctaccctgtg gaacacctac atctgtatta acgaagcgct aaccgttttt atcaggctct
3241 gggaggcaga ataaatgatc atatcgtcaa ttattacctc cacggggaga gcctgagcaa
3301 actggcctca ggcatttgag aagcacacgg tcacactgct tccggtagtc aataaaccgg
3361 taaaccagca atagacataa gcggctattt aacgaccctg ccctgaaccg acgaccgggt
3421 cgaatttgct ttcgaatttc tgccattcat ccgcttatta tcacttattc aggcgtagca
3481 ccaggcgttt aagggcacca ataactgcct taaaaaaatt acgccccgcc ctgccactca
3541 tcgcagtact gttgtaattc attaagcatt ctgccgacat ggaagccatc acagacggca
3601 tgatgaacct gaatcgccag cggcatcagc accttgtcgc cttgcgtata atatttgccc
3661 atggtgaaaa cgggggcgaa gaagttgtcc atattggcca cgtttaaatc aaaactggtg
3721 aaactcaccc agggattggc tgagacgaaa aacatattct caataaaccc tttagggaaa
3781 taggccaggt tttcaccgta acacgccaca tcttgcgaat atatgtgtag aaactgccgg
3841 aaatcgtcgt ggtattcact ccagagcgat gaaaacgttt cagtttgctc atggaaaacg
3901 gtgtaacaag ggtgaacact atcccatatc accagctcac cgtctttcat tgccatacg
```

-continued

IV. The 8-unit plasmid pYA4519 (SEQ ID NO: 60)
CPI: complement (5606 . . . 6020)
CPI: complement (7234 . . . 7648)
CPI: complement (10706 . . . 11120)
CPI: complement (12472 . . . 12886)
CPI: complement (15836 . . . 16250)
CPI: complement (17984 . . . 18398)
CPI: complement (20680 . . . 21094)
CPI: complement (23204 . . . 23618)
MTI: 3224 . . . 3264
MTI: 6303 . . . 6343
MTI: 8324 . . . 8364
MTI: 13562 . . . 13602
MTI: 16534 . . . 16574
MTI: 19074 . . . 19114
MTI: 11404 . . . 11444
MTI: 21388 . . . 21428
CMV: 7655 . . . 8242
CMV: 2556 . . . 3142
CMV: 12893 . . . 13480
CMV: 18405 . . . 18992
BGH: 6071 . . . 6295
BGH: 11171 . . . 11395
BGH: 16301 . . . 16525
BGH: 21145 . . . 21369
PB2: 3265 . . . 5605
PB1: 8365 . . . 10705
PA: 13603 . . . 15835
NP: 19115 . . . 20679
HA: 21429 . . . 23203
NA: 16575 . . . 17983
M: 11445 . . . 12471
NS: 6344 . . . 7233
Chloramphenicol resistance gene (cat): 1423 . . . 2082
p15A ori: complement (213 . . . 1061)

```
   1 gccggctaaa gtgtctacgt attacacagg acgggtgtgg tcgccatgat cgcgtagtcg

  61 atagtggctc caagtagcga agcgagcagg actgggcggc ggccaaagcg gtcggacagt

 121 gctccgagaa cgggtgcgca tagaaattgc atcaacgcat atagcgctag cagcacgcca

 181 tagtgactgg cgatgctgtc ggaatggacg atctagaaat attttatctg attaataaga

 241 tgatcttctt gagatcgttt tggtctgcgc gtaatctctt gctctgaaaa cgaaaaaacc

 301 gccttgcagg gcggtttttc gaaggttctc tgagctacca actctttgaa ccgaggtaac

 361 tggcttggag gagcgcagtc accaaaactt gtcctttcag tttagcctta accggcgcat

 421 gacttcaaga ctaactcctc taaatcaatt accagtggct gctgccagtg gtgcttttgc

 481 atgtctttcc gggttggact caagacgata gttaccggat aaggcgcagc ggtcggactg

 541 aacggggggt tcgtgcatac agtccagctt ggagcgaact gcctacccgg aactgagtgt

 601 caggcgtgga atgagacaaa cgcggccata acagcggaat gacaccggta aaccgaaagg

 661 caggaacagg agagcgcacg agggagccgc cagggggaaa cgcctggtat ctttatagtc

 721 ctgtcgggtt tcgccaccac tgatttgagc gtcagatttc gtgatgcttg tcaggggggc

 781 ggagcctatg gaaaaacggc tttgccgcgg ccctctcact tccctgttaa gtatcttcct

 841 ggcatcttcc aggaaatctc cgccccgttc gtaagccatt tccgctcgcc gcagtcgaac

 901 gaccgagcgt agcgagtcag tgagcgagga agcggaatat atcctgtatc acatattctg

 961 ctgacgcacc ggtgcagcct tttttctcct gccacatgaa gcacttcact gacaccctca

1021 tcagtgccaa catagtaagc cagtatacac tccgctagcg ctgatgtccg gcggtgcttt

1081 tgccgttacg caccaccccg tcagtagctg aacaggaggg acagctgata gaaacagaag

1141 ccactggagc acctcaaaaa caccatcata cactaaatca gtaagttggc agcatcaccc

1201 gacgcacttt gcgccgaata aatacctgtg acggaagatc acttcgcaga ataaataaat

1261 cctggtgtcc ctgttgatac cgggaagccc tgggccaact tttggcgaaa atgagacgtt

1321 gatcggcacg taagaggttc caactttcac cataatgaaa taagatcact accgggcgta
```

-continued 1381 tttttgagt tatcgagatt ttcaggagct aaggaagcta aaatggagaa aaaaatcact
1441 ggatatacca ccgttgatat atcccaatgg catcgtaaag aacattttga ggcatttcag
1501 tcagttgctc aatgtaccta taaccagacc gttcagctgg atattacggc ctttttaaag
1561 accgtaaaga aaaataagca caagttttat ccggccttta ttcacattct tgcccgcctg
1621 atgaatgctc atccggaatt ccgtatggca atgaaagacg gtgagctggt gatatgggat
1681 agtgttcacc cttgttacac cgttttccat gagcaaactg aaacgttttc atcgctctgg
1741 agtgaatacc acgacgattt ccggcagttt ctacacatat attcgcaaga tgtggcgtgt
1801 tacggtgaaa acctggccta tttccctaaa gggtttattg agaatatgtt tttcgtctca
1861 gccaatccct gggtgagttt caccagtttt gatttaaacg tggccaatat ggacaacttc
1921 ttcgcccccg ttttcaccat gggcaaatat tatacgcaag gcgacaaggt gctgatgccg
1981 ctggcgattc aggttcatca tgccgtctgt gatggcttcc atgtcggcag aatgcttaat
2041 gaattacaac agtactgcga tgagtggcag ggcggggcgt aattttttta aggcagttat
2101 tggtgccctt aaacgcctgg tgctacgcct gaataagtga taataagcgg atgaatggca
2161 gaaattcgaa agcaaattcg acccggtcgt cggttcaggg cagggtcgtt aaatagccgc
2221 ttatgtctat tgctggttta ccggtttatt gactaccgga agcagtgtga ccgtgtgctt
2281 ctcaaatgcc tgaggccagt ttgctcaggc tctccccgtg gaggtaataa ttgacgatat
2341 gatcatttat tctgcctccc agagcctgat aaaaacggtt agcgcttcgt taatacagat
2401 gtaggtgttc cacagggtag ccagcagcat cctgcgatgc agatccggaa cataatggtg
2461 cagggcgctt gtttcggcgt gggtatggtg gcaggccccg tggccggggg actgttgggc
2521 gctgccggtt aagatctgac acttaagccc gggcgttgac attgattatt gactagttat
2581 taatagtaat caattacggg gtcattagtt catagcccat atatggagtt ccgcgttaca
2641 taacttacgg taaatggccc gcctggctga ccgcccaacg acccccgccc attgacgtca
2701 ataatgacgt atgttcccat agtaacgcca atagggactt tccattgacg tcaatgggtg
2761 gagtatttac ggtaaactgc ccacttggca gtacatcaag tgtatcatat gccaagtacg
2821 ccccctattg acgtcaatga cggtaaatgg cccgcctggc attatgccca gtacatgacc
2881 ttatgggact ttcctacttg gcagtacatc tacgtattag tcatcgctat taccatggtg
2941 atgcggtttt ggcagtacat caatgggcgt ggatagcggt ttgactcacg gggatttcca
3001 agtctccacc ccattgacgt caatgggagt ttgttttggc accaaaatca acgggacttt
3061 ccaaaatgtc gtaacaactc cgccccattg acgcaaatgg gcggtaggcg tgtacggtgg
3121 gaggtctata taagcagagc tctctggcta actagagaac ccactgctta ctggcttatc
3181 gaaattaata cgactcacta tagggagacc caagctggct agcgtgtcgc ccggagtact
3241 ggtcgacctc cgaagttggg ggggagcgaa agcaggtcaa ttatattcaa tatggaaaga
3301 ataaaagaac taaggaatct aatgtcgcag tctcgcactc gcgagatact cacaaaaacc
3361 accgtggacc atatggccat aatcaagaag tacacatcag gaagacagga gaagaaccca
3421 gcacttagga tgaaatggat gatggcaatg aaatatccaa ttacagcaga caagaggata
3481 acggaaatga ttcctgagag aaatgagcag ggacaaactt tatggagtaa aatgaatgac
3541 gccggatcag accgagtgat ggtatcacct ctggctgtga catggtggaa taggaatgga
3601 ccagtgacaa gtacagttca ttatccaaaa atctacaaaa cttattttga aaaagtcgaa
3661 aggttaaaac atggaacctt tggccctgtc cattttagaa accaagtcaa aatacgtcga
3721 agagttgaca taaatcctgg tcatgcagat ctcagtgcca aagaggcaca ggatgtaatc -continued 3781 atggaagttg ttttccctaa cgaagtggga gccaggatac taacatcgga atcgcaacta 3841 acgacaacca aagagaagaa agaagaactc cagggttgca aaatttctcc tctgatggtg 3901 gcatacatgt tggagagaga actggtccgc aaaacgagat tcctcccagt ggctggtgga 3961 acaagcagtg tgtacattga agtgttgcat ttgacccaag gaacatgctg ggaacagatg 4021 tacactccag gaggggaggc gaggaatgat gatgttgatc aaagcttaat tattgctgct 4081 agaaacatag taagaagagc cacagtatca gcagatccac tagcatcttt attggagatg 4141 tgccacagca cgcagattgg tggaataagg atggtaaaca tccttaggca gaacccaaca 4201 gaagagcaag ccgtggatat ttgcaaggct gcaatgggac tgagaattag ctcatccttc 4261 agttttggtg gattcacatt taagagaaca agcggatcat cagtcaagag agaggaagag 4321 gtgcttacgg gcaatcttca gacattgaag ataagagtac atgagggata tgaagagttc 4381 acaatggttg ggagaagagc aacagctata ctcagaaaag caaccaggag attgattcag 4441 ctgatagtga gtgggagaga cgaacagtcg attgccgaag caataattgt ggccatggta 4501 ttttcacaag aggattgtat gataaaagca gttagaggtg acctgaattt cgtcaatagg 4561 gcgaatcagc gattgaatcc catgcaccaa cttttgagac attttcagaa ggatgcaaag 4621 gtgctctttc aaaattgggg aattgaatcc atcgacaatg tgatgggaat gatcgggata 4681 ttgcccgaca tgactccaag caccgagatg tcaatgagag gagtgagaat cagcaaaatg 4741 ggggtagatg agtattccag cgcggagaag atagtggtga gcattgaccg tttttttgaga 4801 gttagggacc aacgtgggaa tgtactactg tctcccgagg agatcagtga aacacaggga 4861 acagagaaac tgacaataac ttactcatcg tcaatgatgt gggagattaa tggtcctgaa 4921 tcagtgttgg tcaataccta tcagtggatc atcagaaact gggaaactgt taaaattcag 4981 tggtcccaga atcctacaat gctgtacaat aaaatggaat ttgagccatt tcagtcttta 5041 gttccaaagg ccgttagagg ccaatacagt gggtttgtga gaactctgtt ccaacaaatg 5101 agggatgtgc ttgggacatt tgataccgct cagataataa aacttcttcc cttcgcagcc 5161 gctccaccaa agcaaagtag aacgcagttc tcctcattga ctataaatgt gaggggatca 5221 ggaatgagaa tacttgtaag ggcaattcct ccagtattca actacaacaa gaccactaaa 5281 agactcacag ttctcggaaa ggatgctggc cctttaactg aagacccaga tgaaggcaca 5341 gctggagttg agtccgcagt tctgagagga ttcctcattc tgggcaaaga agacaggaga 5401 tatggaccag cattaagcat aaatgaactg agcaaccttg cgaaaggaga gaaggctaat 5461 gtgctaattg ggcaaggaga cgtggtgttg gtaatgaaac ggaaacggaa ctctagcata 5521 cttactgaca gccagacagc gaccaaaaga attcggatgg ccatcaatta gtgtcgaata 5581 gtttaaaaac gaccttgttt ctactacaga cgaacatata aggcatccga aaaaaacgtt 5641 ctagtcccat aggcgccgac taccggcagc ggctccgacg gcagccgagg tttacctcga 5701 cgtaactgga ggtacaaaat tacagcgacg cctctggcag ctccggagct gtagcgcccc 5761 cccccacagc cagagcggcc aagacaatcc gaaacggggt agacctggac gcggatcgca 5821 agccgccccg gcagcgacct ctagccgccg ccgcggagag cgcgagacgg tagcacccgg 5881 gtagaccgtt ccgccgtttc cgagacgccc cggcagcgac ccctagccgc cgccgccgcg 5941 gagagaccga gccggacggt gcccgccggg accaggtaga ccgttccgcc gtgccccagc 6001 cacctccgcg aagcgaccga aagggcgaat tctgcagaaa gcttaagttt aaaccgctga 6061 tcagcctcga ctgtgccttc tagttgccag ccatctgttg tttgcccctc ccccgtgcct 6121 tccttgaccc tggaaggtgc cactcccact gtcctttcct aataaaatga ggaaattgca 6181 tcgcattgtc tgagtaggtg tcattctatt ctggggggtg gggtggggca ggacagcaag -continued 6241 ggggaggatt gggaagacaa tagcaggcat gctggggatg cggtgggctc tatggcggcc
6301 gcgtgtcgcc cggagtactg gtcgacctcc gaagttgggg gggagcaaaa gcagggtgac
6361 aaagacataa tggatccaaa cactgtgtca agctttcagg tagattgctt tctttggcat
6421 gtccgcaaaa gagttgcaga ccaagaacta ggtgatgccc cattccttga tcggcttcgc
6481 cgagatcaga agtccctaag aggaagaggc agcactcttg gtctggacat cgaaacagcc
6541 acccgtgctg gaaagcaaat agtggagcgg attctgaagg aagaatctga tgaggcactc
6601 aaaatgacca tggcctctgt acctgcatcg cgctacctaa ctgacatgac tcttgaggaa
6661 atgtcaaggc actggttcat gctcatgccc aagcagaaag tggcaggccc tctttgtatc
6721 agaatggacc aggcgatcat ggataagaac atcatactga aagcgaactt cagtgtgatt
6781 tttgaccggc tggagactct aatattacta agggccttca ccgaagaggg gacaattgtt
6841 ggcgaaattt caccactgcc ctctcttcca ggacatactg atgaggatgt caaaaatgca
6901 gttggggtcc tcatcggagg acttgaatgg aataataaca cagttcgagt ctctgaaact
6961 ctacagagat tcgcttggag aagcagtaat gagaatggga gacctccact cactccaaaa
7021 cagaaacgga aaatggcggg aacaattagg tcagaagttt gaagaaataa gatggttgat
7081 tgaagaagtg agacacagac tgaagataac agagaatagt tttgagcaaa taacatttat
7141 gcaagcctta caactattgc ttgaagtgga gcaagagata agaactttct cgtttcagct
7201 tatttaataa taaaaaacac ccttgtttct actacagacg aacatataag gcatccgaaa
7261 aaaacgttct agtcccatag gcgccgacta ccggcagcgg ctccgacggc agccgaggtt
7321 tacctcgacg taactggagg tacaaaatta cagcgacgcc tctggcagct ccggagctgt
7381 agcgcccccc cccacagcca gagcggccaa gacaatccga aacggggtag acctggacgc
7441 ggatcgcaag ccgccccggc agcgacctct agccgccgcc gcggagagcg cgagacggta
7501 gcacccgggt agaccgttcc gccgtttccg agacgccccg gcagcgaccc ctagccgccg
7561 ccgccgcgga gagaccgagc cggacggtgc ccgccgggac caggtagacc gttccgccgt
7621 gccccagcca cctccgcgaa gcgaccgagc gcgcgttgac attgattatt gactagttat
7681 taatagtaat caattacggg gtcattagtt catagcccat atatggagtt ccgcgttaca
7741 taacttacgg taaatggccc gcctggctga ccgcccaacg acccccgccc attgacgtca
7801 ataatgacgt atgttcccat agtaacgcca atagggactt tccattgacg tcaatgggtg
7861 gagtatttac ggtaaactgc ccacttggca gtacatcaag tgtatcatat gccaagtacg
7921 ccccctattg acgtcaatga cggtaaatgg cccgcctggc attatgccca gtacatgacc
7981 ttatgggact ttcctacttg gcagtacatc tacgtattag tcatcgctat taccatggtg
8041 atgcggtttt ggcagtacat caatgggcgt ggatagcggt ttgactcacg gggatttcca
8101 agtctccacc ccattgacgt caatgggagt ttgttttggc accaaaatca acgggacttt
8161 ccaaaatgtc gtaacaactc cgccccattg acgcaaatgg gcggtaggcg tgtacggtgg
8221 gaggtctata taagcagagc tctctggcta actagagaac ccactgctta ctggcttatc
8281 gaaattaata cgactcacta tagggagacc caagctggct agcgtgtcgc ccggagtact
8341 ggtcgacctc cgaagttggg ggggagcgaa agcaggcaaa ccatttgaat ggatgtcaat
8401 ccgactttac ttttcttaaa agtgccagca caaaatgcta taagcacaac tttcccttat
8461 actggagacc ctccttacag ccatgggaca ggaacaggat acaccatgga tactgtcaac
8521 aggacacatc agtactcaga aaggggaaga tggacaacaa acaccgaaac tggagcaccg
8581 caactcaacc cgattgatgg gccactgcca gaagacaatg aaccaagtgg ttatgcccaa -continued

```
 8641 acagattgtg tattggaagc aatggccttc cttgaggaat cccatcctgg tatctttgag
 8701 acctcgtgtc ttgaaacgat ggaggttgtt cagcaaacac gagtggacaa gctgacacaa
 8761 ggccgacaga cctatgactg gactctaaat aggaaccagc ctgctgcaac agcattggcc
 8821 aacacaatag aagtgttcag atcaaatggc ctcacggcca atgaatctgg aaggctcata
 8881 gacttcctta aggatgtaat ggagtcaatg aacaaagaag aaatggagat cacaactcat
 8941 tttcagagaa agagacgagt gagagacaat atgactaaga aaatggtgac acagagaaca
 9001 ataggtaaaa ggaagcagag attgaacaaa aggagttatc taattagggc attaaccctg
 9061 aacacaatga ccaaagatgc tgagagaggg aagctaaaac ggagagcaat tgcaacccca
 9121 gggatgcaaa taagggggtt tgtatacttt gttgagacac tagcaaggag tatatgtgag
 9181 aaacttgaac aatcaggatt gccagttgga ggcaatgaga agaaagcaaa gttggcaaat
 9241 gttgtaagga agatgatgac caattctcag gacactgaaa tttctttcac catcactgga
 9301 gataacacca aatggaacga aaatcagaac cctcggatgt tttggccat gatcacatat
 9361 ataaccagaa atcagcccga atggttcaga aatgttctaa gtattgctcc aataatgttc
 9421 tcaaacaaaa tggcgagact gggaaagggg tacatgtttg agagcaagag tatgaaaatt
 9481 agaactcaaa tacctgcaga aatgctagca agcatcgatt tgaaatactt caatgattca
 9541 actagaaaga agattgaaaa aatccggccg ctcttaatag atgggactgc atcattgagc
 9601 cctggaatga tgatgggcat gttcaatatg ttaagtactg tattaggcgt ctccatcctg
 9661 aatcttggac aaaagagaca caccaagact acttactggt gggatggtct tcaatcttct
 9721 gatgattttg ctctgattgt gaatgcaccc aatcatgaag ggattcaagc cggagtcaac
 9781 aggttttatc gaacctgtaa gctacttgga attaatatga gcaagaaaaa gtcttacata
 9841 aacagaacag gtacatttga attcacaagt tttttctatc gttatgggtt tgttgccaat
 9901 ttcagcatgg agcttcccag ctttggggtg tctgggatca acgagtctgc ggacatgagt
 9961 attggagtta ctgtcatcaa aaacaatatg ataaacaatg atcttggtcc agcaaccgct
10021 caaatggccc ttcagctgtt catcaaagat tacaggtaca cgtaccggtg ccatagaggt
10081 gacacacaaa tacaaacccg aagatcattt gaaataaaga aactgtggga gcaaacccat
10141 tccaaagctg gactgctggt ctccgacgga ggcccaaatt tatacaacat tagaaatctc
10201 cacattcctg aagtctgctt gaaatgggaa ttaatggatg aggattacca ggggcgttta
10261 tgcaacccac tgaacccatt tgtcaaccat aaagacattg aatcagtgaa caatgcagtg
10321 ataatgccag cacatggtcc agccaaaaac atggagtatg atgctgttgc aacaacacac
10381 tcctggatcc ccaaaagaaa tcgatccatc ttgaatacaa gccaaagagg aatacttgaa
10441 gatgaacaaa tgtaccaaaa gtgctgcaac ttatttgaaa aattcttccc cagcagttca
10501 tacagaagac cagtcgggat atccagtatg gtggaggcta tggtttccag agcccgaatt
10561 gatgcacgaa ttgatttcga atctggaagg ataaagaaag aggagttcac tgagatcatg
10621 aagatctgtt ccaccattga agagctcaga cggcaaaaat agtgaattta gcttgtcctt
10681 catgaaaaaa tgccttgttt ctactacaga cgaacatata aggcatccga aaaaaacgtt
10741 ctagtcccat aggcgccgac taccggcagc ggctccgacg gcagccgagg tttacctcga
10801 cgtaactgga ggtacaaaat tacagcgacg cctctggcag ctccggagct gtagcgcccc
10861 cccccacagc cagagcggcc aagacaatcc gaaacggggt agacctggac gcggatcgca
10921 agccgccccg gcagcgacct ctagccgccg ccgcggagag cgcgagacgg tagcacccgg
10981 gtagaccgtt ccgccgtttc cgagacgccc cggcagcgac ccctagccgc cgccgccgcg
11041 gagagaccga gccggacggt gcccgccggg accaggtaga ccgttccgcc gtgccccagc
```

-continued 11101 cacctccgcg aagcgaccga aagggcgaat tctgcagaaa gcttaagttt aaaccgctga
11161 tcagcctcga ctgtgccttc tagttgccag ccatctgttg tttgcccctc ccccgtgcct
11221 tccttgaccc tggaaggtgc cactcccact gtcctttcct aataaaatga ggaaattgca
11281 tcgcattgtc tgagtaggtg tcattctatt ctggggggtg gggtggggca ggacagcaag
11341 ggggaggatt gggaagacaa tagcaggcat gctggggatg cggtgggctc tatggcctgc
11401 agggtgtcgc ccggagtact ggtcgacctc cgaagttggg ggggagcaaa agcaggtaga
11461 tattgaaaga tgagtcttct aaccgaggtc gaaacgtacg ttctctctat cgtcccgtca
11521 ggccccctca aagccgagat cgcacagaga cttgaagatg tctttgcagg gaagaacacc
11581 gatcttgagg ttctcatgga atggctaaag acaagaccaa tcctgtcacc tctgactaag
11641 gggattttag gatttgtgtt cacgctcacc gtgcccagtg agcggggact gcagcgtaga
11701 cgctttgtcc aaaatgctct taatgggaac ggagatccaa ataacatgga caaagcagtt
11761 aaactgtata ggaagcttaa gagggagata acattccatg ggggccaaaga aatagcactc
11821 agttattctg ctggtgcact tgccagttgt atgggcctca tatacaacag gatgggggct
11881 gtgaccactg aagtggcatt tggcctggta tgcgcaacct gtgaacagat tgctgactcc
11941 cagcatcggt ctcataggca aatggtgaca acaaccaatc cactaatcag acatgagaac
12001 agaatggttc tagccagcac tacagctaag gctatggagc aaatggctgg atcgagtgag
12061 caagcagcag aggccatgga tattgctagt caggccaggc aaatggtgca ggcgatgaga
12121 accgttggga ctcatcctag ctccagtgct ggtctaaaag atgatcttct tgaaaatttg
12181 caggcctatc agaaacgaat gggggtgcag atgcaacgat tcaagtgatc ctctcgtcat
12241 tgcagcaaat atcattggaa tcttgcactt gatattgtgg attcttgatc gtcttttttt
12301 caaatgcatt tatcgtcgct ttaaatacgg tttgaaaaga gggccttcta cggaaggagt
12361 gccagagtct atgagggaag aatatcgaaa ggaacagcag aatgctgtgg atgttgacga
12421 tggtcatttt gtcaacatag agctggagta aaaaactacc ttgtttctac tacagacgaa
12481 catataaggc atccgaaaaa aacgttctag tcccataggc gccgactacc ggcagcggct
12541 ccgacggcag ccgaggttta cctcgacgta actggaggta caaaattaca gcgacgcctc
12601 tggcagctcc ggagctgtag cgcccccccc cacagccaga gcggccaaga caatccgaaa
12661 cggggtagac ctggacgcgg atcgcaagcc gccccggcag cgacctctag ccgccgccgc
12721 ggagagcgcg agacggtagc acccgggtag accgttccgc cgtttccgag acgccccggc
12781 agcgacccct agccgccgcc gccgcggaga gaccgagccg gacggtgccc gccgggacca
12841 ggtagaccgt tccgccgtgc cccagccacc tccgcgaagc gaccgaggta ccgttgacat
12901 tgattattga ctagttatta atagtaatca attacggggt cattagttca tagcccatat
12961 atggagttcc gcgttacata acttacggta aatggcccgc ctggctgacc gcccaacgac
13021 ccccgcccat tgacgtcaat aatgacgtat gttcccatag taacgccaat agggactttc
13081 cattgacgtc aatgggtgga gtatttacgg taaactgccc acttggcagt acatcaagtg
13141 tatcatatgc caagtacgcc ccctattgac gtcaatgacg gtaaatggcc cgcctggcat
13201 tatgcccagt acatgacctt atgggacttt cctacttggc agtacatcta cgtattagtc
13261 atcgctatta ccatggtgat gcggttttgg cagtacatca atgggcgtgg atagcggttt
13321 gactcacggg gatttccaag tctccacccc attgacgtca atgggagttt gttttggcac
13381 caaaatcaac gggactttcc aaaatgtcgt aacaactccg ccccattgac gcaaatgggc
13441 ggtaggcgtg tacggtggga ggtctatata agcagagctc tctggctaac tagagaaccc -continued 13501 actgcttact ggcttatcga aattaatacg actcactata gggagaccca agctggctag 13561 cgtgtcgccc ggagtactgg tcgacctccg aagttggggg ggagcgaaag caggtactga 13621 ttcaaaatgg aagattttgt gcgacaatgc ttcaatccga tgattgtcga gcttgcggaa 13681 aaggcaatga aagagtatgg agaggacctg aaaatcgaaa caaacaaatt tgcagcaata 13741 tgcactcact tggaagtgtg cttcatgtat tcagattttc acttcatcga tgagcaaggc 13801 gagtcaatag tcgtagaact tggcgatcca aatgcacttt tgaagcacag atttgaaata 13861 atcgagggaa gagatcgcac aatagcctgg acagtaataa acagtatttg caacactaca 13921 ggggctgaga aaccaaagtt tctaccagat ttgtatgatt acaagaagaa tagattcatc 13981 gaaattggag taacaaggag agaagttcac atatactatc tggaaaaggc caataaaatt 14041 aaatctgaga agacacacat ccacattttc tcattcactg gggaggaaat ggccacaaag 14101 gccgactaca ctctcgatga agaaagcagg gctaggatca aaaccaggct attcaccata 14161 agacaagaaa tggctagcag aggcctctgg gattcctttc gtcagtccga gagaggcgaa 14221 gagacaattg aagaaagatt tgaaatcaca ggaacaatgc gcaagcttgc cgaccaaagt 14281 ctcccgccaa acttctccag ccttgaaaaa tttagagcct atgtggatgg attcgaaccg 14341 aacggctaca ttgagggcaa gctttctcaa atgtccaaag aagtaaatgc tagaattgaa 14401 ccttttttga aatcaacacc acgaccactt agacttccgg atgggcctcc ctgttctcag 14461 cggtccaaat tcctgctgat ggatgcctta aaattaagca ttgaggaccc aagtcatgag 14521 ggagagggga taccgctata tgatgcaatc aaatgcatga gaacattctt tggatggaag 14581 gaacccaatg ttgttaaacc acacgaaaag ggaataaatc caaattatct tctgtcatgg 14641 aagcaagtac tggcagaact gcaggacatt gagaatgagg agaaaattcc aaggactaaa 14701 aatatgaaga aaacgagtca gttaaagtgg gcacttggtg agaacatggc accagaaaag 14761 gtagactttg acgattgtaa agatgtaggc gatttgaagc aatatgatag tgatgaacca 14821 gaattgaggt cgcttgcaag ttggattcag aatgagttca acaaggcatg tgaactgacc 14881 gattcaagct ggatagagct cgatgagatt ggagaagatg cggctccaat tgaacacatt 14941 gcaagcatga gaaggaatta tttcacagca gaggtgtctc attgcagagc cacagaatac 15001 ataatgaagg gggtgtacat caatactgcc ttgcttaatg catcctgtgc agcaatggat 15061 gatttccaat taattccaat gataagcaag tgtagaacta aggagggaag gcgaaagacc 15121 aatttgtacg gtttcatcat aaaaggaaga tcccacttaa ggaatgacac cgatgtggta 15181 aactttgtga gcatggagtt ttccctcact gacccaagac ttgaaccaca caaatgggag 15241 aagtactgtg ttcttgaggt aggagatatg cttctaagaa gtgccatagg ccatgtgtca 15301 aggcctatgt tcttgtatgt gaggacaaat ggaacctcaa aaattaaaat gaaatggggg 15361 atggaaatga ggcgttgcct ccttcagtca cttcaacaaa tcgagagtat gattgaagct 15421 gagtcctctg tcaaggagaa agacatgacc aaagagttct ttgaaaacaa atcagaaaca 15481 tggcccgttg gagagtcccc caaaggagtg gaggaaggtt ccattgggaa ggtctgcaga 15541 actttattgg caaagtcggt attcaacagc ttgtatgcat ctccacaact agaaggattt 15601 tcagctgaat caagaaaact gcttcttatc gttcaggctc ttagggacaa cctggaacct 15661 gggacctttg atcttggggg gctatatgaa gcaattgagg agtgcctgat taatgatccc 15721 tgggttttgc ttaatgcttc ttggttcaac tccttcctca cacatgcatt gagatagttg 15781 tggcaatgct actatttgct atccatactg tccaaaaaag taccttgttt ctactacaga 15841 cgaacatata aggcatccga aaaaaacgtt ctagtcccat aggcgccgac taccggcagc 15901 ggctccgacg gcagccgagg tttacctcga cgtaactgga ggtacaaaat tacagcgacg -continued 15961 cctctggcag ctccggagct gtagcgcccc cccccacagc cagagcggcc aagacaatcc
16021 gaaacggggt agacctggac gcggatcgca agccgccccg gcagcgacct ctagccgccg
16081 ccgcggagag cgcgagacgg tagcacccgg gtagaccgtt ccgccgtttc cgagacgccc
16141 cggcagcgac ccctagccgc cgccgccgcg gagagaccga gccggacggt gcccgccggg
16201 accaggtaga ccgttccgcc gtgccccagc cacctccgcg aagcgaccga aagggcgaat
16261 tctgcagaaa gcttaagttt aaaccgctga tcagcctcga ctgtgccttc tagttgccag
16321 ccatctgttg tttgcccctc ccccgtgcct tccttgaccc tggaaggtgc cactcccact
16381 gtcctttcct aataaaatga ggaaattgca tcgcattgtc tgagtaggtg tcattctatt
16441 ctggggggtg gggtggggca ggacagcaag ggggaggatt gggaagacaa tagcaggcat
16501 gctggggatg cggtgggctc tatggttaat taagtgtcgc ccggagtact ggtcgacctc
16561 cgaagttggg ggggagcgaa agcaggagtt taaatgaatc caaaccagaa aataataacc
16621 attgggtcaa tctgtatggt agtcggaata attagcctaa tattgcaaat aggaaatata
16681 atctcaatat ggattagcca ttcaattcaa accggaaatc aaaaccatac tggaatatgc
16741 aaccaaggca gcattaccta taaagttgtt gctgggcagg actcaacttc agtgatatta
16801 accggcaatt catctctttg tcccatccgt gggtgggcta tacacagcaa agacaatggc
16861 ataagaattg gttccaaagg agacgttttt gtcataagag agccttttat ttcatgttct
16921 cacttggaat gcaggacctt ttttctgact caaggcgcct tactgaatga caagcattca
16981 agggggacct ttaaggacag aagcccttat agggccttaa tgagctgccc tgtcggtgaa
17041 gctccgtccc cgtacaattc aaggtttgaa tcggttgctt ggtcagcaag tgcatgtcat
17101 gatggaatgg gctggctaac aatcggaatt tctggtccag atgatggagc agtggctgta
17161 ttaaaataca accgcataat aactgaaacc ataaaaagtt ggaggaagaa tatattgaga
17221 acacaagagt ctgaatgtac ctgtgtaaat ggttcatgtt ttaccataat gaccgatggc
17281 ccaagtgatg ggctggcctc gtacaaaatt ttcaagatcg agaaggggaa ggttactaaa
17341 tcgatagagt tgaatgcacc taattctcac tacgaggaat gttcctgtta ccctgatacc
17401 ggcaaagtga tgtgtgtgtg cagagacaat tggcacggtt cgaaccgacc atgggtgtcc
17461 ttcgaccaaa acctagatta taaaatagga tacatctgca gtggggtttt cggtgacaac
17521 ccgcgtccca aagatggaac aggcagctgt ggcccagtgt ctgctgatgg agcaaacgga
17581 gtaaagggat tttcatataa gtatggcaat ggtgtttgga taggaaggac taaaagtgac
17641 agttccagac atgggtttga gatgatttgg gatcctaatg gatggacaga gactgatagt
17701 aggttctcta tgagacaaga tgttgtggca ataactaatc ggtcagggta cagcggaagt
17761 ttcgttcaac atcctgagct aacagggcta gactgtatga ggccttgctt ctgggttgaa
17821 ttaatcaggg ggctacctga ggaggacgca atctggacta gtgggagcat catttctttt
17881 tgtggtgtga atagtgatac tgtagattgg tcttggccag acggtgctga gttgccgttc
17941 accattgaca agtagtttgt tcaaaaaact ccttgtttct actacagacg aacatataag
18001 gcatccgaaa aaaacgttct agtcccatag gcgccgacta ccggcagcgg ctccgacggc
18061 agccgaggtt tacctcgacg taactggagg tacaaaatta cagcgacgcc tctggcagct
18121 ccggagctgt agcgcccccc cccacagcca gagcggccaa gacaatccga aacggggtag
18181 acctggacgc ggatcgcaag ccgccccggc agcgacctct agccgccgcc gcggagagcg
18241 cgagacggta gcacccgggt agaccgttcc gccgtttccg agacgccccg gcagcgaccc
18301 ctagccgccg ccgccgcgga gagaccgagc cggacggtgc ccgccgggac caggtagacc -continued 18361 gttccgccgt gccccagcca cctccgcgaa gcgaccgagg gcccgttgac attgattatt 18421 gactagttat taatagtaat caattacggg gtcattagtt catagcccat atatggagtt 18481 ccgcgttaca taacttacgg taaatggccc gcctggctga ccgcccaacg acccccgccc 18541 attgacgtca ataatgacgt atgttcccat agtaacgcca atagggactt tccattgacg 18601 tcaatgggtg gagtatttac ggtaaactgc ccacttggca gtacatcaag tgtatcatat 18661 gccaagtacg ccccctattg acgtcaatga cggtaaatgg cccgcctggc attatgccca 18721 gtacatgacc ttatgggact ttcctacttg gcagtacatc tacgtattag tcatcgctat 18781 taccatggtg atgcggtttt ggcagtacat caatgggcgt ggatagcggt ttgactcacg 18841 gggatttcca agtctccacc ccattgacgt caatgggagt ttgttttggc accaaaatca 18901 acgggacttt ccaaaatgtc gtaacaactc cgccccattg acgcaaatgg gcggtaggcg 18961 tgtacggtgg gaggtctata taagcagagc tctctggcta actagagaac ccactgctta 19021 ctggcttatc gaaattaata cgactcacta tagggagacc caagctggct agcgtgtcgc 19081 ccggagtact ggtcgacctc cgaagttggg ggggagcaaa agcagggtag ataatcactc 19141 acagagtgac atcgaaatca tggcgaccaa aggcaccaaa cgatcttacg aacagatgga 19201 gactgatgga gaacgccaga atgccactga aatcagagca tctgtcggaa aaatgattga 19261 tggaattgga cgattctaca tccaaatgtg caccgaactt aaactcagtg attatgaggg 19321 acggctgatt cagaacagct taacaataga gagaatggtg ctctctgctt ttgacgagag 19381 gaggaataaa tatctagaag aacatcccag tgcggggaaa gatcctaaga aaactggagg 19441 acctatatac aggagagtag atggaaagtg gaggagagaa ctcatccttt atgacaaaga 19501 agaaataaga cgaatctggc gccaagctaa taatggtgac gatgcaacgg ctggtctgac 19561 tcacatgatg atctggcact ccaatttgaa tgatgcaact taccagagga caagagctct 19621 tgttcgcaca ggaatggatc ccaggatgtg ctcactgatg cagggttcaa ccctccctag 19681 gaggtctggg gccgcaggtg ctgcagtcaa aggagttgga acaatggtga tggaattgat 19741 cagaatgatc aaacgtggga tcaatgatcg gaacttctgg aggggtgaga atggacggag 19801 aacaaggatt gcttatgaaa gaatgtgcaa cattctcaaa gggaaatttc aaacagctgc 19861 acaaagaaca atggtggatc aagtgagaga gagccggaat ccaggaaatg ctgagttcga 19921 agatctcatc tttttagcac ggtctgcact catattgaga gggtcagttg ctcacaagtc 19981 ctgcctgcct gcctgtgtgt atggatctgc cgtagccagt ggatacgact ttgaaagaga 20041 gggatactct ctagtcggaa tagacccttt cagactgctt caaaacagcc aagtatacag 20101 cctaatcaga ccaaatgaga atccagcaca caagagtcaa ctggtgtgga tggcatgcca 20161 ttctgctgca tttgaagatc taagagtatc aagcttcatc agagggacga aagtggtccc 20221 aagagggaag ctttccacta gaggagttca aattgcttcc aatgaaaaca tggagactat 20281 ggaatcaagt accettgaac tgagaagcag atactgggcc ataaggacca gaagtggagg 20341 gaacaccaat caacagaggg cttcctcggg ccaaatcagc atacaaccta cgttctcagt 20401 acagagaaat ctcccttttg acagaccaac cattatggca gcattcactg ggaatacaga 20461 ggggagaaca tctgacatga gaaccgaaat cataaggctg atggaaagtg caagaccaga 20521 agatgtgtct ttccaggggc ggggagtctt cgagctctcg gacgaaaagg caacgagccc 20581 gatcgtgccc tcctttgaca tgagtaatga aggatcttat ttcttcggag acaatgcaga 20641 ggagtacgac aattaaagaa aaataccctt gtttctacta cagacgaaca tataaggcat 20701 ccgaaaaaaa cgttctagtc ccataggcgc cgactaccgg cagcggctcc gacggcagcc 20761 gaggtttacc tcgacgtaac tggaggtaca aaattacagc gacgcctctg gcagctccgg -continued

```
20821 agctgtagcg ccccccccca cagccagagc ggccaagaca atccgaaacg gggtagacct
20881 ggacgcggat cgcaagccgc cccggcagcg acctctagcc gccgccgcgg agagcgcgag
20941 acggtagcac ccgggtagac cgttccgccg tttccgagac gccccggcag cgacccctag
21001 ccgccgccgc cgcggagaga ccgagccgga cggtgcccgc cgggaccagg tagaccgttc
21061 cgccgtgccc cagccacctc cgcgaagcga ccgaaagggc gaattctgca gaaagcttaa
21121 gtttaaaccg ctgatcagcc tcgactgtgc cttctagttg ccagccatct gttgtttgcc
21181 cctcccccgt gccttccttg accctggaag gtgccactcc cactgtcctt tcctaataaa
21241 atgaggaaat tgcatcgcat tgtctgagta ggtgtcattc tattctgggg ggtggggtgg
21301 ggcaggacag caagggggag gattgggaag acaatagcag gcatgctggg gatgcggtgg
21361 gctctatggc acttacacta acacgtggtg tcgcccggag tactggtcga cctccgaagt
21421 tgggggggag caaaagcagg ggaaaataaa aacaaccaaa atgaaggcaa aactactggt
21481 cctgttatat gcatttgtag ctacagatgc agacacaata tgtataggct accatgcgaa
21541 caactcaacc gacactgttg acacaatact cgagaagaat gtggcagtga cacattctgt
21601 taacctgctc gaagacagcc acaacgggaa actatgtaaa ttaaaaggaa tagccccact
21661 acaattgggg aaatgtaaca tcaccggatg gctcttggga aatccagaat gcgactcact
21721 gcttccagcg agatcatggt cctacattgt agaaacacca aactctgaga atggagcatg
21781 ttatccagga gatctcatcg actatgagga actgagggag caattgagct cagtatcatc
21841 attagaaaga ttcgaaatat ttcccaagga aagttcatgg cccaaccaca cattcaacgg
21901 agtaacagta tcatgctccc atagggggaaa aagcagtttt tacagaaatt tgctatggct
21961 gacgaagaag gggattcat acccaaagct gaccaattcc tatgtgaaca ataaagggaa
22021 agaagtcctt gtactatggg gtgttcatca cccgtctagc agtgatgagc aacagagtct
22081 ctatagtaat ggaaatgctt atgtctctgt agcgtcttca aattataaca ggagattcac
22141 cccggaaata gctgcaaggc ccaaagtaag agatcaacat gggaggatga actattactg
22201 gaccttgcta gaacccggag acacaataat atttgaggca actggtaatc taatagcacc
22261 atggtatgct ttcgcactga gtagagggtt tgagtccggc atcatcacct caaacgcgtc
22321 aatgcatgag tgtaacacga agtgtcaaac accccaggga gctataaaca gcaatctccc
22381 tttccagaat atacacccag tcacaatagg agagtgccca aaatatgtca ggagtaccaa
22441 attgaggatg gttacaggac taagaaacat cccatccatt caatacagag gtctatttgg
22501 agccattgct ggttttattg aggggggatg gactggaatg atagatggat ggtatggtta
22561 tcatcatcag aatgaacagg gatcaggcta tgcagcggat caaaaaagca cacaaaatgc
22621 cattaacggg attacaaaca aggtgaactc tgttatcgag aaaatgaaca ctcaattcac
22681 agctgtgggt aaagaattca acaacttaga aaaaaggatg gaaaatttaa ataaaaaagt
22741 tgatgatggg tttctggaca tttggacata taatgcagaa ttgttagttc tactggaaaa
22801 tgaaaggact ttggatttcc atgacttaaa tgtgaagaat ctgtacgaga aagtaaaaag
22861 ccaattaaag aataatgcca aagaaatcgg aaatgggtgt tttgagttct accacaagtg
22921 tgacaatgaa tgcatggaaa gtgtaagaaa tgggacttat gattatccaa aatattcaga
22981 agaatcaaag ttgaacaggg aaaagataga tggagtgaaa ttggaatcaa tgggggtgta
23041 tcagattctg gcgatctact caactgtcgc cagttcactg gtgcttttgg tctccctggg
23101 ggcaatcagt ttctggatgt gttctaatgg gtctttgcag tgcagaatat gcatctgaga
23161 ttaggatttc agaaatataa ggaaaaacac ccttgtttct actacagacg aacatataag
```

-continued

```
23221 gcatccgaaa aaaacgttct agtcccatag gcgccgacta ccggcagcgg ctccgacggc

23281 agccgaggtt tacctcgacg taactggagg tacaaaatta cagcgacgcc tctggcagct

23341 ccggagctgt agcgcccccc cccacagcca gagcggccaa gacaatccga aacggggtag

23401 acctggacgc ggatcgcaag ccgccccggc agcgacctct agccgccgcc gcggagagcg

23461 cgagacggta gcacccgggt agaccgttcc gccgtttccg agacgccccg gcagcgaccc

23521 ctagccgccg ccgccgcgga gagaccgagc cggacggtgc ccgccgggac caggtagacc

23581 gttccgccgt gccccagcca cctccgcgaa gcgaccga
```

What is claimed is:

1. A nucleic acid expression vector selected from the group consisting of a plasmid vector having the sequence of SEQ ID NO:60 and the plasmid vector of SEQ ID NO:60 further comprising at least one DNA nuclear targeting sequence that facilitates nuclear import of the nucleic acid expression vector.

2. A method for the production of influenza virus in a eukaryotic cell, the method comprising introducing the nucleic acid expression vector of claim 1 into the eukaryotic cell.

3. A bacterium, the bacterium comprising the nucleic acid expression vector of claim 1.

* * * * *